United States Patent [19]
Lin et al.

[11] Patent Number: 5,891,675
[45] Date of Patent: Apr. 6, 1999

[54] TNF RECEPTOR DEATH DOMAIN LIGAND PROTEINS

[75] Inventors: Lih-Ling Lin, Concord; Jennifer Chen, Chestnut Hill; Andrea R. Schievella, Winchester; James Graham, Somerville, all of Mass.

[73] Assignee: Genetics Institute, Inc., Cambridge, Mass.

[21] Appl. No.: 839,032

[22] Filed: Apr. 23, 1997

Related U.S. Application Data

[60] Division of Ser. No. 698,551, Aug. 15, 1996, Pat. No. 5,712,381, which is a continuation-in-part of Ser. No. 602,228, Feb. 15, 1996, which is a continuation-in-part of Ser. No. 533,901, Sep. 26, 1995, which is a continuation-in-part of Ser. No. 494,440, Jun. 19, 1995, which is a continuation-in-part of Ser. No. 327,514, Oct. 19, 1994, abandoned.

[51] Int. Cl.$^6$ .......................... C07K 14/705; C12N 15/12
[52] U.S. Cl. ................. 435/69.1; 435/252.3; 435/320.1; 530/350; 536/23.5
[58] Field of Search ................................ 435/69.1, 252.3, 435/320.1; 530/350; 536/23.5

[56] References Cited

U.S. PATENT DOCUMENTS

| | | | |
|---|---|---|---|
| 5,464,938 | 11/1995 | Smith et al. ........................... | 530/350 |
| 5,506,340 | 4/1996 | Heavner . | |
| 5,563,039 | 10/1996 | Goeddel et al. ....................... | 435/7.1 |

FOREIGN PATENT DOCUMENTS

| | | |
|---|---|---|
| A-46127/93 | 9/1993 | Australia . |
| 0 585 939 A2 | 9/1993 | European Pat. Off. . |
| WO 92/03470 | 3/1992 | WIPO . |
| WO 92/03471 | 3/1992 | WIPO . |
| WO 92/14834 | 9/1992 | WIPO . |
| WO 94/01548 | 1/1994 | WIPO . |
| WO 94/10207 | 5/1994 | WIPO . |
| WO 95/31544 | 11/1995 | WIPO . |
| WO 95/33051 | 12/1995 | WIPO . |
| WO 96/34095 | 10/1996 | WIPO . |

OTHER PUBLICATIONS

Miki et al. (1992) Cancer Res. 52:643.
Darnay et al. (1994) J. Biol. Chem. 269:20299.
Kiefer et al. (1992) J. Biol. Chem. 267:12692.
Genbank accession No. T08593 (1993).
Genbank accession No. T07800 (1993).
Genbank accession No. M78050 (1992).
Genbank accession No. M78539 (1992).
Genbank accession No. U44953 (1 Jul. 1996).
Genbank accession No. U48254 (3 Aug. 1996).
Tartaglia et al., Tumor necrosis factor receptor signaling, J. Biol. Chem., 267(7): 4304–4307, Mar. 1992.
Tartaglia et al., Tumor necrosis factor's cytotoxic activity is signaled by the p55 TNF receptor, Cell, 73:213–216, Apr. 1993.
Schall et al., Cell 61:361–370 (1990).
Shimasaki et al., J. Biol. Chem. 266:10646–10653 (1991).
Saragovi et al., Bio/Technology 10:773–778 (1992).
McDowell et al., J. Amer. Chem. Soc. 114:9245–9253 (1992).
Kaufman et al., Nucleic Acids Res. 19:4485–4490 (1991).
Kaufman et al., Methods in Enzymology 185:537–566 (1990).
Cyuris et al., Cell 75:791–803 (1993).
Gietz et al., Nucleic Acids Res. 20:1425 (1992).
Waye et al., Protein Engineering 8:90 (1995).
Auffray et al., Life Sciences 318:263–272 (1995).
Rothe et al., Cell 78:681–692 (1994).
Song et al., The Journal of Biological Chemistry 269:22492–22495 (1994).
Tartaglia et al., Cell 74:845–853 (1993).
Boldin et al., The Journal of Biological Chemistry 270(1):387–391 (1995).
Hsu et al., Cell 81:495–504 (1995).
Boldin et al., FEBS Letters 367:39–44 (1995).

*Primary Examiner*—John Ulm
*Attorney, Agent, or Firm*—Suzanne A. Sprunger; Scott A. Brown

[57] ABSTRACT

Novel TNF receptor death domain ("TNF-R1-DD") ligand proteins are disclosed. Polynucleotides encoding the TNF-R1-DD ligand protein are also disclosed, along with vectors, host cells, and methods of making the TNF-R1-DD ligand protein. Pharmaceutical compositions containing the TNF-R1-DD ligand protein, methods of treating inflammatory conditions, and methods of inhibiting TNF-R death domain binding are also disclosed. Methods of identifying inhibitors of TNF-R death domain binding and inhibitors identified by such methods are also disclosed.

23 Claims, 8 Drawing Sheets

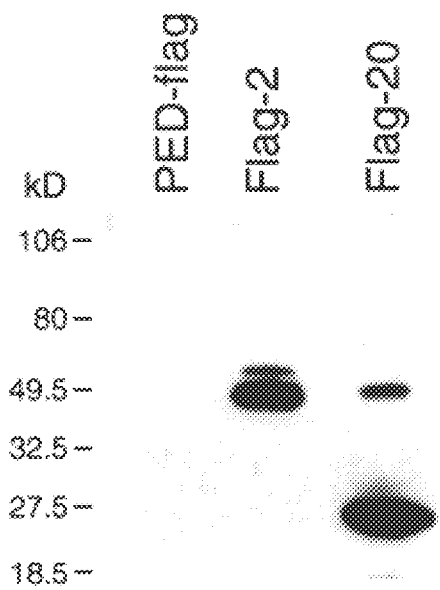

Fig. 4
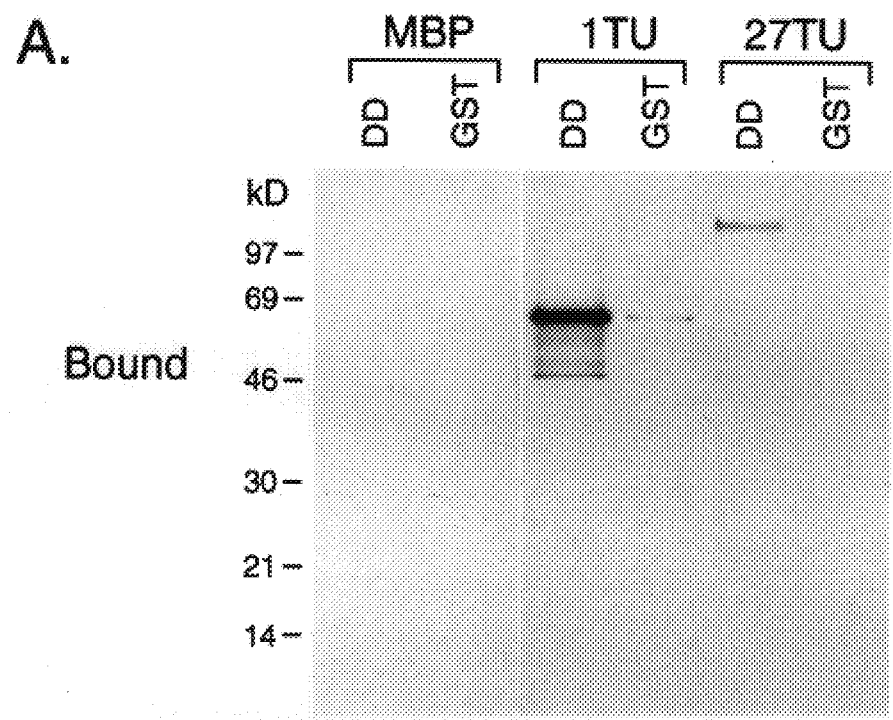
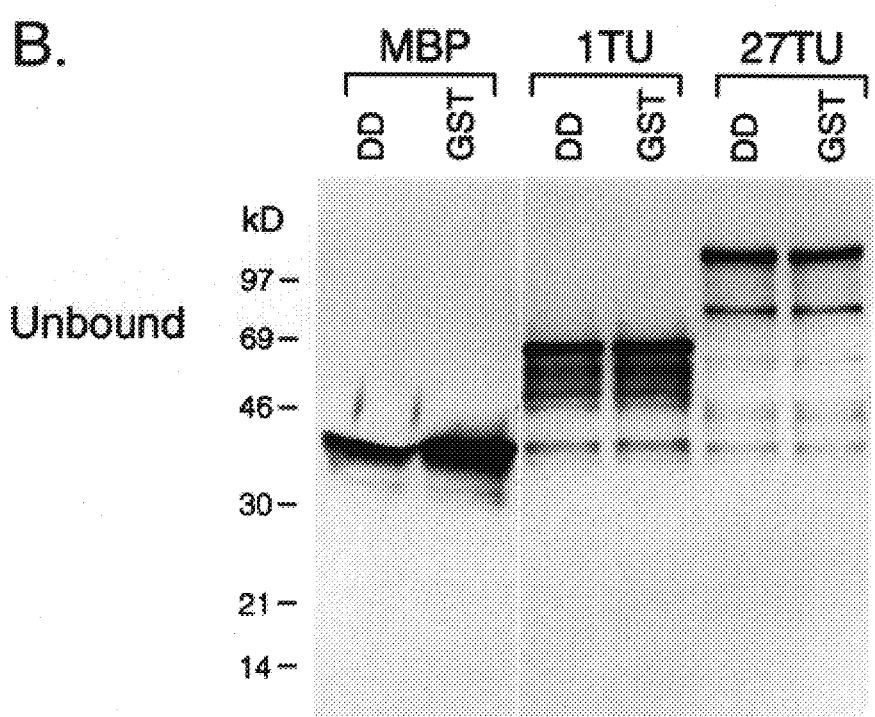

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 2158 base pairs
        ( B ) TYPE: nucleic acid
        ( C ) STRANDEDNESS: double ( D ) TOPOLOGY: linear ( i i ) MOLECULE TYPE: cDNA ( i i i ) HYPOTHETICAL: NO ( i x ) FEATURE:
  ( A ) NAME/KEY: CDS
  ( B ) LOCATION: 2..1231

( x i ) SEQUENCE DESCRIPTION: SEQ ID NO:1:

```
C AGC AAT GCA GGT GAT GGA CCA GGT GGC GAG GGC AGT GTT CAC CTG                46
  Ser Asn Ala Gly Asp Gly Pro Gly Gly Glu Gly Ser Val His Leu
  1               5                   10                  15

GCA AGC TCT CGG GGC ACT TTG TCT GAT AGT GAA ATT GAG ACC AAC TCT              94
Ala Ser Ser Arg Gly Thr Leu Ser Asp Ser Glu Ile Glu Thr Asn Ser
            20                  25                  30

GCC ACA AGC ACC ATC TTT GGT AAA GCC CAC AGC TTG AAG CCA AGC ATA             142
Ala Thr Ser Thr Ile Phe Gly Lys Ala His Ser Leu Lys Pro Ser Ile
                35                  40                  45

AAG GAG AAG CTG GCA GGC AGC CCC ATT CGT ACT TCT GAA GAT GTG AGC             190
Lys Glu Lys Leu Ala Gly Ser Pro Ile Arg Thr Ser Glu Asp Val Ser
            50                  55                  60

CAG CGA GTC TAT CTC TAT GAG GGA CTC CTA GGC AAA GAG CGT TCT ACT             238
Gln Arg Val Tyr Leu Tyr Glu Gly Leu Leu Gly Lys Glu Arg Ser Thr
        65                  70                  75

TTA TGG GAC CAA ATG CAA TTC TGG GAA GAT GCC TTC TTA GAT GCT GTG             286
Leu Trp Asp Gln Met Gln Phe Trp Glu Asp Ala Phe Leu Asp Ala Val
80                  85                  90                  95

ATG TTG GAG AGA GAA GGG ATG GGT ATG GAC CAG GGT CCC CAG GAA ATG             334
Met Leu Glu Arg Glu Gly Met Gly Met Asp Gln Gly Pro Gln Glu Met
                100                 105                 110

ATC GAC AGG TAC CTG TCC CTT GGA GAA CAT GAC CGG AAG CGC CTG GAA             382
Ile Asp Arg Tyr Leu Ser Leu Gly Glu His Asp Arg Lys Arg Leu Glu
                115                 120                 125

GAT GAT GAA GAT CGC TTG CTG GCC ACA CTT CTG CAC AAC CTC ATC TCC             430
Asp Asp Glu Asp Arg Leu Leu Ala Thr Leu Leu His Asn Leu Ile Ser
            130                 135                 140

TAC ATG CTG CTG ATG AAG GTA AAT AAG AAT GAC ATC CGC AAG AAG GTG             478
Tyr Met Leu Leu Met Lys Val Asn Lys Asn Asp Ile Arg Lys Lys Val
145                 150                 155

AGG CGC CTA ATG GGA AAG TCG CAC ATT GGG CTT GTG TAC AGC CAG CAA             526
Arg Arg Leu Met Gly Lys Ser His Ile Gly Leu Val Tyr Ser Gln Gln
160                 165                 170                 175

ATC AAT GAG GTG CTT GAT CAG CTG GCG AAC CTG AAT GGA CGC GAT CTC             574
Ile Asn Glu Val Leu Asp Gln Leu Ala Asn Leu Asn Gly Arg Asp Leu
            180                 185                 190

TCT ATC TGG TCC AGT GGC AGC CGG CAC ATG AAG AAG CAG ACA TTT GTG             622
Ser Ile Trp Ser Ser Gly Ser Arg His Met Lys Lys Gln Thr Phe Val
            195                 200                 205

GTA CAT GCA GGG ACA GAT ACA AAC GGA GAT ATC TTT TTC ATG GAG GTG             670
Val His Ala Gly Thr Asp Thr Asn Gly Asp Ile Phe Phe Met Glu Val
            210                 215                 220

TGC GAT GAC TGT GTG GTG TTG CGT AGT AAC ATC GGA ACA GTG TAT GAG             718
Cys Asp Asp Cys Val Val Leu Arg Ser Asn Ile Gly Thr Val Tyr Glu
225                 230                 235

CGC TGG TGG TAC GAG AAG CTC ATC AAC ATG ACC TAC TGT CCC AAG ACG             766
Arg Trp Trp Tyr Glu Lys Leu Ile Asn Met Thr Tyr Cys Pro Lys Thr
240                 245                 250                 255

AAG GTG TTG TGC TTG TGG CGT AGA AAT GGC TCT GAG ACC CAG CTC AAC             814
Lys Val Leu Cys Leu Trp Arg Arg Asn Gly Ser Glu Thr Gln Leu Asn
            260                 265                 270
```

| | | | | | | | | | | | | | | | | |
|---|---|---|---|---|---|---|---|---|---|---|---|---|---|---|---|---|
| AAG | TTC | TAT | ACT | AAA | AAG | TGT | CGG | GAG | CTG | TAC | TAC | TGT | GTG | AAG | GAC | 862 |
| Lys | Phe | Tyr | Thr 275 | Lys | Lys | Cys | Arg | Glu 280 | Leu | Tyr | Tyr | Cys | Val 285 | Lys | Asp | |
| AGC | ATG | GAG | CGC | GCT | GCC | GCC | CGA | CAG | CAA | AGC | ATC | AAA | CCC | GGA | CCT | 910 |
| Ser | Met | Glu 290 | Arg | Ala | Ala | Ala | Arg | Gln 295 | Gln | Ser | Ile | Lys 300 | Pro | Gly | Pro | |
| GAA | TTG | GGT | GGC | GAG | TTC | CCT | GTG | CAG | GAC | CTG | AAG | ACT | GGT | GAG | GGT | 958 |
| Glu | Leu 305 | Gly | Gly | Glu | Phe | Pro 310 | Val | Gln | Asp | Leu | Lys 315 | Thr | Gly | Glu | Gly | |
| GGC | CTG | CTG | CAG | GTG | ACC | CTG | GAA | GGG | ATC | AAC | CTC | AAA | TTC | ATG | CAC | 1006 |
| Gly 320 | Leu | Leu | Gln | Val | Thr 325 | Leu | Glu | Gly | Ile | Asn 330 | Leu | Lys | Phe | Met | His 335 | |
| AAT | CAG | GTT | TTC | ATA | GAG | CTG | AAT | CAC | ATT | AAA | AAG | TGC | AAT | ACA | GTT | 1054 |
| Asn | Gln | Val | Phe | Ile 340 | Glu | Leu | Asn | His | Ile 345 | Lys | Lys | Cys | Asn | Thr 350 | Val | |
| CGA | GGC | GTC | TTT | GTC | CTG | GAG | GAA | TTT | GTT | CCT | GAA | ATT | AAA | GAA | GTG | 1102 |
| Arg | Gly | Val | Phe 355 | Val | Leu | Glu | Glu | Phe 360 | Val | Pro | Glu | Ile | Lys 365 | Glu | Val | |
| GTG | AGC | CAC | AAG | TAC | AAG | ACA | CCA | ATG | GCC | CAC | GAA | ATC | TGC | TAC | TCC | 1150 |
| Val | Ser | His 370 | Lys | Tyr | Lys | Thr | Pro 375 | Met | Ala | His | Glu | Ile 380 | Cys | Tyr | Ser | |
| GTA | TTA | TGT | CTC | TTC | TCG | TAC | GTG | GCT | GCA | GTT | CAT | AGC | AGT | GAG | GAA | 1198 |
| Val | Leu 385 | Cys | Leu | Phe | Ser | Tyr 390 | Val | Ala | Ala | Val | His 395 | Ser | Ser | Glu | Glu | |
| GAT | CTC | AGA | ACC | CCG | CCC | CGG | CCT | GTC | TCT | AGC | TGATGGAGAG | GGGCTACGCA | | | | 1251 |
| Asp 400 | Leu | Arg | Thr | Pro | Pro 405 | Arg | Pro | Val | Ser | Ser 410 | | | | | | |
| GCTGCCCCAG | CCCAGGGCAC | GCCCCTGGCC | CCTTGCTGTT | CCCAAGTGCA | CGATGCTGCT | 1311 |
| GTGACTGAGG | AGTGGATGAT | GCTCGTGTGT | CCTCTGCAAG | CCCCCTGCTG | TGGCTTGGGT | 1371 |
| GGGTACCGGT | TATGTGTCCC | TCTGAGTGTG | TCTTGAGCGT | GTCCACCTTC | TCCCTCTCCA | 1431 |
| CTCCCAGAAG | ACCAAACTGC | CTTCCCTCA | GGGCTCAAGA | ATGTGTACAG | TCTGTGGGGC | 1491 |
| CGGTGTGAAC | CCACTATTTT | GTGTCCTTGA | GACATTTGTG | TTGTGGTTCC | TTGTCCTTGT | 1551 |
| CCCTGGCGTT | AACTGTCCAC | TGCAAGAGTC | TGGCTCTCCC | TTCTCTGTGA | CCCGGCATGA | 1611 |
| CTGGGCGCCT | GGAGCAGTTT | CACTCTGTGA | GGAGTGAGGG | AACCCTGGGG | CTCACCCTCT | 1671 |
| CAGAGGAAGG | GCACAGAGAG | GAAGGGAAGA | ATTGGGGGGC | AGCCGGAGTG | AGTGGCAGCC | 1731 |
| TCCCTGCTTC | CTTCTGCATT | CCCAAGCCGG | CAGCTACTGC | CCAGGGCCCG | CAGTGTTGGC | 1791 |
| TGCTGCCTGC | CACAGCCTCT | GTGACTGCAG | TGGAGCGGCG | AATTCCCTGT | GGCCTGCCAC | 1851 |
| GCCTTCGGCA | TCAGAGGATG | GAGTGGTCGA | GGCTAGTGGA | GTCCCAGGGA | CCGCTGGCTG | 1911 |
| CTCTGCCTGA | GCATCAGGGA | GGGGGCAGGA | AAGACCAAGC | TGGGTTTGCA | CATCTGTCTG | 1971 |
| CAGGCTGTCT | CTCCAGGCAC | GGGGTGTCAG | GAGGGAGAGA | CAGCCTGGGT | ATGGGCAAGA | 2031 |
| AATGACTGTA | AATATTTCAG | CCCCACATTA | TTTATAGAAA | ATGTACAGTT | GTGTGAATGT | 2091 |
| GAAATAAATG | TCCTCACCTC | CCAAAAAAAA | AAAAAAAAAA | AAAAAAAAAA | AAAAAAAAAA | 2151 |
| AAAAAAA | | | | | | 2158 |

( 2 ) INFORMATION FOR SEQ ID NO:2:

( i ) SEQUENCE CHARACTERISTICS:
        ( A ) LENGTH: 410 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Ser | Asn | Ala | Gly | Asp | Gly | Pro | Gly | Gly | Glu | Gly | Ser | Val | His | Leu | Ala |
| 1 | | | | 5 | | | | | 10 | | | | | 15 | |
| Ser | Ser | Arg | Gly | Thr | Leu | Ser | Asp | Ser | Glu | Ile | Glu | Thr | Asn | Ser | Ala |
| | | | 20 | | | | | 25 | | | | | 30 | | |
| Thr | Ser | Thr | Ile | Phe | Gly | Lys | Ala | His | Ser | Leu | Lys | Pro | Ser | Ile | Lys |
| | | 35 | | | | | 40 | | | | | 45 | | | |
| Glu | Lys | Leu | Ala | Gly | Ser | Pro | Ile | Arg | Thr | Ser | Glu | Asp | Val | Ser | Gln |
| | 50 | | | | | 55 | | | | | 60 | | | | |
| Arg | Val | Tyr | Leu | Tyr | Glu | Gly | Leu | Leu | Gly | Lys | Glu | Arg | Ser | Thr | Leu |
| 65 | | | | | 70 | | | | | 75 | | | | | 80 |
| Trp | Asp | Gln | Met | Gln | Phe | Trp | Glu | Asp | Ala | Phe | Leu | Asp | Ala | Val | Met |
| | | | | 85 | | | | | 90 | | | | | 95 | |
| Leu | Glu | Arg | Glu | Gly | Met | Gly | Met | Asp | Gln | Gly | Pro | Gln | Glu | Met | Ile |
| | | | 100 | | | | | 105 | | | | | 110 | | |
| Asp | Arg | Tyr | Leu | Ser | Leu | Gly | Glu | His | Asp | Arg | Lys | Arg | Leu | Glu | Asp |
| | | 115 | | | | | 120 | | | | | 125 | | | |
| Asp | Glu | Asp | Arg | Leu | Leu | Ala | Thr | Leu | Leu | His | Asn | Leu | Ile | Ser | Tyr |
| | 130 | | | | | 135 | | | | | 140 | | | | |
| Met | Leu | Leu | Met | Lys | Val | Asn | Lys | Asn | Asp | Ile | Arg | Lys | Lys | Val | Arg |
| 145 | | | | | 150 | | | | | 155 | | | | | 160 |
| Arg | Leu | Met | Gly | Lys | Ser | His | Ile | Gly | Leu | Val | Tyr | Ser | Gln | Gln | Ile |
| | | | | 165 | | | | | 170 | | | | | 175 | |
| Asn | Glu | Val | Leu | Asp | Gln | Leu | Ala | Asn | Leu | Asn | Gly | Arg | Asp | Leu | Ser |
| | | | 180 | | | | | 185 | | | | | 190 | | |
| Ile | Trp | Ser | Ser | Gly | Ser | Arg | His | Met | Lys | Lys | Gln | Thr | Phe | Val | Val |
| | | 195 | | | | | 200 | | | | | 205 | | | |
| His | Ala | Gly | Thr | Asp | Thr | Asn | Gly | Asp | Ile | Phe | Phe | Met | Glu | Val | Cys |
| | 210 | | | | | 215 | | | | | 220 | | | | |
| Asp | Asp | Cys | Val | Val | Leu | Arg | Ser | Asn | Ile | Gly | Thr | Val | Tyr | Glu | Arg |
| 225 | | | | | 230 | | | | | 235 | | | | | 240 |
| Trp | Trp | Tyr | Glu | Lys | Leu | Ile | Asn | Met | Thr | Tyr | Cys | Pro | Lys | Thr | Lys |
| | | | | 245 | | | | | 250 | | | | | 255 | |
| Val | Leu | Cys | Leu | Trp | Arg | Arg | Asn | Gly | Ser | Glu | Thr | Gln | Leu | Asn | Lys |
| | | | 260 | | | | | 265 | | | | | 270 | | |
| Phe | Tyr | Thr | Lys | Lys | Cys | Arg | Glu | Leu | Tyr | Tyr | Cys | Val | Lys | Asp | Ser |
| | | 275 | | | | | 280 | | | | | 285 | | | |
| Met | Glu | Arg | Ala | Ala | Ala | Arg | Gln | Gln | Ser | Ile | Lys | Pro | Gly | Pro | Glu |
| | 290 | | | | | 295 | | | | | 300 | | | | |
| Leu | Gly | Gly | Glu | Phe | Pro | Val | Gln | Asp | Leu | Lys | Thr | Gly | Glu | Gly | Gly |
| 305 | | | | | 310 | | | | | 315 | | | | | 320 |
| Leu | Leu | Gln | Val | Thr | Leu | Glu | Gly | Ile | Asn | Leu | Lys | Phe | Met | His | Asn |
| | | | | 325 | | | | | 330 | | | | | 335 | |
| Gln | Val | Phe | Ile | Glu | Leu | Asn | His | Ile | Lys | Lys | Cys | Asn | Thr | Val | Arg |
| | | | 340 | | | | | 345 | | | | | 350 | | |
| Gly | Val | Phe | Val | Leu | Glu | Glu | Phe | Val | Pro | Glu | Ile | Lys | Glu | Val | Val |
| | | 355 | | | | | 360 | | | | | 365 | | | |
| Ser | His | Lys | Tyr | Lys | Thr | Pro | Met | Ala | His | Glu | Ile | Cys | Tyr | Ser | Val |
| | 370 | | | | | 375 | | | | | 380 | | | | |
| Leu | Cys | Leu | Phe | Ser | Tyr | Val | Ala | Ala | Val | His | Ser | Ser | Glu | Glu | Asp |
| 385 | | | | | 390 | | | | | 395 | | | | | 400 |
| Leu | Arg | Thr | Pro | Pro | Arg | Pro | Val | Ser | Ser | | | | | | |
| | | | | 405 | | | | | 410 | | | | | | |

( 2 ) INFORMATION FOR SEQ ID NO:3:

( i ) SEQUENCE CHARACTERISTICS:
  ( A ) LENGTH: 826 base pairs
  ( B ) TYPE: nucleic acid
  ( C ) STRANDEDNESS: double
  ( D ) TOPOLOGY: linear ( i i ) MOLECULE TYPE: cDNA ( i i i ) HYPOTHETICAL: NO ( i x ) FEATURE:
  ( A ) NAME/KEY: CDS
  ( B ) LOCATION: 2..415

( x i ) SEQUENCE DESCRIPTION: SEQ ID NO:3:

```
G GAG GTG CAG GAC CTC TTC GAA GCC CAG GGC AAT GAC CGA CTG AAG          46
  Glu Val Gln Asp Leu Phe Glu Ala Gln Gly Asn Asp Arg Leu Lys
   1               5                  10                  15

CTG CTG GTG CTG TAC AGT GGA GAG GAT GAT GAG CTG CTA CAG CGG GCA        94
Leu Leu Val Leu Tyr Ser Gly Glu Asp Asp Glu Leu Leu Gln Arg Ala
                 20                  25                  30

GCT GCC GGG GGC TTG GCC ATG CTT ACC TCC ATG CGG CCC ACG CTC TGC        142
Ala Ala Gly Gly Leu Ala Met Leu Thr Ser Met Arg Pro Thr Leu Cys
             35                  40                  45

AGC CGC ATT CCC CAA GTG ACC ACA CAC TGG CTG GAG ATC CTG CAG GCC        190
Ser Arg Ile Pro Gln Val Thr Thr His Trp Leu Glu Ile Leu Gln Ala
         50                  55                  60

CTG CTT CTG AGC TCC AAC CAG GAG CTG CAG CAC CGG GGT GCT GTG GTG        238
Leu Leu Leu Ser Ser Asn Gln Glu Leu Gln His Arg Gly Ala Val Val
     65                  70                  75

GTG CTG AAC ATG GTG GAG GCC TCG AGG GAG ATT GCC AGC ACC CTG ATG        286
Val Leu Asn Met Val Glu Ala Ser Arg Glu Ile Ala Ser Thr Leu Met
 80                  85                  90                  95

GAG AGT GAG ATG ATG GAG ATC TTG TCA GTG CTA GCT AAG GGT GAC CAC        334
Glu Ser Glu Met Met Glu Ile Leu Ser Val Leu Ala Lys Gly Asp His
                100                 105                 110

AGC CCT GTC ACA AGG GCT GCT GCA GCC TGC CTG GAC AAA GCA GTG GAA        382
Ser Pro Val Thr Arg Ala Ala Ala Ala Cys Leu Asp Lys Ala Val Glu
            115                 120                 125

TAT GGG CTT ATC CAA CCC AAC CAA GAT GGA GAG TGAGGGGTT GTCCCTGGGC       435
Tyr Gly Leu Ile Gln Pro Asn Gln Asp Gly Glu
        130                 135

CCAAGGCTCA TGCACACGCT ACCTATTGTG GCACGGAGAG TAAGGACGGA AGCAGCTTTG      495

GCTGGTGGTG GCTGGCATGC CCAATACTCT TGCCCATCCT CGCTTGCTGC CCTAGGATGT      555

CCTCTGTTCT GAGTCAGCGG CCACGTTCAG TCACACAGCC CTGCTTGGCC AGCACTGCCT      615

GCAGCCTCAC TCAGAGGGGC CCTTTTTCTG TACTACTGTA GTCAGCTGGG AATGGGGAAG      675

GTGCATCCCA ACACAGCCTG TGGATCCTGG GGCATTTGGA AGGGCGCACA CATCAGCAGC      735

CTCACCAGCT GTGAGCCTGC TATCAGGCCT GCCCCTCCAA TAAAAGTGTG TAGAACTCCA      795

AAAAAAAAAA AAAAAAAAAA AAAAAAAAA A                                      826
```

( 2 ) INFORMATION FOR SEQ ID NO:4:

( i ) SEQUENCE CHARACTERISTICS:
    ( A ) LENGTH: 138 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

Glu Val Gln Asp Leu Phe Glu Ala Gln Gly Asn Asp Arg Leu Lys Leu

|  | 1 |  |  |  | 5 |  |  |  |  | 10 |  |  |  |  | 15 |  |
|---|---|---|---|---|---|---|---|---|---|---|---|---|---|---|---|---|
| Leu | Val | Leu | Tyr<br>20 | Ser | Gly | Glu | Asp | Asp<br>25 | Glu | Leu | Leu | Gln | Arg<br>30 | Ala | Ala |

| Ala | Gly | Gly<br>35 | Leu | Ala | Met | Leu | Thr<br>40 | Ser | Met | Arg | Pro | Thr<br>45 | Leu | Cys | Ser |

| Arg | Ile<br>50 | Pro | Gln | Val | Thr | Thr<br>55 | His | Trp | Leu | Glu | Ile<br>60 | Leu | Gln | Ala | Leu |

| Leu<br>65 | Leu | Ser | Ser | Asn | Gln<br>70 | Glu | Leu | Gln | His | Arg<br>75 | Gly | Ala | Val | Val | Val<br>80 |

| Leu | Asn | Met | Val | Glu<br>85 | Ala | Ser | Arg | Glu | Ile<br>90 | Ala | Ser | Thr | Leu | Met<br>95 | Glu |

| Ser | Glu | Met | Met<br>100 | Glu | Ile | Leu | Ser | Val<br>105 | Leu | Ala | Lys | Gly | Asp<br>110 | His | Ser |

| Pro | Val | Thr<br>115 | Arg | Ala | Ala | Ala | Ala<br>120 | Cys | Leu | Asp | Lys | Ala<br>125 | Val | Glu | Tyr |

| Gly | Leu<br>130 | Ile | Gln | Pro | Asn | Gln<br>135 | Asp | Gly | Glu |

( 2 ) INFORMATION FOR SEQ ID NO:5:

( i ) SEQUENCE CHARACTERISTICS:
        ( A ) LENGTH: 722 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 2..559

( x i ) SEQUENCE DESCRIPTION: SEQ ID NO:5:

| G | GAG | AAG | CCG | CTG | CAC | GCC | CTG | CTG | CAC | GGC | CGC | GGG | GTT | TGC | CTC | 46 |
|---|---|---|---|---|---|---|---|---|---|---|---|---|---|---|---|---|
|  | Glu | Lys | Pro | Leu | His | Ala | Leu | Leu | His | Gly | Arg | Gly | Val | Cys | Leu |  |
|  | 1 |  |  |  | 5 |  |  |  |  | 10 |  |  |  |  | 15 |  |

| AAC | GAA | AAG | AGC | TAC | CGC | GAG | CAA | GTC | AAG | ATC | GAG | AGA | GAC | TCC | CGT | 94 |
|---|---|---|---|---|---|---|---|---|---|---|---|---|---|---|---|---|
| Asn | Glu | Lys | Ser | Tyr | Arg | Glu | Gln | Val | Lys | Ile | Glu | Arg | Asp | Ser | Arg |  |
|  |  |  | 20 |  |  |  |  | 25 |  |  |  |  | 30 |  |  |  |

| GAG | CAC | GAG | GAG | CCC | ACC | ACC | TCT | GAG | ATG | GCC | GAG | GAG | ACC | TAC | TCC | 142 |
|---|---|---|---|---|---|---|---|---|---|---|---|---|---|---|---|---|
| Glu | His | Glu | Glu | Pro | Thr | Thr | Ser | Glu | Met | Ala | Glu | Glu | Thr | Tyr | Ser |  |
|  |  |  | 35 |  |  |  |  | 40 |  |  |  |  | 45 |  |  |  |

| CCC | AAG | ATC | TTC | CGG | CCC | AAA | CAC | ACC | CGC | ATC | TCC | GAG | CTG | AAG | GCT | 190 |
|---|---|---|---|---|---|---|---|---|---|---|---|---|---|---|---|---|
| Pro | Lys | Ile | Phe | Arg | Pro | Lys | His | Thr | Arg | Ile | Ser | Glu | Leu | Lys | Ala |  |
|  |  | 50 |  |  |  |  | 55 |  |  |  |  | 60 |  |  |  |  |

| GAA | GCA | GTG | AAG | AAG | GAC | CGC | AGA | AAG | AAG | CTG | ACC | CAG | TCC | AAG | TTT | 238 |
|---|---|---|---|---|---|---|---|---|---|---|---|---|---|---|---|---|
| Glu | Ala | Val | Lys | Lys | Asp | Arg | Arg | Lys | Lys | Leu | Thr | Gln | Ser | Lys | Phe |  |
|  | 65 |  |  |  |  | 70 |  |  |  |  | 75 |  |  |  |  |  |

| GTC | GGG | GGA | GCC | GAG | AAC | ACT | GCC | CAC | CCC | CGG | ATC | ATC | TCT | GAA | CCT | 286 |
|---|---|---|---|---|---|---|---|---|---|---|---|---|---|---|---|---|
| Val | Gly | Gly | Ala | Glu | Asn | Thr | Ala | His | Pro | Arg | Ile | Ile | Ser | Glu | Pro |  |
| 80 |  |  |  |  | 85 |  |  |  |  | 90 |  |  |  |  | 95 |  |

| GAG | ATG | AGA | CAG | GAG | TCT | GAG | CAG | GGC | CCC | TGC | CGC | AGA | CAC | ATG | GAG | 334 |
|---|---|---|---|---|---|---|---|---|---|---|---|---|---|---|---|---|
| Glu | Met | Arg | Gln | Glu | Ser | Glu | Gln | Gly | Pro | Cys | Arg | Arg | His | Met | Glu |  |
|  |  |  | 100 |  |  |  |  | 105 |  |  |  |  | 110 |  |  |  |

| GCT | TCC | CTG | CAG | GAG | CTC | AAA | GCC | AGC | CCA | CGC | ATG | GTG | CCC | CGT | GCT | 382 |
|---|---|---|---|---|---|---|---|---|---|---|---|---|---|---|---|---|
| Ala | Ser | Leu | Gln | Glu | Leu | Lys | Ala | Ser | Pro | Arg | Met | Val | Pro | Arg | Ala |  |
|  |  |  | 115 |  |  |  |  | 120 |  |  |  |  | 125 |  |  |  |

| GTG | TAC | CTG | CCC | AAT | TGT | GAC | CGC | AAA | GGA | TTC | TAC | AAG | AGA | AAG | CAG | 430 |
|---|---|---|---|---|---|---|---|---|---|---|---|---|---|---|---|---|
| Val | Tyr | Leu | Pro | Asn | Cys | Asp | Arg | Lys | Gly | Phe | Tyr | Lys | Arg | Lys | Gln |  |
|  |  | 130 |  |  |  |  | 135 |  |  |  |  | 140 |  |  |  |  |

```
TGC  AAA  CCT  TCC  CGT  GGC  CGC  AAG  CGT  GGC  ATC  TGC  TGG  TGC  GTG  GAC        478
Cys  Lys  Pro  Ser  Arg  Gly  Arg  Lys  Arg  Gly  Ile  Cys  Trp  Cys  Val  Asp
145                           150                          155

AAG  TAC  GGG  ATG  AAG  CTG  CCA  GGC  ATG  GAG  TAC  GTT  GAC  GGG  GAC  TTT        526
Lys  Tyr  Gly  Met  Lys  Leu  Pro  Gly  Met  Glu  Tyr  Val  Asp  Gly  Asp  Phe
160                           165                          170                     175

CAG  TGC  CAC  ACC  TTC  GAC  AGC  AGC  AAC  GTT  GAG  TGATGCGTCC  CCCCCCAACC        579
Gln  Cys  His  Thr  Phe  Asp  Ser  Ser  Asn  Val  Glu
                    180                           185

TTTCCCTCAC  CCCCTTCCAC  CCCCAGCCCC  GACTCCAGCC  AGCGCCTCCC  TCCACCCCAG               639

GACGCCACTC  ATTTCATCTC  ATTTAAGGGA  AAAATATATA  TCTATCTATT  TGAGGAAAAA               699

AAAAAAAAAA  AAAAAAAAAA  AAA                                                          722
```

(2) INFORMATION FOR SEQ ID NO:6:

(i) SEQUENCE CHARACTERISTICS:
        (A) LENGTH: 186 amino acids
        (B) TYPE: amino acid
        (D) TOPOLOGY: linear (ii) MOLECULE TYPE: protein (xi) SEQUENCE DESCRIPTION: SEQ ID NO:6:

```
Glu  Lys  Pro  Leu  His  Ala  Leu  Leu  His  Gly  Arg  Gly  Val  Cys  Leu  Asn
 1                   5                        10                         15

Glu  Lys  Ser  Tyr  Arg  Glu  Gln  Val  Lys  Ile  Glu  Arg  Asp  Ser  Arg  Glu
                20                        25                        30

His  Glu  Glu  Pro  Thr  Thr  Ser  Glu  Met  Ala  Glu  Glu  Thr  Tyr  Ser  Pro
           35                        40                        45

Lys  Ile  Phe  Arg  Pro  Lys  His  Thr  Arg  Ile  Ser  Glu  Leu  Lys  Ala  Glu
          50                        55                        60

Ala  Val  Lys  Lys  Asp  Arg  Arg  Lys  Lys  Leu  Thr  Gln  Ser  Lys  Phe  Val
65                        70                        75                        80

Gly  Gly  Ala  Glu  Asn  Thr  Ala  His  Pro  Arg  Ile  Ile  Ser  Glu  Pro  Glu
                85                        90                        95

Met  Arg  Gln  Glu  Ser  Glu  Gln  Gly  Pro  Cys  Arg  Arg  His  Met  Glu  Ala
               100                       105                      110

Ser  Leu  Gln  Glu  Leu  Lys  Ala  Ser  Pro  Arg  Met  Val  Pro  Arg  Ala  Val
               115                       120                      125

Tyr  Leu  Pro  Asn  Cys  Asp  Arg  Lys  Gly  Phe  Tyr  Lys  Arg  Lys  Gln  Cys
               130                       135                      140

Lys  Pro  Ser  Arg  Gly  Arg  Lys  Arg  Gly  Ile  Cys  Trp  Cys  Val  Asp  Lys
145                       150                       155                      160

Tyr  Gly  Met  Lys  Leu  Pro  Gly  Met  Glu  Tyr  Val  Asp  Gly  Asp  Phe  Gln
                    165                       170                      175

Cys  His  Thr  Phe  Asp  Ser  Ser  Asn  Val  Glu
               180                       185
```

(2) INFORMATION FOR SEQ ID NO:7:

(i) SEQUENCE CHARACTERISTICS:
        (A) LENGTH: 1023 base pairs
        (B) TYPE: nucleic acid
        (C) STRANDEDNESS: double
        (D) TOPOLOGY: linear (ii) MOLECULE TYPE: cDNA (iii) HYPOTHETICAL: NO -continued (ix) FEATURE:
  (A) NAME/KEY: CDS
  (B) LOCATION: 57..875

(xi) SEQUENCE DESCRIPTION: SEQ ID NO:7:

```
CCCTGCACTC TCGCTCTCCT GCCCCACCCC GAGGTAAAGG GGGCGACTAA GAGAAG                    56

ATG GTG TTG CTC ACC GCG GTC CTC CTG CTG CTG GCC GCC TAT GCG GGG                 104
Met Val Leu Leu Thr Ala Val Leu Leu Leu Leu Ala Ala Tyr Ala Gly
 1               5                  10                  15

CCG GCC CAG AGC CTG GGC TCC TTC GTG CAC TGC GAG CCC TGC GAC GAG                 152
Pro Ala Gln Ser Leu Gly Ser Phe Val His Cys Glu Pro Cys Asp Glu
                20                  25                  30

AAA GCC CTC TCC ATG TGC CCC CCC AGC CCC CTG GGC TGC GAG CTG GTC                 200
Lys Ala Leu Ser Met Cys Pro Pro Ser Pro Leu Gly Cys Glu Leu Val
            35                  40                  45

AAG GAG CCG GGC TGC GGC TGC TGC ATG ACC TGC GCC CTG GCC GAG GGG                 248
Lys Glu Pro Gly Cys Gly Cys Cys Met Thr Cys Ala Leu Ala Glu Gly
        50                  55                  60

CAG TCG TGC GGC GTC TAC ACC GAG CGC TGC GCC CAG GGG CTG CGC TGC                 296
Gln Ser Cys Gly Val Tyr Thr Glu Arg Cys Ala Gln Gly Leu Arg Cys
 65                  70                  75                  80

CTC CCC CGG CAG GAC GAG GAG AAG CCG CTG CAC GCC CTG CTG CAC GGC                 344
Leu Pro Arg Gln Asp Glu Glu Lys Pro Leu His Ala Leu Leu His Gly
                85                  90                  95

CGC GGG GTT TGC CTC AAC GAA AAG AGC TAC CGC GAG CAA GTC AAG ATC                 392
Arg Gly Val Cys Leu Asn Glu Lys Ser Tyr Arg Glu Gln Val Lys Ile
                100                 105                 110

GAG AGA GAC TCC CGT GAG CAC GAG GAG CCC ACC ACC TCT GAG ATG GCC                 440
Glu Arg Asp Ser Arg Glu His Glu Glu Pro Thr Thr Ser Glu Met Ala
            115                 120                 125

GAG GAG ACC TAC TCC CCC AAG ATC TTC CGG CCC AAA CAC ACC CGC ATC                 488
Glu Glu Thr Tyr Ser Pro Lys Ile Phe Arg Pro Lys His Thr Arg Ile
        130                 135                 140

TCC GAG CTG AAG GCT GAA GCA GTG AAG AAG GAC CGC AGA AAG AAG CTG                 536
Ser Glu Leu Lys Ala Glu Ala Val Lys Lys Asp Arg Arg Lys Lys Leu
145                 150                 155                 160

ACC CAG TCC AAG TTT GTC GGG GGA GCC GAG AAC ACT GCC CAC CCC CGG                 584
Thr Gln Ser Lys Phe Val Gly Gly Ala Glu Asn Thr Ala His Pro Arg
                165                 170                 175

ATC ATC TCT GCA CCT GAG ATG AGA CAG GAG TCT GAG CAG GGC CCC TGC                 632
Ile Ile Ser Ala Pro Glu Met Arg Gln Glu Ser Glu Gln Gly Pro Cys
                180                 185                 190

CGC AGA CAC ATG GAG GCT TCC CTG CAG GAG CTC AAA GCC AGC CCA CGC                 680
Arg Arg His Met Glu Ala Ser Leu Gln Glu Leu Lys Ala Ser Pro Arg
            195                 200                 205

ATG GTG CCC CGT GCT GTG TAC CTG CCC AAT TGT GAC CGC AAA GGA TTC                 728
Met Val Pro Arg Ala Val Tyr Leu Pro Asn Cys Asp Arg Lys Gly Phe
210                 215                 220

TAC AAG AGA AAG CAG TGC AAA CCT TCC CGT GGC CGC AAG CGT GGC ATC                 776
Tyr Lys Arg Lys Gln Cys Lys Pro Ser Arg Gly Arg Lys Arg Gly Ile
225                 230                 235                 240

TGC TGG TGC GTG GAC AAG TAC GGG ATG AAG CTG CCA GGC ATG GAG TAC                 824
Cys Trp Cys Val Asp Lys Tyr Gly Met Lys Leu Pro Gly Met Glu Tyr
                245                 250                 255

GTT GAC GGG GAC TTT CAG TGC CAC ACC TTC GAC AGC AGC AAC GTT GAG                 872
Val Asp Gly Asp Phe Gln Cys His Thr Phe Asp Ser Ser Asn Val Glu
                260                 265                 270

TGATGCGTCC CCCCCCAACC TTTCCCTCAC CCCCTCCCAC CCCCAGCCCC GACTCCAGCC               932

AGCGCCTCCC TCCACCCCAG GACGCCACTC ATTTCATCTC ATTTAAGGGA AAAATATATA               992
```

TCTATCTATT TGAAAAAAAA AAAAAAACC C                                                                              1023

(2) INFORMATION FOR SEQ ID NO:8:

(i) SEQUENCE CHARACTERISTICS:
        (A) LENGTH: 272 amino acids
        (B) TYPE: amino acid
        (D) TOPOLOGY: linear (ii) MOLECULE TYPE: protein (xi) SEQUENCE DESCRIPTION: SEQ ID NO:8:

| Met | Val | Leu | Leu | Thr | Ala | Val | Leu | Leu | Leu | Ala | Ala | Tyr | Ala | Gly |
|---|---|---|---|---|---|---|---|---|---|---|---|---|---|---|
| 1 | | | | 5 | | | | | 10 | | | | | 15 |
| Pro | Ala | Gln | Ser | Leu | Gly | Ser | Phe | Val | His | Cys | Glu | Pro | Cys | Asp | Glu |
| | | | 20 | | | | | 25 | | | | | 30 | | |
| Lys | Ala | Leu | Ser | Met | Cys | Pro | Pro | Ser | Pro | Leu | Gly | Cys | Glu | Leu | Val |
| | | | 35 | | | | 40 | | | | | 45 | | | |
| Lys | Glu | Pro | Gly | Cys | Gly | Cys | Cys | Met | Thr | Cys | Ala | Leu | Ala | Glu | Gly |
| | 50 | | | | | 55 | | | | | | 60 | | | |
| Gln | Ser | Cys | Gly | Val | Tyr | Thr | Glu | Arg | Cys | Ala | Gln | Gly | Leu | Arg | Cys |
| 65 | | | | | 70 | | | | | 75 | | | | | 80 |
| Leu | Pro | Arg | Gln | Asp | Glu | Glu | Lys | Pro | Leu | His | Ala | Leu | Leu | His | Gly |
| | | | | 85 | | | | | 90 | | | | | 95 | |
| Arg | Gly | Val | Cys | Leu | Asn | Glu | Lys | Ser | Tyr | Arg | Glu | Gln | Val | Lys | Ile |
| | | | 100 | | | | | 105 | | | | | 110 | | |
| Glu | Arg | Asp | Ser | Arg | Glu | His | Glu | Glu | Pro | Thr | Thr | Ser | Glu | Met | Ala |
| | | 115 | | | | | 120 | | | | | 125 | | | |
| Glu | Glu | Thr | Tyr | Ser | Pro | Lys | Ile | Phe | Arg | Pro | Lys | His | Thr | Arg | Ile |
| | 130 | | | | | 135 | | | | | 140 | | | | |
| Ser | Glu | Leu | Lys | Ala | Glu | Ala | Val | Lys | Lys | Asp | Arg | Arg | Lys | Lys | Leu |
| 145 | | | | | 150 | | | | | 155 | | | | | 160 |
| Thr | Gln | Ser | Lys | Phe | Val | Gly | Gly | Ala | Glu | Asn | Thr | Ala | His | Pro | Arg |
| | | | | 165 | | | | | 170 | | | | | 175 | |
| Ile | Ile | Ser | Ala | Pro | Glu | Met | Arg | Gln | Glu | Ser | Glu | Gln | Gly | Pro | Cys |
| | | | 180 | | | | | 185 | | | | | 190 | | |
| Arg | Arg | His | Met | Glu | Ala | Ser | Leu | Gln | Glu | Leu | Lys | Ala | Ser | Pro | Arg |
| | | 195 | | | | | 200 | | | | | 205 | | | |
| Met | Val | Pro | Arg | Ala | Val | Tyr | Leu | Pro | Asn | Cys | Asp | Arg | Lys | Gly | Phe |
| | 210 | | | | | 215 | | | | | 220 | | | | |
| Tyr | Lys | Arg | Lys | Gln | Cys | Lys | Pro | Ser | Arg | Gly | Arg | Lys | Arg | Gly | Ile |
| 225 | | | | | 230 | | | | | 235 | | | | | 240 |
| Cys | Trp | Cys | Val | Asp | Lys | Tyr | Gly | Met | Lys | Leu | Pro | Gly | Met | Glu | Tyr |
| | | | | 245 | | | | | 250 | | | | | 255 | |
| Val | Asp | Gly | Asp | Phe | Gln | Cys | His | Thr | Phe | Asp | Ser | Ser | Asn | Val | Glu |
| | | | 260 | | | | | 265 | | | | | 270 | | |

(2) INFORMATION FOR SEQ ID NO:9:

(i) SEQUENCE CHARACTERISTICS:
        (A) LENGTH: 1694 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS ( B ) LOCATION: 2..931

( x i ) SEQUENCE DESCRIPTION: SEQ ID NO:9:

```
C TCT CTC AAG GCC AAC ATC CCT GAG GTG GAA GCT GTC CTC AAC ACC            46
  Ser Leu Lys Ala Asn Ile Pro Glu Val Glu Ala Val Leu Asn Thr
   1               5                  10                  15

GAC AGG AGT TTG GTG TGT GAT GGG AAG AGG GGC TTA TTA ACT CGT CTG          94
Asp Arg Ser Leu Val Cys Asp Gly Lys Arg Gly Leu Leu Thr Arg Leu
             20                  25                  30

CTG CAG GTC ATG AAG AAG GAG CCA GCA GAG TCG TCT TTC AGG TTT TGG         142
Leu Gln Val Met Lys Lys Glu Pro Ala Glu Ser Ser Phe Arg Phe Trp
         35                  40                  45

CAA GCT CGG GCT GTG GAG AGT TTC CTC CGA GGG ACC ACC TCC TAT GCA         190
Gln Ala Arg Ala Val Glu Ser Phe Leu Arg Gly Thr Thr Ser Tyr Ala
         50                  55                  60

GAC CAG ATG TTC CTG CTG AAG CGA GGC CTC TTG GAG CAC ATC CTT TAC         238
Asp Gln Met Phe Leu Leu Lys Arg Gly Leu Leu Glu His Ile Leu Tyr
 65                  70                  75

TGC ATT GTG GAC AGC GAG TGT AAG TCA AGG GAT GTG CTC CAG AGT TAC         286
Cys Ile Val Asp Ser Glu Cys Lys Ser Arg Asp Val Leu Gln Ser Tyr
 80                  85                  90                  95

TTT GAC CTC CTG GGG GAG CTG ATG AAG TTC AAC GTT GAT GCA TTC AAG         334
Phe Asp Leu Leu Gly Glu Leu Met Lys Phe Asn Val Asp Ala Phe Lys
                 100                 105                 110

AGA TTC AAT AAA TAT ATC AAC ACC GAT GCA AAG TTC CAG GTA TTC CTG         382
Arg Phe Asn Lys Tyr Ile Asn Thr Asp Ala Lys Phe Gln Val Phe Leu
             115                 120                 125

AAG CAG ATC AAC AGC TCC CTG GTG GAC TCC AAC ATG CTG GTG CGC TGT         430
Lys Gln Ile Asn Ser Ser Leu Val Asp Ser Asn Met Leu Val Arg Cys
         130                 135                 140

GTC ACT CTG TCC CTG GAC CGA TTT GAA AAC CAG GTG GAT ATG AAA GTT         478
Val Thr Leu Ser Leu Asp Arg Phe Glu Asn Gln Val Asp Met Lys Val
     145                 150                 155

GCC GAG GTA CTG TCT GAA TGC CGC CTG CTC GCC TAC ATA TCC CAG GTG         526
Ala Glu Val Leu Ser Glu Cys Arg Leu Leu Ala Tyr Ile Ser Gln Val
160                 165                 170                 175

CCC ACG CAG ATG TCC TTC CTC TTC CGC CTC ATC AAC ATC ATC CAC GTG         574
Pro Thr Gln Met Ser Phe Leu Phe Arg Leu Ile Asn Ile Ile His Val
                 180                 185                 190

CAG ACG CTG ACC CAG GAG AAC GTC AGC TGC CTC AAC ACC AGC CTG GTG         622
Gln Thr Leu Thr Gln Glu Asn Val Ser Cys Leu Asn Thr Ser Leu Val
             195                 200                 205

ATC CTG ATG CTG GCC CGA CGG AAA GAG CGG CTG CCC CTG TAC CTG CGG         670
Ile Leu Met Leu Ala Arg Arg Lys Glu Arg Leu Pro Leu Tyr Leu Arg
         210                 215                 220

CTG CTG CAG CGG ATG GAG CAC AGC AAG AAG TAC CCC GGC TTC CTG CTC         718
Leu Leu Gln Arg Met Glu His Ser Lys Lys Tyr Pro Gly Phe Leu Leu
     225                 230                 235

AAC AAC TTC CAC AAC CTG CTG CGC TTC TGG CAG CAG CAC TAC CTG CAC         766
Asn Asn Phe His Asn Leu Leu Arg Phe Trp Gln Gln His Tyr Leu His
240                 245                 250                 255

AAG GAC AAG GAC AGC ACC TGC CTA GAG AAC AGC TCC TGC ATC AGC TTC         814
Lys Asp Lys Asp Ser Thr Cys Leu Glu Asn Ser Ser Cys Ile Ser Phe
                 260                 265                 270

TCA TAC TGG AAG GAG ACA GTG TCC ATC CTG TTG AAC CCG GAC CGG CAG         862
Ser Tyr Trp Lys Glu Thr Val Ser Ile Leu Leu Asn Pro Asp Arg Gln
             275                 280                 285

TCA CCC TCT GCT CTC GTT AGC TAC ATT GAG GAG CCC TAC ATG GAC ATA         910
Ser Pro Ser Ala Leu Val Ser Tyr Ile Glu Glu Pro Tyr Met Asp Ile
         290                 295                 300
```

```
GAC  AGG  GAC  TTC  ACT  GAG  GAG  TGACCTTGGG  CCAGGCCTCG  GGAGGCTGCT         961
Asp  Arg  Asp  Phe  Thr  Glu  Glu
          305                 310

GGGCCAGTGT  GGGTGAGCGT  GGGTACGATG  CCACACGCCC  TGCCCTGTTC  CCGTTCCTCC        1021

CTGCTGCTCT  CTGCCTGCCC  CAGGTCTTTG  GGTACAGGCT  TGGTGGGAGG  GAAGTCCTAG        1081

AAGCCCTTGG  TCCCCCTGGG  TCTGAGGGCC  CTAGGTCATG  GAGAGCCTCA  GTCCCCATAA        1141

TGAGGACAGG  GTACCATGCC  CACCTTTCCT  TCAGAACCCT  GGGGCCCAGG  GCCACCCAGA        1201

GGTAAGAGGA  CATTTAGCAT  TAGCTCTGTG  TGAGCTCCTG  CCGGTTTCTT  GGCTGTCAGT        1261

CAGTCCCAGA  GTGGGGAGGA  AGATATGGGT  GACCCCCACC  CCCCATCTGT  GAGCCAAGCC        1321

TCCCTTGTCC  CTGGCCTTTG  GACCCAGGCA  AAGGCTTCTG  AGCCCTGGGC  AGGGTGGTG        1381

GGTACCAGAG  AATGCTGCCT  TCCCCCAAGC  CTGCCCCTCT  GCCTCATTTT  CCTGTAGCTC        1441

CTCTGGTTCT  GTTTGCTCAT  TGGCCGCTGT  GTTCATCCAA  GGGGGTTCTC  CCAGAAGTGA        1501

GGGGCCTTTC  CCTCCATCCC  TTGGGGCACG  GGGCAGCTGT  GCCTGCCCTG  CCTCTGCCTG        1561

AGGCAGCCGC  TCCTGCCTGA  GCCTGGACAT  GGGGCCCTTC  CTTGTGTTGC  CAATTTATTA        1621

ACAGCAAATA  AACCAATTAA  ATGGAGACTA  TTAAATAACT  TTATTTAAA  AATGAAAAAA        1681

AAAAAAAAAA  AAA                                                              1694
```

( 2 ) INFORMATION FOR SEQ ID NO:10:

( i ) SEQUENCE CHARACTERISTICS:
        ( A ) LENGTH: 310 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Ser  Leu  Lys  Ala  Asn  Ile  Pro  Glu  Val  Glu  Ala  Val  Leu  Asn  Thr  Asp
 1                   5                        10                       15

Arg  Ser  Leu  Val  Cys  Asp  Gly  Lys  Arg  Gly  Leu  Leu  Thr  Arg  Leu  Leu
               20                  25                       30

Gln  Val  Met  Lys  Lys  Glu  Pro  Ala  Glu  Ser  Ser  Phe  Arg  Phe  Trp  Gln
          35                       40                       45

Ala  Arg  Ala  Val  Glu  Ser  Phe  Leu  Arg  Gly  Thr  Thr  Ser  Tyr  Ala  Asp
     50                       55                       60

Gln  Met  Phe  Leu  Leu  Lys  Arg  Gly  Leu  Leu  Glu  His  Ile  Leu  Tyr  Cys
65                       70                       75                       80

Ile  Val  Asp  Ser  Glu  Cys  Lys  Ser  Arg  Asp  Val  Leu  Gln  Ser  Tyr  Phe
                    85                       90                       95

Asp  Leu  Leu  Gly  Glu  Leu  Met  Lys  Phe  Asn  Val  Asp  Ala  Phe  Lys  Arg
               100                      105                      110

Phe  Asn  Lys  Tyr  Ile  Asn  Thr  Asp  Ala  Lys  Phe  Gln  Val  Phe  Leu  Lys
          115                      120                      125

Gln  Ile  Asn  Ser  Ser  Leu  Val  Asp  Ser  Asn  Met  Leu  Val  Arg  Cys  Val
     130                      135                      140

Thr  Leu  Ser  Leu  Asp  Arg  Phe  Glu  Asn  Gln  Val  Asp  Met  Lys  Val  Ala
145                      150                      155                      160

Glu  Val  Leu  Ser  Glu  Cys  Arg  Leu  Leu  Ala  Tyr  Ile  Ser  Gln  Val  Pro
                    165                      170                      175

Thr  Gln  Met  Ser  Phe  Leu  Phe  Arg  Leu  Ile  Asn  Ile  Ile  His  Val  Gln
               180                      185                      190

Thr  Leu  Thr  Gln  Glu  Asn  Val  Ser  Cys  Leu  Asn  Thr  Ser  Leu  Val  Ile
          195                      200                      205
```

| | | | | | | | | | | | | | | | |
|---|---|---|---|---|---|---|---|---|---|---|---|---|---|---|---|
| Leu | Met | Leu | Ala | Arg | Arg | Lys | Glu | Arg | Leu | Pro | Leu | Tyr | Leu | Arg | Leu |
| | 210 | | | | | 215 | | | | 220 | | | | | |
| Leu | Gln | Arg | Met | Glu | His | Ser | Lys | Lys | Tyr | Pro | Gly | Phe | Leu | Leu | Asn |
| 225 | | | | | 230 | | | | | 235 | | | | | 240 |
| Asn | Phe | His | Asn | Leu | Leu | Arg | Phe | Trp | Gln | Gln | His | Tyr | Leu | His | Lys |
| | | | | 245 | | | | | 250 | | | | | 255 | |
| Asp | Lys | Asp | Ser | Thr | Cys | Leu | Glu | Asn | Ser | Ser | Cys | Ile | Ser | Phe | Ser |
| | | | 260 | | | | | 265 | | | | | 270 | | |
| Tyr | Trp | Lys | Glu | Thr | Val | Ser | Ile | Leu | Leu | Asn | Pro | Asp | Arg | Gln | Ser |
| | | 275 | | | | | 280 | | | | | 285 | | | |
| Pro | Ser | Ala | Leu | Val | Ser | Tyr | Ile | Glu | Glu | Pro | Tyr | Met | Asp | Ile | Asp |
| | | 290 | | | | | 295 | | | | | 300 | | | |
| Arg | Asp | Phe | Thr | Glu | Glu | | | | | | | | | | |
| 305 | | | | | 310 | | | | | | | | | | |

(2) INFORMATION FOR SEQ ID NO:11:

(i) SEQUENCE CHARACTERISTICS:
        (A) LENGTH: 2735 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 2..1822

(xi) SEQUENCE DESCRIPTION: SEQ ID NO:11:

| | | | | | | | | | | | | | | | | | |
|---|---|---|---|---|---|---|---|---|---|---|---|---|---|---|---|---|---|
| G | GAG | ATC | AGT | CGG | AAG | GTG | TAC | AAG | GGA | ATG | TTA | GAC | CTC | CTC | AAG | | 46 |
| | Glu | Ile | Ser | Arg | Lys | Val | Tyr | Lys | Gly | Met | Leu | Asp | Leu | Leu | Lys | | |
| | 1 | | | | 5 | | | | | 10 | | | | | 15 | | |
| TGT | ACA | GTC | CTC | AGC | TTG | GAG | CAG | TCC | TAT | GCC | CAC | GCG | GGT | CTG | GGT | | 94 |
| Cys | Thr | Val | Leu | Ser | Leu | Glu | Gln | Ser | Tyr | Ala | His | Ala | Gly | Leu | Gly | | |
| | | | | 20 | | | | | 25 | | | | | 30 | | | |
| GGC | ATG | GCC | AGC | ATC | TTT | GGG | CTT | TTG | GAG | ATT | GCC | CAG | ACC | CAC | TAC | | 142 |
| Gly | Met | Ala | Ser | Ile | Phe | Gly | Leu | Leu | Glu | Ile | Ala | Gln | Thr | His | Tyr | | |
| | | | 35 | | | | | 40 | | | | | 45 | | | | |
| TAT | AGT | AAA | GAA | CCA | GAC | AAG | CGG | AAG | AGA | AGT | CCA | ACA | GAA | AGT | GTA | | 190 |
| Tyr | Ser | Lys | Glu | Pro | Asp | Lys | Arg | Lys | Arg | Ser | Pro | Thr | Glu | Ser | Val | | |
| | | 50 | | | | | 55 | | | | | 60 | | | | | |
| AAT | ACC | CCA | GTT | GGC | AAG | GAT | CCT | GGC | CTA | GCT | GGG | CGG | GGG | GAC | CCA | | 238 |
| Asn | Thr | Pro | Val | Gly | Lys | Asp | Pro | Gly | Leu | Ala | Gly | Arg | Gly | Asp | Pro | | |
| | 65 | | | | | 70 | | | | | 75 | | | | | | |
| AAG | GCT | ATG | GCA | CAA | CTG | AGA | GTT | CCA | CAA | CTG | GGA | CCT | CGG | GCA | CCA | | 286 |
| Lys | Ala | Met | Ala | Gln | Leu | Arg | Val | Pro | Gln | Leu | Gly | Pro | Arg | Ala | Pro | | |
| 80 | | | | | 85 | | | | | 90 | | | | | 95 | | |
| AGT | GCC | ACA | GGA | AAG | GGT | CCT | AAG | GAA | CTG | GAC | ACC | AGA | AGT | TTA | AAG | | 334 |
| Ser | Ala | Thr | Gly | Lys | Gly | Pro | Lys | Glu | Leu | Asp | Thr | Arg | Ser | Leu | Lys | | |
| | | | 100 | | | | | 105 | | | | | 110 | | | | |
| GAA | GAA | AAT | TTT | ATA | GCA | TCT | ATT | GGG | CCT | GAA | GTA | ATC | AAA | CCT | GTC | | 382 |
| Glu | Glu | Asn | Phe | Ile | Ala | Ser | Ile | Gly | Pro | Glu | Val | Ile | Lys | Pro | Val | | |
| | | | 115 | | | | | 120 | | | | | 125 | | | | |
| TTT | GAC | CTT | GGT | GAG | ACA | GAG | GAG | AAA | AAG | TCC | CAG | ATC | AGC | GCA | GAC | | 430 |
| Phe | Asp | Leu | Gly | Glu | Thr | Glu | Glu | Lys | Lys | Ser | Gln | Ile | Ser | Ala | Asp | | |
| | | 130 | | | | | 135 | | | | | 140 | | | | | |
| AGT | GGT | GTG | AGC | CTG | ACG | TCT | AGT | TCC | CAG | AGG | ACT | GAT | CAA | GAC | TCT | | 478 |
| Ser | Gly | Val | Ser | Leu | Thr | Ser | Ser | Ser | Gln | Arg | Thr | Asp | Gln | Asp | Ser | | |
| | 145 | | | | | 150 | | | | | 155 | | | | | | |

| | | | | | | | | | | | | | | | | |
|---|---|---|---|---|---|---|---|---|---|---|---|---|---|---|---|---|
| GTC | ATC | GGC | GTG | AGT | CCA | GCT | GTT | ATG | ATC | CGC | AGC | TCA | AGT | CAG | GAT | 526 |
| Val | Ile | Gly | Val | Ser | Pro | Ala | Val | Met | Ile | Arg | Ser | Ser | Ser | Gln | Asp | |
| 160 | | | | | 165 | | | | 170 | | | | | | 175 | |
| TCT | GAA | GTT | AGC | ACC | GTG | GTG | AGT | AAT | AGC | TCT | GGA | GAG | ACC | CTT | GGA | 574 |
| Ser | Glu | Val | Ser | Thr | Val | Val | Ser | Asn | Ser | Ser | Gly | Glu | Thr | Leu | Gly | |
| | | | | 180 | | | | | 185 | | | | | 190 | | |
| GCT | GAC | AGT | GAC | TTG | AGC | AGC | AAT | GCA | GGT | GAT | GGA | CCA | GGT | GGC | GAG | 622 |
| Ala | Asp | Ser | Asp | Leu | Ser | Ser | Asn | Ala | Gly | Asp | Gly | Pro | Gly | Gly | Glu | |
| | | | 195 | | | | | 200 | | | | | 205 | | | |
| GGC | AGT | GTT | CAC | CTG | GCA | AGC | TCT | CGG | GGC | ACT | TTG | TCT | GAT | AGT | GAA | 670 |
| Gly | Ser | Val | His | Leu | Ala | Ser | Ser | Arg | Gly | Thr | Leu | Ser | Asp | Ser | Glu | |
| | | 210 | | | | | 215 | | | | | 220 | | | | |
| ATT | GAG | ACC | AAC | TCT | GCC | ACA | AGC | ACC | ATC | TTT | GGT | AAA | GCC | CAC | AGC | 718 |
| Ile | Glu | Thr | Asn | Ser | Ala | Thr | Ser | Thr | Ile | Phe | Gly | Lys | Ala | His | Ser | |
| | 225 | | | | | 230 | | | | | 235 | | | | | |
| TTG | AAG | CCA | AGC | ATA | AAG | GAG | AAG | CTG | GCA | GGC | AGC | CCC | ATT | CGT | ACT | 766 |
| Leu | Lys | Pro | Ser | Ile | Lys | Glu | Lys | Leu | Ala | Gly | Ser | Pro | Ile | Arg | Thr | |
| 240 | | | | | 245 | | | | 250 | | | | | | 255 | |
| TCT | GAA | GAT | GTG | AGC | CAG | CGA | GTC | TAT | CTC | TAT | GAG | GGA | CTC | CTA | GGC | 814 |
| Ser | Glu | Asp | Val | Ser | Gln | Arg | Val | Tyr | Leu | Tyr | Glu | Gly | Leu | Leu | Gly | |
| | | | | 260 | | | | | 265 | | | | | 270 | | |
| AAA | GAG | CGT | TCT | ACT | TTA | TGG | GAC | CAA | ATG | CAA | TTC | TGG | GAA | GAT | GCC | 862 |
| Lys | Glu | Arg | Ser | Thr | Leu | Trp | Asp | Gln | Met | Gln | Phe | Trp | Glu | Asp | Ala | |
| | | | 275 | | | | | 280 | | | | | 285 | | | |
| TTC | TTA | GAT | GCT | GTG | ATG | TTG | GAG | AGA | GAA | GGG | ATG | GGT | ATG | GAC | CAG | 910 |
| Phe | Leu | Asp | Ala | Val | Met | Leu | Glu | Arg | Glu | Gly | Met | Gly | Met | Asp | Gln | |
| | | 290 | | | | | 295 | | | | | 300 | | | | |
| GGT | CCC | CAG | GAA | ATG | ATC | GAC | AGG | TAC | CTG | TCC | CTT | GGA | GAA | CAT | GAC | 958 |
| Gly | Pro | Gln | Glu | Met | Ile | Asp | Arg | Tyr | Leu | Ser | Leu | Gly | Glu | His | Asp | |
| | 305 | | | | | 310 | | | | | 315 | | | | | |
| CGG | AAG | CGC | CTG | GAA | GAT | GAT | GAA | GAT | CGC | TTG | CTG | GCC | ACA | CTT | CTG | 1006 |
| Arg | Lys | Arg | Leu | Glu | Asp | Asp | Glu | Asp | Arg | Leu | Leu | Ala | Thr | Leu | Leu | |
| 320 | | | | | 325 | | | | 330 | | | | | | 335 | |
| CAC | AAC | CTC | ATC | TCC | TAC | ATG | CTG | CTG | ATG | AAG | GTA | AAT | AAG | AAT | GAC | 1054 |
| His | Asn | Leu | Ile | Ser | Tyr | Met | Leu | Leu | Met | Lys | Val | Asn | Lys | Asn | Asp | |
| | | | | 340 | | | | | 345 | | | | | 350 | | |
| ATC | CGC | AAG | AAG | GTG | AGG | CGC | CTA | ATG | GGA | AAG | TCG | CAC | ATT | GGG | CTT | 1102 |
| Ile | Arg | Lys | Lys | Val | Arg | Arg | Leu | Met | Gly | Lys | Ser | His | Ile | Gly | Leu | |
| | | | 355 | | | | | 360 | | | | | 365 | | | |
| GTG | TAC | AGC | CAG | CAA | ATC | AAT | GAG | GTG | CTT | GAT | CAG | CTG | GCG | AAC | CTG | 1150 |
| Val | Tyr | Ser | Gln | Gln | Ile | Asn | Glu | Val | Leu | Asp | Gln | Leu | Ala | Asn | Leu | |
| | | 370 | | | | | 375 | | | | | 380 | | | | |
| AAT | GGA | CGC | GAT | CTC | TCT | ATC | TGG | TCC | AGT | GGC | AGC | CGG | CAC | ATG | AAG | 1198 |
| Asn | Gly | Arg | Asp | Leu | Ser | Ile | Trp | Ser | Ser | Gly | Ser | Arg | His | Met | Lys | |
| | 385 | | | | | 390 | | | | | 395 | | | | | |
| AAG | CAG | ACA | TTT | GTG | GTA | CAT | GCA | GGG | ACA | GAT | ACA | AAC | GGA | GAT | ATC | 1246 |
| Lys | Gln | Thr | Phe | Val | Val | His | Ala | Gly | Thr | Asp | Thr | Asn | Gly | Asp | Ile | |
| 400 | | | | | 405 | | | | 410 | | | | | | 415 | |
| TTT | TTC | ATG | GAG | GTG | TGC | GAT | GAC | TGT | GTG | GTG | TTG | CGT | AGT | AAC | ATC | 1294 |
| Phe | Phe | Met | Glu | Val | Cys | Asp | Asp | Cys | Val | Val | Leu | Arg | Ser | Asn | Ile | |
| | | | | 420 | | | | | 425 | | | | | 430 | | |
| GGA | ACA | GTG | TAT | GAG | CGC | TGG | TGG | TAC | GAG | AAG | CTC | ATC | AAC | ATG | ACC | 1342 |
| Gly | Thr | Val | Tyr | Glu | Arg | Trp | Trp | Tyr | Glu | Lys | Leu | Ile | Asn | Met | Thr | |
| | | | 435 | | | | | 440 | | | | | 445 | | | |
| TAC | TGT | CCC | AAG | ACG | AAG | GTG | TTG | TGC | TTG | TGG | CGT | AGA | AAT | GGC | TCT | 1390 |
| Tyr | Cys | Pro | Lys | Thr | Lys | Val | Leu | Cys | Leu | Trp | Arg | Arg | Asn | Gly | Ser | |
| | | 450 | | | | | 455 | | | | | 460 | | | | |
| GAG | ACC | CAG | CTC | AAC | AAG | TTC | TAT | ACT | AAA | AAG | TGT | CGG | GAG | CTG | TAC | 1438 |
| Glu | Thr | Gln | Leu | Asn | Lys | Phe | Tyr | Thr | Lys | Lys | Cys | Arg | Glu | Leu | Tyr | |
| | 465 | | | | | 470 | | | | | 475 | | | | | |

| | | | | | | | | | | | | | | | |
|---|---|---|---|---|---|---|---|---|---|---|---|---|---|---|---|
|TAC|TGT|GTG|AAG|GAC|AGC|ATG|GAG|CGC|GCT|GCC|GCC|CGA|CAG|CAA|AGC|
|Tyr|Cys|Val|Lys|Asp|Ser|Met|Glu|Arg|Ala|Ala|Ala|Arg|Gln|Gln|Ser|
|480| | | | |485| | | |490| | | | | |495|

1486

| | | | | | | | | | | | | | | | |
|---|---|---|---|---|---|---|---|---|---|---|---|---|---|---|---|
|ATC|AAA|CCC|GGA|CCT|GAA|TTG|GGT|GGC|GAG|TTC|CCT|GTG|CAG|GAC|CTG|
|Ile|Lys|Pro|Gly|Pro|Glu|Leu|Gly|Gly|Glu|Phe|Pro|Val|Gln|Asp|Leu|
| | | | |500| | | | |505| | | | |510| |

1534

| | | | | | | | | | | | | | | | |
|---|---|---|---|---|---|---|---|---|---|---|---|---|---|---|---|
|AAG|ACT|GGT|GAG|GGT|GGC|CTG|CTG|CAG|GTG|ACC|CTG|GAA|GGG|ATC|AAC|
|Lys|Thr|Gly|Glu|Gly|Gly|Leu|Leu|Gln|Val|Thr|Leu|Glu|Gly|Ile|Asn|
| | | | |515| | | | |520| | | | |525| |

1582

| | | | | | | | | | | | | | | | |
|---|---|---|---|---|---|---|---|---|---|---|---|---|---|---|---|
|CTC|AAA|TTC|ATG|CAC|AAT|CAG|GTT|TTC|ATA|GAG|CTG|AAT|CAC|ATT|AAA|
|Leu|Lys|Phe|Met|His|Asn|Gln|Val|Phe|Ile|Glu|Leu|Asn|His|Ile|Lys|
| | | |530| | | | |535| | | | |540| | |

1630

| | | | | | | | | | | | | | | | |
|---|---|---|---|---|---|---|---|---|---|---|---|---|---|---|---|
|AAG|TGC|AAT|ACA|GTT|CGA|GGC|GTC|TTT|GTC|CTG|GAG|GAA|TTT|GTT|CCT|
|Lys|Cys|Asn|Thr|Val|Arg|Gly|Val|Phe|Val|Leu|Glu|Glu|Phe|Val|Pro|
| |545| | | | |550| | | | |555| | | | |

1678

| | | | | | | | | | | | | | | | |
|---|---|---|---|---|---|---|---|---|---|---|---|---|---|---|---|
|GAA|ATT|AAA|GAA|GTG|GTG|AGC|CAC|AAG|TAC|AAG|ACA|CCA|ATG|GCC|CAC|
|Glu|Ile|Lys|Glu|Val|Val|Ser|His|Lys|Tyr|Lys|Thr|Pro|Met|Ala|His|
|560| | | | |565| | | | |570| | | | |575|

1726

| | | | | | | | | | | | | | | | |
|---|---|---|---|---|---|---|---|---|---|---|---|---|---|---|---|
|GAA|ATC|TGC|TAC|TCC|GTA|TTA|TGT|CTC|TTC|TCG|TAC|GTG|GCT|GCA|GTT|
|Glu|Ile|Cys|Tyr|Ser|Val|Leu|Cys|Leu|Phe|Ser|Tyr|Val|Ala|Ala|Val|
| | | | |580| | | | |585| | | | |590| |

1774

| | | | | | | | | | | | | | | | |
|---|---|---|---|---|---|---|---|---|---|---|---|---|---|---|---|
|CAT|AGC|AGT|GAG|GAA|GAT|CTC|AGA|ACC|CCG|CCC|CGG|CCT|GTC|TCT|AGC|
|His|Ser|Ser|Glu|Glu|Asp|Leu|Arg|Thr|Pro|Pro|Arg|Pro|Val|Ser|Ser|
| | | |595| | | | |600| | | | |605| | |

1822

| | | | | |
|---|---|---|---|---|
|TGATGGAGAG|GGGCTACGCA|GCTGCCCCAG|CCCAGGGCAC|GCCCCTGGCC|CCTTGCTGTT|

1882

| | | | | |
|---|---|---|---|---|
|CCCAAGTGCA|CGATGCTGCT|GTGACTGAGG|AGTGGATGAT|GCTCGTGTGT|CCTCTGCAAG|

1942

| | | | | |
|---|---|---|---|---|
|CCCCCTGCTG|TGGCTTGGTT|GGTTACCGGT|TATGTGTCCC|TCTGAGTGTG|TCTTGAGCGT|

2002

| | | | | |
|---|---|---|---|---|
|GTCCACCTTC|TCCCTCTCCA|CTCCCAGAAG|ACCAAACTGC|CTTCCCCTCA|GGGCTCAAGA|

2062

| | | | | |
|---|---|---|---|---|
|ATGTGTACAG|TCTGTGGGGC|CGGTGTGAAC|CCACTATTTT|GTGTCCTTGA|GACATTTGTG|

2122

| | | | | |
|---|---|---|---|---|
|TTGTGGTTCC|TTGTCCTTGT|CCCTGGCGTT|ATAACTGTCC|ACTGCAAGAG|TCTGGCTCTC|

2182

| | | | | |
|---|---|---|---|---|
|CCTTCTCTGT|GACCCGGCAT|GACTGGGCGC|CTGGAGCAGT|TTCACTCTGT|GAGGAGTGAG|

2242

| | | | | |
|---|---|---|---|---|
|GGAACCCTGG|GGCTCACCCT|CTCAGAGGAA|GGGCACAGAG|AGGAAGGGAA|GAATTGGGGG|

2302

| | | | | |
|---|---|---|---|---|
|GCAGCCGGAG|TGAGTGGCAG|CCTCCCTGCT|TCCTTCTGCA|TTCCCAAGCC|GGCAGCTACT|

2362

| | | | | |
|---|---|---|---|---|
|GCCCAGGGCC|CGCAGTGTTG|GCTGCTGCCT|GCCACAGCCT|CTGTGACTGC|AGTGGAGCGG|

2422

| | | | | |
|---|---|---|---|---|
|CGAATTCCCT|GTGGCCTGCC|ACGCCTTCGG|CATCAGAGGA|TGGAGTGGTC|GAGGCTAGTG|

2482

| | | | | |
|---|---|---|---|---|
|GAGTCCCAGG|GACCGCTGGC|TGCTCTGCCT|GAGCATCAGG|GAGGGGGCAG|GAAAGACCAA|

2542

| | | | | |
|---|---|---|---|---|
|GCTGGGTTTG|CACATCTGTC|TGCAGGCTGT|CTCTCCAGGC|ACGGGGTGTC|AGGAGGGAGA|

2602

| | | | | |
|---|---|---|---|---|
|GACAGCCTGG|GTATGGGCAA|GAAATGACTG|TAAATATTTC|AGCCCCACAT|TATTTATAGA|

2662

| | | | | |
|---|---|---|---|---|
|AAATGTACAG|TTGTGTGAAT|GTGAAATAAA|TGTCCTCAAC|TCCCAAAAAA|AAAAAAAAA|

2722

AAAAAAAAAA AAA

2735

( 2 ) INFORMATION FOR SEQ ID NO:12:

( i ) SEQUENCE CHARACTERISTICS:
        ( A ) LENGTH: 607 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| | | | | | | | | | | | | | | | |
|---|---|---|---|---|---|---|---|---|---|---|---|---|---|---|---|
|Glu|Ile|Ser|Arg|Lys|Val|Tyr|Lys|Gly|Met|Leu|Asp|Leu|Leu|Lys|Cys|
|1| | | |5| | | | |10| | | | |15| |

```
Thr  Val  Leu  Ser  Leu  Glu  Gln  Ser  Tyr  Ala  His  Ala  Gly  Leu  Gly  Gly
          20                      25                      30

Met  Ala  Ser  Ile  Phe  Gly  Leu  Leu  Glu  Ile  Ala  Gln  Thr  His  Tyr  Tyr
               35                      40                      45

Ser  Lys  Glu  Pro  Asp  Lys  Arg  Lys  Arg  Ser  Pro  Thr  Glu  Ser  Val  Asn
          50                      55                      60

Thr  Pro  Val  Gly  Lys  Asp  Pro  Gly  Leu  Ala  Gly  Arg  Gly  Asp  Pro  Lys
65                            70                      75                     80

Ala  Met  Ala  Gln  Leu  Arg  Val  Pro  Gln  Leu  Gly  Pro  Arg  Ala  Pro  Ser
                    85                      90                           95

Ala  Thr  Gly  Lys  Gly  Pro  Lys  Glu  Leu  Asp  Thr  Arg  Ser  Leu  Lys  Glu
                    100                     105                     110

Glu  Asn  Phe  Ile  Ala  Ser  Ile  Gly  Pro  Glu  Val  Ile  Lys  Pro  Val  Phe
               115                     120                     125

Asp  Leu  Gly  Glu  Thr  Glu  Lys  Lys  Ser  Gln  Ile  Ser  Ala  Asp  Ser
          130                     135                     140

Gly  Val  Ser  Leu  Thr  Ser  Ser  Ser  Gln  Arg  Thr  Asp  Gln  Asp  Ser  Val
145                      150                     155                          160

Ile  Gly  Val  Ser  Pro  Ala  Val  Met  Ile  Arg  Ser  Ser  Ser  Gln  Asp  Ser
                    165                     170                     175

Glu  Val  Ser  Thr  Val  Val  Ser  Asn  Ser  Ser  Gly  Glu  Thr  Leu  Gly  Ala
               180                     185                     190

Asp  Ser  Asp  Leu  Ser  Ser  Asn  Ala  Gly  Asp  Gly  Pro  Gly  Gly  Glu  Gly
               195                     200                     205

Ser  Val  His  Leu  Ala  Ser  Ser  Arg  Gly  Thr  Leu  Ser  Asp  Ser  Glu  Ile
          210                     215                     220

Glu  Thr  Asn  Ser  Ala  Thr  Ser  Thr  Ile  Phe  Gly  Lys  Ala  His  Ser  Leu
225                           230                     235                     240

Lys  Pro  Ser  Ile  Lys  Glu  Lys  Leu  Ala  Gly  Ser  Pro  Ile  Arg  Thr  Ser
                    245                     250                     255

Glu  Asp  Val  Ser  Gln  Arg  Val  Tyr  Leu  Tyr  Glu  Gly  Leu  Leu  Gly  Lys
               260                     265                     270

Glu  Arg  Ser  Thr  Leu  Trp  Asp  Gln  Met  Gln  Phe  Trp  Glu  Asp  Ala  Phe
               275                     280                     285

Leu  Asp  Ala  Val  Met  Leu  Glu  Arg  Glu  Gly  Met  Gly  Met  Asp  Gln  Gly
     290                     295                     300

Pro  Gln  Glu  Met  Ile  Asp  Arg  Tyr  Leu  Ser  Leu  Gly  Glu  His  Asp  Arg
305                      310                     315                          320

Lys  Arg  Leu  Glu  Asp  Asp  Glu  Asp  Arg  Leu  Leu  Ala  Thr  Leu  Leu  His
                         325                     330                     335

Asn  Leu  Ile  Ser  Tyr  Met  Leu  Leu  Met  Lys  Val  Asn  Lys  Asn  Asp  Ile
               340                     345                     350

Arg  Lys  Lys  Val  Arg  Arg  Leu  Met  Gly  Lys  Ser  His  Ile  Gly  Leu  Val
          355                     360                     365

Tyr  Ser  Gln  Gln  Ile  Asn  Glu  Val  Leu  Asp  Gln  Leu  Ala  Asn  Leu  Asn
     370                     375                     380

Gly  Arg  Asp  Leu  Ser  Ile  Trp  Ser  Ser  Gly  Ser  Arg  His  Met  Lys  Lys
385                      390                     395                          400

Gln  Thr  Phe  Val  Val  His  Ala  Gly  Thr  Asp  Thr  Asn  Gly  Asp  Ile  Phe
                    405                     410                     415

Phe  Met  Glu  Val  Cys  Asp  Asp  Cys  Val  Val  Leu  Arg  Ser  Asn  Ile  Gly
                    420                     425                     430

Thr  Val  Tyr  Glu  Arg  Trp  Trp  Tyr  Glu  Lys  Leu  Ile  Asn  Met  Thr  Tyr
               435                     440                     445
```

```
Cys  Pro  Lys  Thr  Lys  Val  Leu  Cys  Leu  Trp  Arg  Arg  Asn  Gly  Ser  Glu
     450                 455                      460

Thr  Gln  Leu  Asn  Lys  Phe  Tyr  Thr  Lys  Lys  Cys  Arg  Glu  Leu  Tyr  Tyr
465                      470                 475                           480

Cys  Val  Lys  Asp  Ser  Met  Glu  Arg  Ala  Ala  Arg  Gln  Gln  Ser  Ile
                    485                 490                      495

Lys  Pro  Gly  Pro  Glu  Leu  Gly  Gly  Glu  Phe  Pro  Val  Gln  Asp  Leu  Lys
               500                 505                           510

Thr  Gly  Glu  Gly  Gly  Leu  Leu  Gln  Val  Thr  Leu  Glu  Gly  Ile  Asn  Leu
               515                 520                           525

Lys  Phe  Met  His  Asn  Gln  Val  Phe  Ile  Glu  Leu  Asn  His  Ile  Lys  Lys
     530                 535                      540

Cys  Asn  Thr  Val  Arg  Gly  Val  Phe  Val  Leu  Glu  Glu  Phe  Val  Pro  Glu
545                      550                 555                           560

Ile  Lys  Glu  Val  Val  Ser  His  Lys  Tyr  Lys  Thr  Pro  Met  Ala  His  Glu
                    565                 570                      575

Ile  Cys  Tyr  Ser  Val  Leu  Cys  Leu  Phe  Ser  Tyr  Val  Ala  Ala  Val  His
                    580                 585                      590

Ser  Ser  Glu  Glu  Asp  Leu  Arg  Thr  Pro  Pro  Arg  Pro  Val  Ser  Ser
               595                 600                      605
```

(2) INFORMATION FOR SEQ ID NO:13:

(i) SEQUENCE CHARACTERISTICS:
        (A) LENGTH: 3225 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 3..2846

(xi) SEQUENCE DESCRIPTION: SEQ ID NO:13:

```
CC  CAG  ACT  CGC  CCC  GCC  CCA  GAG  ACT  GCG  CCT  GCG  CGG  GCA  CGA  GAC       47
    Gln  Thr  Arg  Pro  Ala  Pro  Glu  Thr  Ala  Pro  Ala  Arg  Ala  Arg  Asp
    1                   5                        10                      15

ACC  CTC  TCC  GCG  ATG  ACT  GCC  AGC  TCA  GTG  GAG  CAG  CTG  CGG  AAG  GAG       95
Thr  Leu  Ser  Ala  Met  Thr  Ala  Ser  Ser  Val  Glu  Gln  Leu  Arg  Lys  Glu
                    20                   25                           30

GGC  AAT  GAG  CTG  TTC  AAA  TGT  GGA  GAC  TAC  GGG  GGC  GCC  CTG  GCG  GCC      143
Gly  Asn  Glu  Leu  Phe  Lys  Cys  Gly  Asp  Tyr  Gly  Gly  Ala  Leu  Ala  Ala
               35                   40                           45

TAC  ACT  CAG  GCC  CTG  GGT  CTG  GAC  GCG  ACG  CCC  CAG  GAC  CAG  GCC  GTT      191
Tyr  Thr  Gln  Ala  Leu  Gly  Leu  Asp  Ala  Thr  Pro  Gln  Asp  Gln  Ala  Val
               50                   55                           60

CTG  CAC  CGG  AAC  CGG  GCC  GCC  TGC  CAC  CTC  AAG  CTG  GAA  GAT  TAC  GAC      239
Leu  His  Arg  Asn  Arg  Ala  Ala  Cys  His  Leu  Lys  Leu  Glu  Asp  Tyr  Asp
     65                       70                      75

AAA  GCA  GAA  ACA  GAG  GCA  TCC  AAA  GCC  ATT  GAA  AAG  GAT  GGT  GGG  GAT      287
Lys  Ala  Glu  Thr  Glu  Ala  Ser  Lys  Ala  Ile  Glu  Lys  Asp  Gly  Gly  Asp
80                        85                       90                      95

GTC  AAA  GCA  CTC  TAC  CGG  CGG  AGC  CAA  GCC  CTA  GAG  AAG  CTG  GGC  CGC      335
Val  Lys  Ala  Leu  Tyr  Arg  Arg  Ser  Gln  Ala  Leu  Glu  Lys  Leu  Gly  Arg
                    100                  105                         110

CTG  GAC  CAG  GCT  GTC  CTT  GAC  CTG  CAG  AGA  TGT  GTG  AGC  TTG  GAG  CCC      383
Leu  Asp  Gln  Ala  Val  Leu  Asp  Leu  Gln  Arg  Cys  Val  Ser  Leu  Glu  Pro
```

-continued

```
                        115                              120                              125
AAG  AAC  AAA  GTT  TTC  CAG  GAG  GCC  TTG  CGG  AAC  ATC  GGG  GGC  CAG  ATT       431
Lys  Asn  Lys  Val  Phe  Gln  Glu  Ala  Leu  Arg  Asn  Ile  Gly  Gly  Gln  Ile
               130                      135                      140

CAG  GAG  AAG  GTG  CGA  TAC  ATG  TCC  TCG  ACG  GAT  GCC  AAA  GTG  GAA  CAG       479
Gln  Glu  Lys  Val  Arg  Tyr  Met  Ser  Ser  Thr  Asp  Ala  Lys  Val  Glu  Gln
          145                      150                      155

ATG  TTT  CAG  ATA  CTG  TTG  GAC  CCA  GAA  GAG  AAG  GGC  ACT  GAG  AAA  AAG       527
Met  Phe  Gln  Ile  Leu  Leu  Asp  Pro  Glu  Glu  Lys  Gly  Thr  Glu  Lys  Lys
160                      165                      170                      175

CAA  AAG  GCT  TCT  CAG  AAC  CTG  GTG  GTG  CTG  GCC  AGG  GAG  GAT  GCT  GGA       575
Gln  Lys  Ala  Ser  Gln  Asn  Leu  Val  Val  Leu  Ala  Arg  Glu  Asp  Ala  Gly
                    180                      185                      190

GCG  GAG  AAG  ATC  TTC  CGG  AGT  AAT  GGG  GTT  CAG  CTC  TTG  CAA  CGT  TTA       623
Ala  Glu  Lys  Ile  Phe  Arg  Ser  Asn  Gly  Val  Gln  Leu  Leu  Gln  Arg  Leu
               195                      200                      205

CTG  GAC  ATG  GGA  GAG  ACT  GAC  CTC  ATG  CTG  GCG  GCT  CTG  CGT  ACG  CTG       671
Leu  Asp  Met  Gly  Glu  Thr  Asp  Leu  Met  Leu  Ala  Ala  Leu  Arg  Thr  Leu
          210                      215                      220

GTT  GGC  ATT  TGC  TCT  GAG  CAT  CAG  TCA  CGG  ACA  GTG  GCA  ACC  CTG  AGC       719
Val  Gly  Ile  Cys  Ser  Glu  His  Gln  Ser  Arg  Thr  Val  Ala  Thr  Leu  Ser
     225                      230                      235

ATA  CTG  GGA  ACT  CGG  CGA  GTA  GTC  TCC  ATC  CTG  GGC  GTG  GAA  AGC  CAG       767
Ile  Leu  Gly  Thr  Arg  Arg  Val  Val  Ser  Ile  Leu  Gly  Val  Glu  Ser  Gln
240                      245                      250                      255

GCT  GTG  TCC  CTG  GCT  GCC  TGC  CAC  CTG  CTG  CAG  GTT  ATG  TTT  GAT  GCC       815
Ala  Val  Ser  Leu  Ala  Ala  Cys  His  Leu  Leu  Gln  Val  Met  Phe  Asp  Ala
                    260                      265                      270

CTC  AAG  GAA  GGT  GTC  AAA  AAA  GGC  TTC  CGA  GGC  AAA  GAA  GGT  GCC  ATC       863
Leu  Lys  Glu  Gly  Val  Lys  Lys  Gly  Phe  Arg  Gly  Lys  Glu  Gly  Ala  Ile
               275                      280                      285

ATT  GTG  GAT  CCT  GCC  CGG  GAG  CTG  AAG  GTC  CTC  ATC  AGT  AAC  CTC  TTA       911
Ile  Val  Asp  Pro  Ala  Arg  Glu  Leu  Lys  Val  Leu  Ile  Ser  Asn  Leu  Leu
          290                      295                      300

GAT  CTG  CTG  ACA  GAG  GTG  GGG  GTC  TCT  GGC  CAA  GGC  CGA  GAC  AAT  GCC       959
Asp  Leu  Leu  Thr  Glu  Val  Gly  Val  Ser  Gly  Gln  Gly  Arg  Asp  Asn  Ala
     305                      310                      315

CTG  ACC  CTC  CTG  ATT  AAA  GCG  GTG  CCC  CGG  AAG  TCT  CTC  AAG  GAC  CCC      1007
Leu  Thr  Leu  Leu  Ile  Lys  Ala  Val  Pro  Arg  Lys  Ser  Leu  Lys  Asp  Pro
320                      325                      330                      335

AAC  AAC  AGC  CTC  ACC  CTC  TGG  GTC  ATC  GAC  CAA  GGT  CTG  AAA  AAG  ATT      1055
Asn  Asn  Ser  Leu  Thr  Leu  Trp  Val  Ile  Asp  Gln  Gly  Leu  Lys  Lys  Ile
                    340                      345                      350

TTG  GAA  GTG  GGG  GGC  TCT  CTA  CAG  GAC  CCT  CCT  GGG  GAG  CTC  GCA  GTG      1103
Leu  Glu  Val  Gly  Gly  Ser  Leu  Gln  Asp  Pro  Pro  Gly  Glu  Leu  Ala  Val
               355                      360                      365

ACC  GCA  AAC  AGC  CGC  ATG  AGC  GCC  TCT  ATT  CTC  CTC  AGC  AAG  CTC  TTT      1151
Thr  Ala  Asn  Ser  Arg  Met  Ser  Ala  Ser  Ile  Leu  Leu  Ser  Lys  Leu  Phe
          370                      375                      380

GAT  GAC  CTC  AAG  TGT  GAT  GCG  GAG  AGG  GAG  AAT  TTC  CAC  AGA  CTT  TGT      1199
Asp  Asp  Leu  Lys  Cys  Asp  Ala  Glu  Arg  Glu  Asn  Phe  His  Arg  Leu  Cys
     385                      390                      395

GAA  AAC  TAC  ATC  AAG  AGC  TGG  TTT  GAG  GGC  CAA  GGG  CTG  GCC  GGG  AAG      1247
Glu  Asn  Tyr  Ile  Lys  Ser  Trp  Phe  Glu  Gly  Gln  Gly  Leu  Ala  Gly  Lys
400                      405                      410                      415

CTA  CGG  GCC  ATC  CAG  ACG  GTG  TCC  TGC  CTC  CTG  CAG  GGC  CCA  TGT  GAC      1295
Leu  Arg  Ala  Ile  Gln  Thr  Val  Ser  Cys  Leu  Leu  Gln  Gly  Pro  Cys  Asp
                    420                      425                      430

GCT  GGC  AAC  CGG  GCC  TTG  GAG  CTG  AGC  GGT  GTC  ATG  GAG  AGT  GTG  ATT      1343
Ala  Gly  Asn  Arg  Ala  Leu  Glu  Leu  Ser  Gly  Val  Met  Glu  Ser  Val  Ile
```

```
                    435                          440                          445
GCT  CTG  TGT  GCC  TCT  GAG  CAG  GAG  GAG  GAG  CAG  CTG  GTG  GCC  GTG  GAG    1391
Ala  Leu  Cys  Ala  Ser  Glu  Gln  Glu  Glu  Glu  Gln  Leu  Val  Ala  Val  Glu
          450                          455                          460

GCT  CTG  ATC  CAT  GCA  GCC  GGC  AAG  GCT  AAG  CGG  GCC  TCA  TTC  ATC  ACT    1439
Ala  Leu  Ile  His  Ala  Ala  Gly  Lys  Ala  Lys  Arg  Ala  Ser  Phe  Ile  Thr
     465                      470                          475

GCC  AAT  GGT  GTC  TCG  CTG  CTG  AAG  GAC  CTA  TAT  AAG  TGC  AGC  GAG  AAG    1487
Ala  Asn  Gly  Val  Ser  Leu  Leu  Lys  Asp  Leu  Tyr  Lys  Cys  Ser  Glu  Lys
480                      485                      490                      495

GAC  AGC  ATC  CGC  ATC  CGG  GCG  CTA  GTG  GGA  CTC  TGT  AAG  CTC  GGT  TCG    1535
Asp  Ser  Ile  Arg  Ile  Arg  Ala  Leu  Val  Gly  Leu  Cys  Lys  Leu  Gly  Ser
                         500                      505                      510

GCT  GGA  GGG  ACT  GAC  TTC  AGC  ATG  AAG  CAG  TTT  GCT  GAA  GGC  TCC  ACT    1583
Ala  Gly  Gly  Thr  Asp  Phe  Ser  Met  Lys  Gln  Phe  Ala  Glu  Gly  Ser  Thr
                    515                      520                      525

CTC  AAA  CTG  GCT  AAG  CAG  TGT  CGA  AAG  TGG  CTG  TGC  AAT  GAC  CAG  ATC    1631
Leu  Lys  Leu  Ala  Lys  Gln  Cys  Arg  Lys  Trp  Leu  Cys  Asn  Asp  Gln  Ile
          530                      535                      540

GAC  GCA  GGC  ACT  CGG  CGC  TGG  GCA  GTG  GAG  GGC  CTG  GCT  TAC  CTG  ACC    1679
Asp  Ala  Gly  Thr  Arg  Arg  Trp  Ala  Val  Glu  Gly  Leu  Ala  Tyr  Leu  Thr
     545                      550                          555

TTT  GAT  GCC  GAC  GTG  AAG  GAA  GAG  TTT  GTG  GAG  GAT  GCG  GCT  GCT  CTG    1727
Phe  Asp  Ala  Asp  Val  Lys  Glu  Glu  Phe  Val  Glu  Asp  Ala  Ala  Ala  Leu
560                      565                      570                      575

AAA  GCT  CTG  TTC  CAG  CTC  AGC  AGG  TTG  GAG  GAG  AGG  TCA  GTG  CTC  TTT    1775
Lys  Ala  Leu  Phe  Gln  Leu  Ser  Arg  Leu  Glu  Glu  Arg  Ser  Val  Leu  Phe
                    580                      585                      590

GCG  GTG  GCC  TCA  GCG  CTG  GTG  AAC  TGC  ACC  AAC  AGC  TAT  GAC  TAC  GAG    1823
Ala  Val  Ala  Ser  Ala  Leu  Val  Asn  Cys  Thr  Asn  Ser  Tyr  Asp  Tyr  Glu
               595                      600                      605

GAG  CCC  GAC  CCC  AAG  ATG  GTG  GAG  CTG  GCC  AAG  TAT  GCC  AAG  CAG  CAT    1871
Glu  Pro  Asp  Pro  Lys  Met  Val  Glu  Leu  Ala  Lys  Tyr  Ala  Lys  Gln  His
          610                      615                      620

GTG  CCC  GAG  CAG  CAC  CCC  AAG  GAC  AAG  CCA  AGC  TTC  GTG  CGG  GCT  CGG    1919
Val  Pro  Glu  Gln  His  Pro  Lys  Asp  Lys  Pro  Ser  Phe  Val  Arg  Ala  Arg
     625                      630                      635

GTG  AAG  AAG  CTG  CTG  GCA  GCG  GGT  GTG  GTG  TCG  GCC  ATG  GTG  TGC  ATG    1967
Val  Lys  Lys  Leu  Leu  Ala  Ala  Gly  Val  Val  Ser  Ala  Met  Val  Cys  Met
640                      645                      650                      655

GTG  AAG  ACG  GAG  AGC  CCT  GTG  CTG  ACC  AGT  TCC  TGC  AGA  GAG  CTG  CTC    2015
Val  Lys  Thr  Glu  Ser  Pro  Val  Leu  Thr  Ser  Ser  Cys  Arg  Glu  Leu  Leu
                    660                      665                      670

TCC  AGG  GTC  TTC  TTG  GCT  TTA  GTG  GAA  GAG  GTA  GAG  GAC  CGA  GGC  ACT    2063
Ser  Arg  Val  Phe  Leu  Ala  Leu  Val  Glu  Glu  Val  Glu  Asp  Arg  Gly  Thr
               675                      680                      685

GTG  GTT  GCC  CAG  GGA  GGC  GGC  AGG  GCG  CTG  ATC  CCG  CTG  GCC  CTG  GAA    2111
Val  Val  Ala  Gln  Gly  Gly  Gly  Arg  Ala  Leu  Ile  Pro  Leu  Ala  Leu  Glu
               690                      695                      700

GGC  ACG  GAC  GTG  GGG  CAG  ACA  AAG  GCA  GCC  CAG  GCC  CTT  GCC  AAG  CTC    2159
Gly  Thr  Asp  Val  Gly  Gln  Thr  Lys  Ala  Ala  Gln  Ala  Leu  Ala  Lys  Leu
     705                      710                      715

ACC  ATC  ACC  TCC  AAC  CCG  GAG  ATG  ACC  TTC  CCT  GGC  GAG  CGG  ATC  TAT    2207
Thr  Ile  Thr  Ser  Asn  Pro  Glu  Met  Thr  Phe  Pro  Gly  Glu  Arg  Ile  Tyr
720                      725                      730                      735

GAG  GTG  GTC  CGG  CCC  CTC  GTC  TCC  CTG  TTG  CAC  CTC  AAC  TGC  TCA  GGC    2255
Glu  Val  Val  Arg  Pro  Leu  Val  Ser  Leu  Leu  His  Leu  Asn  Cys  Ser  Gly
                    740                      745                      750

CTG  CAG  AAC  TTC  GAG  GCG  CTC  ATG  GCC  CTA  ACA  AAC  CTG  GCT  GGG  ATC    2303
Leu  Gln  Asn  Phe  Glu  Ala  Leu  Met  Ala  Leu  Thr  Asn  Leu  Ala  Gly  Ile
```

-continued

```
                755                          760                          765
AGC  GAG  AGG  CTC  CGG  CAG  AAG  ATC  CTG  AAG  GAG  AAG  GCT  GTG  CCC  ATG    2351
Ser  Glu  Arg  Leu  Arg  Gln  Lys  Ile  Leu  Lys  Glu  Lys  Ala  Val  Pro  Met
          770            775                 780

ATA  GAA  GGC  TAC  ATG  TTT  GAG  GAG  CAT  GAG  ATG  ATC  CGC  CGG  GCA  GCC    2399
Ile  Glu  Gly  Tyr  Met  Phe  Glu  Glu  His  Glu  Met  Ile  Arg  Arg  Ala  Ala
     785                      790                      795

ACG  GAG  TGC  ATG  TGT  AAC  TTG  GCC  ATG  AGC  AAG  GAG  GTG  CAG  GAC  CTC    2447
Thr  Glu  Cys  Met  Cys  Asn  Leu  Ala  Met  Ser  Lys  Glu  Val  Gln  Asp  Leu
800                      805                      810                      815

TTC  GAA  GCC  CAG  GGC  AAT  GAC  CGA  CTG  AAG  CTG  CTG  GTG  CTG  TAC  AGT    2495
Phe  Glu  Ala  Gln  Gly  Asn  Asp  Arg  Leu  Lys  Leu  Leu  Val  Leu  Tyr  Ser
                    820                      825                      830

GGA  GAG  GAT  GAT  GAG  CTG  CTA  CAG  CGG  GCA  GCT  GCC  GGG  GGC  TTG  GCC    2543
Gly  Glu  Asp  Asp  Glu  Leu  Leu  Gln  Arg  Ala  Ala  Ala  Gly  Gly  Leu  Ala
               835                      840                      845

ATG  CTT  ACC  TCC  ATG  CGG  CCC  ACG  CTC  TGC  AGC  CGC  ATT  CCC  CAA  GTG    2591
Met  Leu  Thr  Ser  Met  Arg  Pro  Thr  Leu  Cys  Ser  Arg  Ile  Pro  Gln  Val
          850                      855                      860

ACC  ACA  CAC  TGG  CTG  GAG  ATC  CTG  CAG  GCC  CTG  CTT  CTG  AGC  TCC  AAC    2639
Thr  Thr  His  Trp  Leu  Glu  Ile  Leu  Gln  Ala  Leu  Leu  Leu  Ser  Ser  Asn
     865                      870                      875

CAG  GAG  CTG  CAG  CAC  CGG  GGT  GCT  GTG  GTG  GTG  CTG  AAC  ATG  GTG  GAG    2687
Gln  Glu  Leu  Gln  His  Arg  Gly  Ala  Val  Val  Val  Leu  Asn  Met  Val  Glu
880                      885                      890                      895

GCC  TCG  AGG  GAG  ATT  GCC  AGC  ACC  CTG  ATG  GAG  AGT  GAG  ATG  ATG  GAG    2735
Ala  Ser  Arg  Glu  Ile  Ala  Ser  Thr  Leu  Met  Glu  Ser  Glu  Met  Met  Glu
                    900                      905                      910

ATC  TTG  TCA  GTG  CTA  GCT  AAG  GGT  GAC  CAC  AGC  CCT  GTC  ACA  AGG  GCT    2783
Ile  Leu  Ser  Val  Leu  Ala  Lys  Gly  Asp  His  Ser  Pro  Val  Thr  Arg  Ala
               915                      920                      925

GCT  GCA  GCC  TGC  CTG  GAC  AAA  GCA  GTG  GAA  TAT  GGG  CTT  ATC  CAA  CCC    2831
Ala  Ala  Ala  Cys  Leu  Asp  Lys  Ala  Val  Glu  Tyr  Gly  Leu  Ile  Gln  Pro
          930                      935                      940

AAC  CAA  GAT  GGA  GAG  TGAGGGGTT  GTCCCTGGGC  CCAAGGCTCA  TGCACACGCT            2886
Asn  Gln  Asp  Gly  Glu
     945

ACCTATTGTG  GCACGGAGAG  TAAGGACGGA  AGCAGCTTTG  GCTGGTGGTG  GCTGGCATGC            2946

CCAATACTCT  TGCCCATCCT  CGCTTGCTGC  CCTAGGATGT  CCTCTGTTCT  GAGTCAGCGG            3006

CCACGTTCAG  TCACACAGCC  CTGCTTGGCC  AGCACTGCCT  GCAGCCTCAC  TCAGAGGGGC            3066

CCTTTTTCTG  TACTACTGTA  GTCAGCTGGG  AATGGGGAAG  GTGCATCCCA  ACACAGCCTG            3126

TGGATCCTGG  GGCATTTGGA  AGGGCGCACA  CATCAGCAGC  CTCACCAGCT  GTGAGCCTGC            3186

TATCAGGCCT  GCCCCTCCAA  TAAAAGTGTG  TAGAACTCC                                     3225
```

( 2 ) INFORMATION FOR SEQ ID NO:14:

( i ) SEQUENCE CHARACTERISTICS:
        ( A ) LENGTH: 948 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Gln  Thr  Arg  Pro  Ala  Pro  Glu  Thr  Ala  Pro  Ala  Arg  Ala  Arg  Asp  Thr
 1                    5                      10                          15

Leu  Ser  Ala  Met  Thr  Ala  Ser  Ser  Val  Glu  Gln  Leu  Arg  Lys  Glu  Gly
               20                      25                          30
```

```
Asn Glu Leu Phe Lys Cys Gly Asp Tyr Gly Gly Ala Leu Ala Ala Tyr
         35                  40                  45
Thr Gln Ala Leu Gly Leu Asp Ala Thr Pro Gln Asp Gln Ala Val Leu
     50                  55                  60
His Arg Asn Arg Ala Ala Cys His Leu Lys Leu Glu Asp Tyr Asp Lys
 65                  70                  75                  80
Ala Glu Thr Glu Ala Ser Lys Ala Ile Glu Lys Asp Gly Gly Asp Val
                 85                  90                  95
Lys Ala Leu Tyr Arg Arg Ser Gln Ala Leu Glu Lys Leu Gly Arg Leu
            100                 105                 110
Asp Gln Ala Val Leu Asp Leu Gln Arg Cys Val Ser Leu Glu Pro Lys
            115                 120                 125
Asn Lys Val Phe Gln Glu Ala Leu Arg Asn Ile Gly Gly Gln Ile Gln
    130                 135                 140
Glu Lys Val Arg Tyr Met Ser Ser Thr Asp Ala Lys Val Glu Gln Met
145                 150                 155                 160
Phe Gln Ile Leu Leu Asp Pro Glu Glu Lys Gly Thr Glu Lys Lys Gln
                    165                 170                 175
Lys Ala Ser Gln Asn Leu Val Val Leu Ala Arg Glu Asp Ala Gly Ala
                180                 185                 190
Glu Lys Ile Phe Arg Ser Asn Gly Val Gln Leu Leu Gln Arg Leu Leu
            195                 200                 205
Asp Met Gly Glu Thr Asp Leu Met Leu Ala Ala Leu Arg Thr Leu Val
    210                 215                 220
Gly Ile Cys Ser Glu His Gln Ser Arg Thr Val Ala Thr Leu Ser Ile
225                 230                 235                 240
Leu Gly Thr Arg Arg Val Val Ser Ile Leu Gly Val Glu Ser Gln Ala
                    245                 250                 255
Val Ser Leu Ala Ala Cys His Leu Leu Gln Val Met Phe Asp Ala Leu
                260                 265                 270
Lys Glu Gly Val Lys Lys Gly Phe Arg Gly Lys Glu Gly Ala Ile Ile
            275                 280                 285
Val Asp Pro Ala Arg Glu Leu Lys Val Leu Ile Ser Asn Leu Leu Asp
    290                 295                 300
Leu Leu Thr Glu Val Gly Val Ser Gly Gln Gly Arg Asp Asn Ala Leu
305                 310                 315                 320
Thr Leu Leu Ile Lys Ala Val Pro Arg Lys Ser Leu Lys Asp Pro Asn
                    325                 330                 335
Asn Ser Leu Thr Leu Trp Val Ile Asp Gln Gly Leu Lys Lys Ile Leu
                340                 345                 350
Glu Val Gly Gly Ser Leu Gln Asp Pro Pro Gly Glu Leu Ala Val Thr
            355                 360                 365
Ala Asn Ser Arg Met Ser Ala Ser Ile Leu Leu Ser Lys Leu Phe Asp
    370                 375                 380
Asp Leu Lys Cys Asp Ala Glu Arg Glu Asn Phe His Arg Leu Cys Glu
385                 390                 395                 400
Asn Tyr Ile Lys Ser Trp Phe Glu Gly Gln Gly Leu Ala Gly Lys Leu
                    405                 410                 415
Arg Ala Ile Gln Thr Val Ser Cys Leu Leu Gln Gly Pro Cys Asp Ala
                420                 425                 430
Gly Asn Arg Ala Leu Glu Leu Ser Gly Val Met Glu Ser Val Ile Ala
            435                 440                 445
Leu Cys Ala Ser Glu Gln Glu Glu Glu Gln Leu Val Ala Val Glu Ala
    450                 455                 460
```

| Leu | Ile | His | Ala | Ala | Gly | Lys | Ala | Lys | Arg | Ala | Ser | Phe | Ile | Thr | Ala |
|-----|-----|-----|-----|-----|-----|-----|-----|-----|-----|-----|-----|-----|-----|-----|-----|
| 465 |     |     |     |     | 470 |     |     |     | 475 |     |     |     |     |     | 480 |
| Asn | Gly | Val | Ser | Leu | Leu | Lys | Asp | Leu | Tyr | Lys | Cys | Ser | Glu | Lys | Asp |
|     |     |     |     | 485 |     |     |     |     | 490 |     |     |     | 495 |     |     |
| Ser | Ile | Arg | Ile | Arg | Ala | Leu | Val | Gly | Leu | Cys | Lys | Leu | Gly | Ser | Ala |
|     |     |     |     | 500 |     |     |     | 505 |     |     |     | 510 |     |     |     |
| Gly | Gly | Thr | Asp | Phe | Ser | Met | Lys | Gln | Phe | Ala | Glu | Gly | Ser | Thr | Leu |
|     |     |     | 515 |     |     |     | 520 |     |     |     |     | 525 |     |     |     |
| Lys | Leu | Ala | Lys | Gln | Cys | Arg | Lys | Trp | Leu | Cys | Asn | Asp | Gln | Ile | Asp |
|     | 530 |     |     |     |     | 535 |     |     |     |     | 540 |     |     |     |     |
| Ala | Gly | Thr | Arg | Arg | Trp | Ala | Val | Glu | Gly | Leu | Ala | Tyr | Leu | Thr | Phe |
| 545 |     |     |     |     | 550 |     |     |     |     | 555 |     |     |     |     | 560 |
| Asp | Ala | Asp | Val | Lys | Glu | Glu | Phe | Val | Glu | Asp | Ala | Ala | Ala | Leu | Lys |
|     |     |     |     | 565 |     |     |     |     | 570 |     |     |     |     | 575 |     |
| Ala | Leu | Phe | Gln | Leu | Ser | Arg | Leu | Glu | Glu | Arg | Ser | Val | Leu | Phe | Ala |
|     |     |     | 580 |     |     |     |     | 585 |     |     |     |     | 590 |     |     |
| Val | Ala | Ser | Ala | Leu | Val | Asn | Cys | Thr | Asn | Ser | Tyr | Asp | Tyr | Glu | Glu |
|     |     | 595 |     |     |     |     | 600 |     |     |     |     | 605 |     |     |     |
| Pro | Asp | Pro | Lys | Met | Val | Glu | Leu | Ala | Lys | Tyr | Ala | Lys | Gln | His | Val |
|     | 610 |     |     |     |     | 615 |     |     |     |     | 620 |     |     |     |     |
| Pro | Glu | Gln | His | Pro | Lys | Asp | Lys | Pro | Ser | Phe | Val | Arg | Ala | Arg | Val |
| 625 |     |     |     |     | 630 |     |     |     |     | 635 |     |     |     |     | 640 |
| Lys | Lys | Leu | Leu | Ala | Ala | Gly | Val | Val | Ser | Ala | Met | Val | Cys | Met | Val |
|     |     |     |     | 645 |     |     |     |     | 650 |     |     |     |     | 655 |     |
| Lys | Thr | Glu | Ser | Pro | Val | Leu | Thr | Ser | Ser | Cys | Arg | Glu | Leu | Leu | Ser |
|     |     |     | 660 |     |     |     |     | 665 |     |     |     |     | 670 |     |     |
| Arg | Val | Phe | Leu | Ala | Leu | Val | Glu | Val | Glu | Asp | Arg | Gly | Thr | Val |
|     |     | 675 |     |     |     |     | 680 |     |     |     |     | 685 |     |     |
| Val | Ala | Gln | Gly | Gly | Gly | Arg | Ala | Leu | Ile | Pro | Leu | Ala | Leu | Glu | Gly |
|     |     | 690 |     |     |     | 695 |     |     |     |     | 700 |     |     |     |     |
| Thr | Asp | Val | Gly | Gln | Thr | Lys | Ala | Ala | Gln | Ala | Leu | Ala | Lys | Leu | Thr |
| 705 |     |     |     |     | 710 |     |     |     |     | 715 |     |     |     |     | 720 |
| Ile | Thr | Ser | Asn | Pro | Glu | Met | Thr | Phe | Pro | Gly | Glu | Arg | Ile | Tyr | Glu |
|     |     |     |     | 725 |     |     |     |     | 730 |     |     |     |     | 735 |     |
| Val | Val | Arg | Pro | Leu | Val | Ser | Leu | Leu | His | Leu | Asn | Cys | Ser | Gly | Leu |
|     |     |     | 740 |     |     |     |     | 745 |     |     |     |     | 750 |     |     |
| Gln | Asn | Phe | Glu | Ala | Leu | Met | Ala | Leu | Thr | Asn | Leu | Ala | Gly | Ile | Ser |
|     |     | 755 |     |     |     |     | 760 |     |     |     |     | 765 |     |     |     |
| Glu | Arg | Leu | Arg | Gln | Lys | Ile | Leu | Lys | Glu | Lys | Ala | Val | Pro | Met | Ile |
|     | 770 |     |     |     |     | 775 |     |     |     |     | 780 |     |     |     |     |
| Glu | Gly | Tyr | Met | Phe | Glu | Glu | His | Glu | Met | Ile | Arg | Arg | Ala | Ala | Thr |
| 785 |     |     |     |     | 790 |     |     |     |     | 795 |     |     |     |     | 800 |
| Glu | Cys | Met | Cys | Asn | Leu | Ala | Met | Ser | Lys | Glu | Val | Gln | Asp | Leu | Phe |
|     |     |     |     | 805 |     |     |     |     | 810 |     |     |     |     | 815 |     |
| Glu | Ala | Gln | Gly | Asn | Asp | Arg | Leu | Lys | Leu | Leu | Val | Leu | Tyr | Ser | Gly |
|     |     |     | 820 |     |     |     |     | 825 |     |     |     |     | 830 |     |     |
| Glu | Asp | Asp | Glu | Leu | Leu | Gln | Arg | Ala | Ala | Ala | Gly | Gly | Leu | Ala | Met |
|     |     | 835 |     |     |     |     | 840 |     |     |     |     | 845 |     |     |     |
| Leu | Thr | Ser | Met | Arg | Pro | Thr | Leu | Cys | Ser | Arg | Ile | Pro | Gln | Val | Thr |
|     | 850 |     |     |     |     | 855 |     |     |     |     | 860 |     |     |     |     |
| Thr | His | Trp | Leu | Glu | Ile | Leu | Gln | Ala | Leu | Leu | Leu | Ser | Ser | Asn | Gln |
| 865 |     |     |     |     | 870 |     |     |     |     | 875 |     |     |     |     | 880 |
| Glu | Leu | Gln | His | Arg | Gly | Ala | Val | Val | Val | Leu | Asn | Met | Val | Glu | Ala |

885                                         890                                         895

Ser   Arg   Glu   Ile   Ala   Ser   Thr   Leu   Met   Glu   Ser   Glu   Met   Met   Glu   Ile
                  900                           905                     910

Leu   Ser   Val   Leu   Ala   Lys   Gly   Asp   His   Ser   Pro   Val   Thr   Arg   Ala   Ala
            915                           920                           925

Ala   Ala   Cys   Leu   Asp   Lys   Ala   Val   Glu   Tyr   Gly   Leu   Ile   Gln   Pro   Asn
            930                           935                           940

Gln   Asp   Gly   Glu
945

( 2 ) INFORMATION FOR SEQ ID NO:15:

( i ) SEQUENCE CHARACTERISTICS:
        ( A ) LENGTH: 6002 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 326..5092

( x i ) SEQUENCE DESCRIPTION: SEQ ID NO:15:

CACGTGCATG   TGTAGCATGC   CTTGGTTTTT   CCTTTGGCAT   CTGAAAAAGG   CACAACCTGA         60

AAGACCTAGA   ACCCAGTGTC   GGTCCCCAGG   CCCTTTGGGA   CAGGAAGAGA   AGAGCCGTGT        120

GGCCGCGGGG   AGGATGTCCT   GCGGCGGGGC   TGTCCTCGCG   GACTGACTGG   ACTCCATCTC        180

CCAGCGGGCG   CCGCGGCGCG   GCCACGCCCC   CCCACTCCCC   GCGCGCGCCC   GGTGGAGACT        240

TCGATTTTCA   GAATTCCTCC   TGGGAATGCT   GACTCCTTGC   TTGGTGCCCT   GATGCTTCTC        300

TGAGATAAAC   TGATGAATTG   GAACC   ATG   GTG   CAA   AAG   AAG   AAG   TTC   TGT   CCT   352
                                Met   Val   Gln   Lys   Lys   Lys   Phe   Cys   Pro
                                 1                      5

CGG   TTA   CTT   GAC   TAT   CTA   GTG   ATC   GTA   GGG   GCC   AGG   CAC   CCG   AGC   AGT   400
Arg   Leu   Leu   Asp   Tyr   Leu   Val   Ile   Val   Gly   Ala   Arg   His   Pro   Ser   Ser
 10                          15                          20                          25

GAT   AGC   GTG   GCC   CAG   ACT   CCT   GAA   TTG   CTA   CGG   CGA   TAC   CCC   TTG   GAG   448
Asp   Ser   Val   Ala   Gln   Thr   Pro   Glu   Leu   Leu   Arg   Arg   Tyr   Pro   Leu   Glu
                  30                          35                           40

GAT   CAC   ACT   GAG   TTT   CCC   CTG   CCC   CCA   GAT   GTA   GTG   TTC   TTC   TGC   CAG   496
Asp   His   Thr   Glu   Phe   Pro   Leu   Pro   Pro   Asp   Val   Val   Phe   Phe   Cys   Gln
                  45                          50                           55

CCC   GAG   GGC   TGC   CTG   AGC   GTG   CGG   CAG   CGG   CGC   ATG   AGC   CTT   CGG   GAT   544
Pro   Glu   Gly   Cys   Leu   Ser   Val   Arg   Gln   Arg   Arg   Met   Ser   Leu   Arg   Asp
            60                          65                           70

GAT   ACC   TCT   TTT   GTC   TTC   ACC   CTC   ACT   GAC   AAG   GAC   ACT   GGA   GTC   ACG   592
Asp   Thr   Ser   Phe   Val   Phe   Thr   Leu   Thr   Asp   Lys   Asp   Thr   Gly   Val   Thr
            75                          80                           85

CGA   TAT   GGC   ATC   TGT   GTT   AAC   TTC   TAC   CGC   TCC   TTC   CAA   AAG   CGA   ATC   640
Arg   Tyr   Gly   Ile   Cys   Val   Asn   Phe   Tyr   Arg   Ser   Phe   Gln   Lys   Arg   Ile
 90                          95                          100                         105

TCT   AAG   GAG   AAG   GGG   GAA   GGT   GGG   GCA   GGG   TCC   CGT   GGG   AAG   GAA   GGA   688
Ser   Lys   Glu   Lys   Gly   Glu   Gly   Gly   Ala   Gly   Ser   Arg   Gly   Lys   Glu   Gly
                        110                         115                         120

ACC   CAT   GCC   ACC   TGT   GCC   TCA   GAA   GAG   GGT   GGC   ACT   GAG   AGC   TCA   GAG   736
Thr   His   Ala   Thr   Cys   Ala   Ser   Glu   Glu   Gly   Gly   Thr   Glu   Ser   Ser   Glu
                  125                         130                         135

AGT   GGC   TCA   TCC   CTG   CAG   CCT   CTC   AGT   GCT   GAC   TCT   ACC   CCT   GAT   GTG   784

-continued

```
Ser Gly Ser Ser Leu Gln Pro Leu Ser Ala Asp Ser Thr Pro Asp Val
        140                 145                 150

AAC CAG TCT CCT CGG GGC AAA CGC CGG GCC AAG GCG GGG AGC CGC TCC      832
Asn Gln Ser Pro Arg Gly Lys Arg Arg Ala Lys Ala Gly Ser Arg Ser
        155                 160                 165

CGC AAC AGT ACT CTC ACG TCC CTG TGC GTG CTC AGC CAC TAC CCT TTC      880
Arg Asn Ser Thr Leu Thr Ser Leu Cys Val Leu Ser His Tyr Pro Phe
170                 175                 180                 185

TTC TCC ACC TTC CGA GAG TGT TTG TAT ACT CTC AAG CGC CTG GTG GAC      928
Phe Ser Thr Phe Arg Glu Cys Leu Tyr Thr Leu Lys Arg Leu Val Asp
                190                 195                 200

TGC TGT AGT GAG CGC CTT CTG GGC AAG AAA CTG GGC ATC CCT CGA GGC      976
Cys Cys Ser Glu Arg Leu Leu Gly Lys Lys Leu Gly Ile Pro Arg Gly
            205                 210                 215

GTA CAA AGG GAC ACC ATG TGG CGG ATC TTT ACT GGA TCG CTG CTG GTA     1024
Val Gln Arg Asp Thr Met Trp Arg Ile Phe Thr Gly Ser Leu Leu Val
        220                 225                 230

GAG GAG AAG TCA AGT GCC CTT CTG CAT GAC CTT CGA GAG ATT GAG GCC     1072
Glu Glu Lys Ser Ser Ala Leu Leu His Asp Leu Arg Glu Ile Glu Ala
        235                 240                 245

TGG ATC TAT CGA TTG CTG CGC TCC CCA GTA CCC GTC TCT GGG CAG AAG     1120
Trp Ile Tyr Arg Leu Leu Arg Ser Pro Val Pro Val Ser Gly Gln Lys
250                 255                 260                 265

CGA GTA GAC ATC GAG GTC CTA CCC CAA GAG CTC CAG CCA GCT CTG ACC     1168
Arg Val Asp Ile Glu Val Leu Pro Gln Glu Leu Gln Pro Ala Leu Thr
                270                 275                 280

TTT GCT CTT CCA GAC CCA TCT CGA TTC ACC CTA GTG GAT TTC CCA CTG     1216
Phe Ala Leu Pro Asp Pro Ser Arg Phe Thr Leu Val Asp Phe Pro Leu
            285                 290                 295

CAC CTT CCC TTG GAA CTT CTA GGT GTG GAC GCC TGT CTC CAG GTG CTA     1264
His Leu Pro Leu Glu Leu Leu Gly Val Asp Ala Cys Leu Gln Val Leu
        300                 305                 310

ACC TGC ATT CTG TTA GAG CAC AAG GTG GTG CTA CAG TCC CGA GAC TAC     1312
Thr Cys Ile Leu Leu Glu His Lys Val Val Leu Gln Ser Arg Asp Tyr
        315                 320                 325

AAT GCA CTC TCC ATG TCT GTG ATG GCA TTC GTG GCA ATG ATC TAC CCA     1360
Asn Ala Leu Ser Met Ser Val Met Ala Phe Val Ala Met Ile Tyr Pro
330                 335                 340                 345

CTG GAA TAT ATG TTT CCT GTC ATC CCG CTG CTA CCC ACC TGC ATG GCA     1408
Leu Glu Tyr Met Phe Pro Val Ile Pro Leu Leu Pro Thr Cys Met Ala
                350                 355                 360

TCA GCA GAG CAG CTG CTG TTG GCT CCA ACC CCG TAC ATC ATT GGG GTT     1456
Ser Ala Glu Gln Leu Leu Leu Ala Pro Thr Pro Tyr Ile Ile Gly Val
            365                 370                 375

CCT GCC AGC TTC TTC CTC TAC AAA CTG GAC TTC AAA ATG CCT GAT GAT     1504
Pro Ala Ser Phe Phe Leu Tyr Lys Leu Asp Phe Lys Met Pro Asp Asp
        380                 385                 390

GTA TGG CTA GTG GAT CTG GAC AGC AAT AGG GTG ATT GCC CCC ACC AAT     1552
Val Trp Leu Val Asp Leu Asp Ser Asn Arg Val Ile Ala Pro Thr Asn
        395                 400                 405

GCA GAA GTG CTG CCT ATC CTG CCA GAA CCA GAA TCA CTA GAG CTG AAA     1600
Ala Glu Val Leu Pro Ile Leu Pro Glu Pro Glu Ser Leu Glu Leu Lys
410                 415                 420                 425

AAG CAT TTA AAG CAG GCC TTG GCC AGC ATG AGT CTC AAC ACC CAG CCC     1648
Lys His Leu Lys Gln Ala Leu Ala Ser Met Ser Leu Asn Thr Gln Pro
                430                 435                 440

ATC CTC AAT CTG GAG AAA TTT CAT GAG GGC CAG GAG ATC CCC CTT CTC     1696
Ile Leu Asn Leu Glu Lys Phe His Glu Gly Gln Glu Ile Pro Leu Leu
            445                 450                 455

TTG GGA AGG CCT TCT AAT GAC CTG CAG TCC ACA CCG TCC ACT GAA TTC     1744
```

| | | | | | | | | | | | | | | | | |
|---|---|---|---|---|---|---|---|---|---|---|---|---|---|---|---|---|
| Leu | Gly | Arg | Pro | Ser | Asn | Asp | Leu | Gln | Ser | Thr | Pro | Ser | Thr | Glu | Phe | |
| | | 460 | | | | | 465 | | | | | 470 | | | | |
| AAC | CCA | CTC | ATC | TAT | GGC | AAT | GAT | GTG | GAT | TCT | GTG | GAT | GTT | GCA | ACC | 1792 |
| Asn | Pro | Leu | Ile | Tyr | Gly | Asn | Asp | Val | Asp | Ser | Val | Asp | Val | Ala | Thr | |
| | 475 | | | | 480 | | | | | 485 | | | | | | |
| AGG | GTT | GCC | ATG | GTA | CGG | TTC | TTC | AAT | TCC | GCC | AAC | GTG | CTG | CAG | GGA | 1840 |
| Arg | Val | Ala | Met | Val | Arg | Phe | Phe | Asn | Ser | Ala | Asn | Val | Leu | Gln | Gly | |
| 490 | | | | | 495 | | | | | 500 | | | | | 505 | |
| TTT | CAG | ATG | CAC | ACG | CGT | ACC | CTG | CGC | CTC | TTT | CCT | CGG | CCT | GTG | GTA | 1888 |
| Phe | Gln | Met | His | Thr | Arg | Thr | Leu | Arg | Leu | Phe | Pro | Arg | Pro | Val | Val | |
| | | | 510 | | | | | 515 | | | | | 520 | | | |
| GCT | TTT | CAA | GCT | GGC | TCC | TTT | CTA | GCC | TCA | CGT | CCC | CGG | CAG | ACT | CCT | 1936 |
| Ala | Phe | Gln | Ala | Gly | Ser | Phe | Leu | Ala | Ser | Arg | Pro | Arg | Gln | Thr | Pro | |
| | | 525 | | | | | 530 | | | | | 535 | | | | |
| TTT | GCC | GAG | AAA | TTG | GCC | AGG | ACT | CAG | GCT | GTG | GAG | TAC | TTT | GGG | GAA | 1984 |
| Phe | Ala | Glu | Lys | Leu | Ala | Arg | Thr | Gln | Ala | Val | Glu | Tyr | Phe | Gly | Glu | |
| 540 | | | | | 545 | | | | | 550 | | | | | | |
| TGG | ATC | CTT | AAC | CCC | ACC | AAC | TAT | GCC | TTT | CAG | CGA | ATT | CAC | AAC | AAT | 2032 |
| Trp | Ile | Leu | Asn | Pro | Thr | Asn | Tyr | Ala | Phe | Gln | Arg | Ile | His | Asn | Asn | |
| | 555 | | | | | 560 | | | | | 565 | | | | | |
| ATG | TTT | GAT | CCA | GCC | CTG | ATT | GGT | GAC | AAG | CCA | AAG | TGG | TAT | GCT | CAT | 2080 |
| Met | Phe | Asp | Pro | Ala | Leu | Ile | Gly | Asp | Lys | Pro | Lys | Trp | Tyr | Ala | His | |
| 570 | | | | 575 | | | | | 580 | | | | | | 585 | |
| CAG | CTG | CAG | CCT | ATC | CAC | TAT | CGC | GTC | TAT | GAC | AGC | AAT | TCC | CAG | CTG | 2128 |
| Gln | Leu | Gln | Pro | Ile | His | Tyr | Arg | Val | Tyr | Asp | Ser | Asn | Ser | Gln | Leu | |
| | | | | 590 | | | | | 595 | | | | | | 600 | |
| GCT | GAG | GCC | CTG | AGT | GTA | CCA | CCA | GAG | CGG | GAC | TCT | GAC | TCC | GAA | CCT | 2176 |
| Ala | Glu | Ala | Leu | Ser | Val | Pro | Pro | Glu | Arg | Asp | Ser | Asp | Ser | Glu | Pro | |
| | | | 605 | | | | | 610 | | | | | 615 | | | |
| ACT | GAT | GAT | AGT | GGC | AGT | GAT | AGT | ATG | GAT | TAT | GAC | GAT | TCA | AGC | TCT | 2224 |
| Thr | Asp | Asp | Ser | Gly | Ser | Asp | Ser | Met | Asp | Tyr | Asp | Asp | Ser | Ser | Ser | |
| | | 620 | | | | | 625 | | | | | 630 | | | | |
| TCT | TAC | TCC | TCC | CTT | GGT | GAC | TTT | GTC | AGT | GAA | ATG | ATG | AAA | TGT | GAC | 2272 |
| Ser | Tyr | Ser | Ser | Leu | Gly | Asp | Phe | Val | Ser | Glu | Met | Met | Lys | Cys | Asp | |
| | 635 | | | | | 640 | | | | | 645 | | | | | |
| ATT | AAT | GGT | GAT | ACT | CCC | AAT | GTG | GAC | CCT | CTG | ACA | CAT | GCA | GCA | CTG | 2320 |
| Ile | Asn | Gly | Asp | Thr | Pro | Asn | Val | Asp | Pro | Leu | Thr | His | Ala | Ala | Leu | |
| 650 | | | | | 655 | | | | | 660 | | | | | 665 | |
| GGG | GAT | GCC | AGC | GAG | GTG | GAG | ATT | GAC | GAG | CTG | CAG | AAT | CAG | AAG | GAA | 2368 |
| Gly | Asp | Ala | Ser | Glu | Val | Glu | Ile | Asp | Glu | Leu | Gln | Asn | Gln | Lys | Glu | |
| | | | | 670 | | | | | 675 | | | | | 680 | | |
| GCA | GAA | GAG | CCT | GGC | CCA | GAC | AGT | GAG | AAC | TCT | CAG | GAA | AAC | CCC | CCA | 2416 |
| Ala | Glu | Glu | Pro | Gly | Pro | Asp | Ser | Glu | Asn | Ser | Gln | Glu | Asn | Pro | Pro | |
| | | | 685 | | | | | 690 | | | | | 695 | | | |
| CTG | CGC | TCC | AGC | TCT | AGC | ACC | ACA | GCC | AGC | AGC | AGC | CCC | AGC | ACT | GTC | 2464 |
| Leu | Arg | Ser | Ser | Ser | Ser | Thr | Thr | Ala | Ser | Ser | Ser | Pro | Ser | Thr | Val | |
| | | 700 | | | | | 705 | | | | | 710 | | | | |
| ATC | CAC | GGA | GCC | AAC | TCT | GAA | CCT | GCT | GAC | TCT | ACG | GAG | ATG | GAT | GAT | 2512 |
| Ile | His | Gly | Ala | Asn | Ser | Glu | Pro | Ala | Asp | Ser | Thr | Glu | Met | Asp | Asp | |
| | 715 | | | | | 720 | | | | | 725 | | | | | |
| AAG | GCA | GCA | GTA | GGC | GTC | TCC | AAG | CCC | CTC | CCT | TCC | GTG | CCT | CCC | AGC | 2560 |
| Lys | Ala | Ala | Val | Gly | Val | Ser | Lys | Pro | Leu | Pro | Ser | Val | Pro | Pro | Ser | |
| 730 | | | | | 735 | | | | | 740 | | | | | 745 | |
| ATT | GGC | AAA | TCG | AAC | ATG | GAC | AGA | CGT | CAG | GCA | GAA | ATT | GGA | GAG | GGG | 2608 |
| Ile | Gly | Lys | Ser | Asn | Met | Asp | Arg | Arg | Gln | Ala | Glu | Ile | Gly | Glu | Gly | |
| | | | | 750 | | | | | 755 | | | | | 760 | | |
| TCA | GTG | CGC | CGG | CGA | ATC | TAT | GAC | AAT | CCA | TAC | TTC | GAG | CCC | CAA | TAT | 2656 |
| Ser | Val | Arg | Arg | Arg | Ile | Tyr | Asp | Asn | Pro | Tyr | Phe | Glu | Pro | Gln | Tyr | |
| | | | 765 | | | | | 770 | | | | | 775 | | | |
| GGC | TTT | CCC | CCT | GAG | GAA | GAT | GAG | GAT | GAG | CAG | GGG | GAA | AGT | TAC | ACT | 2704 |

|  |  |  |  |  |  |  |  |  |  |  |  |  |  |  |  |
|---|---|---|---|---|---|---|---|---|---|---|---|---|---|---|---|
| Gly | Phe | Pro | Pro | Glu | Glu | Asp | Glu | Asp | Glu | Gln | Gly | Glu | Ser | Tyr | Thr |
|  |  | 780 |  |  |  | 785 |  |  |  |  | 790 |  |  |  |  |

| CCC | CGA | TTC | AGC | CAA | CAT | GTC | AGT | GGC | AAT | CGG | GCT | CAA | AAG | CTG | CTG | 2752 |
|---|---|---|---|---|---|---|---|---|---|---|---|---|---|---|---|---|
| Pro | Arg | Phe | Ser | Gln | His | Val | Ser | Gly | Asn | Arg | Ala | Gln | Lys | Leu | Leu |  |
|  | 795 |  |  |  | 800 |  |  |  |  | 805 |  |  |  |  |  |  |

| CGG | CCC | AAC | AGC | TTG | AGA | CTG | GCA | AGT | GAC | TCA | GAT | GCA | GAG | TCA | GAC | 2800 |
|---|---|---|---|---|---|---|---|---|---|---|---|---|---|---|---|---|
| Arg | Pro | Asn | Ser | Leu | Arg | Leu | Ala | Ser | Asp | Ser | Asp | Ala | Glu | Ser | Asp |  |
| 810 |  |  |  |  | 815 |  |  |  |  | 820 |  |  |  |  | 825 |  |

| TCT | CGG | GCA | AGC | TCT | CCC | AAC | TCC | ACC | GTC | TCC | AAC | ACC | AGC | ACC | GAG | 2848 |
|---|---|---|---|---|---|---|---|---|---|---|---|---|---|---|---|---|
| Ser | Arg | Ala | Ser | Ser | Pro | Asn | Ser | Thr | Val | Ser | Asn | Thr | Ser | Thr | Glu |  |
|  |  |  |  | 830 |  |  |  |  | 835 |  |  |  |  | 840 |  |  |

| GGC | TTC | GGG | GGC | ATC | ATG | TCT | TTT | GCC | AGC | AGC | CTC | TAT | CGG | AAC | CAC | 2896 |
|---|---|---|---|---|---|---|---|---|---|---|---|---|---|---|---|---|
| Gly | Phe | Gly | Gly | Ile | Met | Ser | Phe | Ala | Ser | Ser | Leu | Tyr | Arg | Asn | His |  |
|  |  |  |  | 845 |  |  |  | 850 |  |  |  |  | 855 |  |  |  |

| AGT | ACC | AGC | TTC | AGT | CTT | TCA | AAC | CTC | ACA | CTG | CCC | ACC | AAA | GGT | GCC | 2944 |
|---|---|---|---|---|---|---|---|---|---|---|---|---|---|---|---|---|
| Ser | Thr | Ser | Phe | Ser | Leu | Ser | Asn | Leu | Thr | Leu | Pro | Thr | Lys | Gly | Ala |  |
|  |  | 860 |  |  |  |  | 865 |  |  |  |  | 870 |  |  |  |  |

| CGA | GAG | AAG | GCC | ACG | CCC | TTC | CCC | AGT | CTG | AAA | GGA | AAC | AGG | AGG | GCG | 2992 |
|---|---|---|---|---|---|---|---|---|---|---|---|---|---|---|---|---|
| Arg | Glu | Lys | Ala | Thr | Pro | Phe | Pro | Ser | Leu | Lys | Gly | Asn | Arg | Arg | Ala |  |
|  | 875 |  |  |  |  | 880 |  |  |  |  | 885 |  |  |  |  |  |

| TTA | GTG | GAT | CAG | AAG | TCA | TCT | GTC | ATT | AAA | CAC | AGC | CCA | ACA | GTG | AAA | 3040 |
|---|---|---|---|---|---|---|---|---|---|---|---|---|---|---|---|---|
| Leu | Val | Asp | Gln | Lys | Ser | Ser | Val | Ile | Lys | His | Ser | Pro | Thr | Val | Lys |  |
| 890 |  |  |  |  | 895 |  |  |  |  | 900 |  |  |  |  | 905 |  |

| AGA | GAA | CCT | CCA | TCA | CCC | CAG | GGT | CGA | TCC | AGC | AAT | TCT | AGT | GAG | AAC | 3088 |
|---|---|---|---|---|---|---|---|---|---|---|---|---|---|---|---|---|
| Arg | Glu | Pro | Pro | Ser | Pro | Gln | Gly | Arg | Ser | Ser | Asn | Ser | Ser | Glu | Asn |  |
|  |  |  |  | 910 |  |  |  |  | 915 |  |  |  |  | 920 |  |  |

| CAG | CAG | TTC | CTG | AAG | GAG | GTG | GTG | CAC | AGC | GTG | CTG | GAC | GGC | CAG | GGA | 3136 |
|---|---|---|---|---|---|---|---|---|---|---|---|---|---|---|---|---|
| Gln | Gln | Phe | Leu | Lys | Glu | Val | Val | His | Ser | Val | Leu | Asp | Gly | Gln | Gly |  |
|  |  |  | 925 |  |  |  |  | 930 |  |  |  |  | 935 |  |  |  |

| GTT | GGC | TGG | CTC | AAC | ATG | AAA | AAG | GTG | CGC | CGG | CTG | CTG | GAG | AGC | GAG | 3184 |
|---|---|---|---|---|---|---|---|---|---|---|---|---|---|---|---|---|
| Val | Gly | Trp | Leu | Asn | Met | Lys | Lys | Val | Arg | Arg | Leu | Leu | Glu | Ser | Glu |  |
|  |  | 940 |  |  |  |  | 945 |  |  |  |  | 950 |  |  |  |  |

| CAG | CTG | CGA | GTC | TTT | GTC | CTG | AGC | AAG | CTG | AAC | CGC | ATG | GTG | CAG | TCA | 3232 |
|---|---|---|---|---|---|---|---|---|---|---|---|---|---|---|---|---|
| Gln | Leu | Arg | Val | Phe | Val | Leu | Ser | Lys | Leu | Asn | Arg | Met | Val | Gln | Ser |  |
| 955 |  |  |  |  | 960 |  |  |  |  | 965 |  |  |  |  |  |  |

| GAG | GAC | GAT | GCC | CGG | CAG | GAC | ATC | ATC | CCG | GAT | GTG | GAG | ATC | AGT | CGG | 3280 |
|---|---|---|---|---|---|---|---|---|---|---|---|---|---|---|---|---|
| Glu | Asp | Asp | Ala | Arg | Gln | Asp | Ile | Ile | Pro | Asp | Val | Glu | Ile | Ser | Arg |  |
| 970 |  |  |  |  | 975 |  |  |  |  | 980 |  |  |  |  | 985 |  |

| AAG | GTG | TAC | AAG | GGA | ATG | TTA | GAC | CTC | CTC | AAG | TGT | ACA | GTC | CTC | AGC | 3328 |
|---|---|---|---|---|---|---|---|---|---|---|---|---|---|---|---|---|
| Lys | Val | Tyr | Lys | Gly | Met | Leu | Asp | Leu | Leu | Lys | Cys | Thr | Val | Leu | Ser |  |
|  |  |  |  | 990 |  |  |  |  | 995 |  |  |  |  | 1000 |  |  |

| TTG | GAG | CAG | TCC | TAT | GCC | CAC | GCG | GGT | CTG | GGT | GGC | ATG | GCC | AGC | ATC | 3376 |
|---|---|---|---|---|---|---|---|---|---|---|---|---|---|---|---|---|
| Leu | Glu | Gln | Ser | Tyr | Ala | His | Ala | Gly | Leu | Gly | Gly | Met | Ala | Ser | Ile |  |
|  |  |  | 1005 |  |  |  |  | 1010 |  |  |  |  | 1015 |  |  |  |

| TTT | GGG | CTT | TTG | GAG | ATT | GCC | CAG | ACC | CAC | TAC | TAT | AGT | AAA | GAA | CCA | 3424 |
|---|---|---|---|---|---|---|---|---|---|---|---|---|---|---|---|---|
| Phe | Gly | Leu | Leu | Glu | Ile | Ala | Gln | Thr | His | Tyr | Tyr | Ser | Lys | Glu | Pro |  |
|  |  | 1020 |  |  |  |  | 1025 |  |  |  |  | 1030 |  |  |  |  |

| GAC | AAG | CGG | AAG | AGA | AGT | CCA | ACA | GAA | AGT | GTA | AAT | ACC | CCA | GTT | GGC | 3472 |
|---|---|---|---|---|---|---|---|---|---|---|---|---|---|---|---|---|
| Asp | Lys | Arg | Lys | Arg | Ser | Pro | Thr | Glu | Ser | Val | Asn | Thr | Pro | Val | Gly |  |
|  | 1035 |  |  |  |  | 1040 |  |  |  |  | 1045 |  |  |  |  |  |

| AAG | GAT | CCT | GGC | CTA | GCT | GGG | CGG | GGG | GAC | CCA | AAG | GCT | ATG | GCA | CAA | 3520 |
|---|---|---|---|---|---|---|---|---|---|---|---|---|---|---|---|---|
| Lys | Asp | Pro | Gly | Leu | Ala | Gly | Arg | Gly | Asp | Pro | Lys | Ala | Met | Ala | Gln |  |
| 1050 |  |  |  |  | 1055 |  |  |  |  | 1060 |  |  |  |  | 1065 |  |

| CTG | AGA | GTT | CCA | CAA | CTG | GGA | CCT | CGG | GCA | CCA | AGT | GCC | ACA | GGA | AAG | 3568 |
|---|---|---|---|---|---|---|---|---|---|---|---|---|---|---|---|---|
| Leu | Arg | Val | Pro | Gln | Leu | Gly | Pro | Arg | Ala | Pro | Ser | Ala | Thr | Gly | Lys |  |
|  |  |  |  | 1070 |  |  |  |  | 1075 |  |  |  |  | 1080 |  |  |

| GGT | CCT | AAG | GAA | CTG | GAC | ACC | AGA | AGT | TTA | AAG | GAA | GAA | AAT | TTT | ATA | 3616 |
|---|---|---|---|---|---|---|---|---|---|---|---|---|---|---|---|---|
| Gly | Pro | Lys | Glu | Leu | Asp | Thr | Arg | Ser | Leu | Lys | Glu | Glu | Asn | Phe | Ile |  |
|  |  |  | 1085 |  |  |  |  | 1090 |  |  |  |  | 1095 |  |  |  |

| GCA | TCT | ATT | GGG | CCT | GAA | GTA | ATC | AAA | CCT | GTC | TTT | GAC | CTT | GGT | GAG | 3664 |

|     |     |     |     |     |     |     |     |     |     |     |     |     |     |     |     |
|---|---|---|---|---|---|---|---|---|---|---|---|---|---|---|---|
| Ala | Ser | Ile | Gly | Pro | Glu | Val | Ile | Lys | Pro | Val | Phe | Asp | Leu | Gly | Glu |
|     |     |     | 1100 |     |     |     | 1105 |     |     |     | 1110 |     |     |     |     |

| ACA | GAG | GAG | AAA | AAG | TCC | CAG | ATC | AGC | GCA | GAC | AGT | GGT | GTG | AGC | CTG | 3712 |
|---|---|---|---|---|---|---|---|---|---|---|---|---|---|---|---|---|
| Thr | Glu | Glu | Lys | Lys | Ser | Gln | Ile | Ser | Ala | Asp | Ser | Gly | Val | Ser | Leu |  |
|  | 1115 |  |  |  | 1120 |  |  |  | 1125 |  |  |  |  |  |  |  |

| ACG | TCT | AGT | TCC | CAG | AGG | ACT | GAT | CAA | GAC | TCT | GTC | ATC | GGC | GTG | AGT | 3760 |
|---|---|---|---|---|---|---|---|---|---|---|---|---|---|---|---|---|
| Thr | Ser | Ser | Ser | Gln | Arg | Thr | Asp | Gln | Asp | Ser | Val | Ile | Gly | Val | Ser |  |
| 1130 |  |  |  | 1135 |  |  |  |  | 1140 |  |  |  |  |  | 1145 |  |

| CCA | GCT | GTT | ATG | ATC | CGC | AGC | TCA | AGT | CAG | GAT | TCT | GAA | GTT | AGC | ACC | 3808 |
|---|---|---|---|---|---|---|---|---|---|---|---|---|---|---|---|---|
| Pro | Ala | Val | Met | Ile | Arg | Ser | Ser | Ser | Gln | Asp | Ser | Glu | Val | Ser | Thr |  |
|  |  |  |  | 1150 |  |  |  |  | 1155 |  |  |  |  | 1160 |  |  |

| GTG | GTG | AGT | AAT | AGC | TCT | GGA | GAG | ACC | CTT | GGA | GCT | GAC | AGT | GAC | TTG | 3856 |
|---|---|---|---|---|---|---|---|---|---|---|---|---|---|---|---|---|
| Val | Val | Ser | Asn | Ser | Ser | Gly | Glu | Thr | Leu | Gly | Ala | Asp | Ser | Asp | Leu |  |
|  |  |  |  | 1165 |  |  |  |  | 1170 |  |  |  | 1175 |  |  |  |

| AGC | AGC | AAT | GCA | GGT | GAT | GGA | CCA | GGT | GGC | GAG | GGC | AGT | GTT | CAC | CTG | 3904 |
|---|---|---|---|---|---|---|---|---|---|---|---|---|---|---|---|---|
| Ser | Ser | Asn | Ala | Gly | Asp | Gly | Pro | Gly | Gly | Glu | Gly | Ser | Val | His | Leu |  |
|  |  |  | 1180 |  |  |  |  | 1185 |  |  |  |  | 1190 |  |  |  |

| GCA | AGC | TCT | CGG | GGC | ACT | TTG | TCT | GAT | AGT | GAA | ATT | GAG | ACC | AAC | TCT | 3952 |
|---|---|---|---|---|---|---|---|---|---|---|---|---|---|---|---|---|
| Ala | Ser | Ser | Arg | Gly | Thr | Leu | Ser | Asp | Ser | Glu | Ile | Glu | Thr | Asn | Ser |  |
|  |  | 1195 |  |  |  |  | 1200 |  |  |  |  | 1205 |  |  |  |  |

| GCC | ACA | AGC | ACC | ATC | TTT | GGT | AAA | GCC | CAC | AGC | TTG | AAG | CCA | AGC | ATA | 4000 |
|---|---|---|---|---|---|---|---|---|---|---|---|---|---|---|---|---|
| Ala | Thr | Ser | Thr | Ile | Phe | Gly | Lys | Ala | His | Ser | Leu | Lys | Pro | Ser | Ile |  |
| 1210 |  |  |  |  | 1215 |  |  |  |  | 1220 |  |  |  |  | 1225 |  |

| AAG | GAG | AAG | CTG | GCA | GGC | AGC | CCC | ATT | CGT | ACT | TCT | GAA | GAT | GTG | AGC | 4048 |
|---|---|---|---|---|---|---|---|---|---|---|---|---|---|---|---|---|
| Lys | Glu | Lys | Leu | Ala | Gly | Ser | Pro | Ile | Arg | Thr | Ser | Glu | Asp | Val | Ser |  |
|  |  |  |  | 1230 |  |  |  |  | 1235 |  |  |  |  | 1240 |  |  |

| CAG | CGA | GTC | TAT | CTC | TAT | GAG | GGA | CTC | CTA | GGC | AAA | GAG | CGT | TCT | ACT | 4096 |
|---|---|---|---|---|---|---|---|---|---|---|---|---|---|---|---|---|
| Gln | Arg | Val | Tyr | Leu | Tyr | Glu | Gly | Leu | Leu | Gly | Lys | Glu | Arg | Ser | Thr |  |
|  |  |  | 1245 |  |  |  |  | 1250 |  |  |  |  | 1255 |  |  |  |

| TTA | TGG | GAC | CAA | ATG | CAA | TTC | TGG | GAA | GAT | GCC | TTC | TTA | GAT | GCT | GTG | 4144 |
|---|---|---|---|---|---|---|---|---|---|---|---|---|---|---|---|---|
| Leu | Trp | Asp | Gln | Met | Gln | Phe | Trp | Glu | Asp | Ala | Phe | Leu | Asp | Ala | Val |  |
|  |  | 1260 |  |  |  |  | 1265 |  |  |  |  | 1270 |  |  |  |  |

| ATG | TTG | GAG | AGA | GAA | GGG | ATG | GGT | ATG | GAC | CAG | GGT | CCC | CAG | GAA | ATG | 4192 |
|---|---|---|---|---|---|---|---|---|---|---|---|---|---|---|---|---|
| Met | Leu | Glu | Arg | Glu | Gly | Met | Gly | Met | Asp | Gln | Gly | Pro | Gln | Glu | Met |  |
|  | 1275 |  |  |  |  | 1280 |  |  |  |  | 1285 |  |  |  |  |  |

| ATC | GAC | AGG | TAC | CTG | TCC | CTT | GGA | GAA | CAT | GAC | CGG | AAG | CGC | CTG | GAA | 4240 |
|---|---|---|---|---|---|---|---|---|---|---|---|---|---|---|---|---|
| Ile | Asp | Arg | Tyr | Leu | Ser | Leu | Gly | Glu | His | Asp | Arg | Lys | Arg | Leu | Glu |  |
| 1290 |  |  |  |  | 1295 |  |  |  |  | 1300 |  |  |  |  | 1305 |  |

| GAT | GAT | GAA | GAT | CGC | TTG | CTG | GCC | ACA | CTT | CTG | CAC | AAC | CTC | ATC | TCC | 4288 |
|---|---|---|---|---|---|---|---|---|---|---|---|---|---|---|---|---|
| Asp | Asp | Glu | Asp | Arg | Leu | Leu | Ala | Thr | Leu | Leu | His | Asn | Leu | Ile | Ser |  |
|  |  |  |  | 1310 |  |  |  |  | 1315 |  |  |  |  | 1320 |  |  |

| TAC | ATG | CTG | CTG | ATG | AAG | GTA | AAT | AAG | AAT | GAC | ATC | CGC | AAG | AAG | GTG | 4336 |
|---|---|---|---|---|---|---|---|---|---|---|---|---|---|---|---|---|
| Tyr | Met | Leu | Leu | Met | Lys | Val | Asn | Lys | Asn | Asp | Ile | Arg | Lys | Lys | Val |  |
|  |  |  | 1325 |  |  |  |  | 1330 |  |  |  |  | 1335 |  |  |  |

| AGG | CGC | CTA | ATG | GGA | AAG | TCG | CAC | ATT | GGG | CTT | GTG | TAC | AGC | CAG | CAA | 4384 |
|---|---|---|---|---|---|---|---|---|---|---|---|---|---|---|---|---|
| Arg | Arg | Leu | Met | Gly | Lys | Ser | His | Ile | Gly | Leu | Val | Tyr | Ser | Gln | Gln |  |
|  |  | 1340 |  |  |  |  | 1345 |  |  |  |  | 1350 |  |  |  |  |

| ATC | AAT | GAG | GTG | CTT | GAT | CAG | CTG | GCG | AAC | CTG | AAT | GGA | CGC | GAT | CTC | 4432 |
|---|---|---|---|---|---|---|---|---|---|---|---|---|---|---|---|---|
| Ile | Asn | Glu | Val | Leu | Asp | Gln | Leu | Ala | Asn | Leu | Asn | Gly | Arg | Asp | Leu |  |
|  | 1355 |  |  |  |  | 1360 |  |  |  |  | 1365 |  |  |  |  |  |

| TCT | ATC | TGG | TCC | AGT | GGC | AGC | CGG | CAC | ATG | AAG | AAG | CAG | ACA | TTT | GTG | 4480 |
|---|---|---|---|---|---|---|---|---|---|---|---|---|---|---|---|---|
| Ser | Ile | Trp | Ser | Ser | Gly | Ser | Arg | His | Met | Lys | Lys | Gln | Thr | Phe | Val |  |
| 1370 |  |  |  |  | 1375 |  |  |  |  | 1380 |  |  |  |  | 1385 |  |

| GTA | CAT | GCA | GGG | ACA | GAT | ACA | AAC | GGA | GAT | ATC | TTT | TTC | ATG | GAG | GTG | 4528 |
|---|---|---|---|---|---|---|---|---|---|---|---|---|---|---|---|---|
| Val | His | Ala | Gly | Thr | Asp | Thr | Asn | Gly | Asp | Ile | Phe | Phe | Met | Glu | Val |  |
|  |  |  |  | 1390 |  |  |  |  | 1395 |  |  |  |  | 1400 |  |  |

| TGC | GAT | GAC | TGT | GTG | GTG | TTG | CGT | AGT | AAC | ATC | GGA | ACA | GTG | TAT | GAG | 4576 |
|---|---|---|---|---|---|---|---|---|---|---|---|---|---|---|---|---|
| Cys | Asp | Asp | Cys | Val | Val | Leu | Arg | Ser | Asn | Ile | Gly | Thr | Val | Tyr | Glu |  |
|  |  |  |  | 1405 |  |  |  |  | 1410 |  |  |  |  | 1415 |  |  |

| CGC | TGG | TGG | TAC | GAG | AAG | CTC | ATC | AAC | ATG | ACC | TAC | TGT | CCC | AAG | ACG | 4624 |
|---|---|---|---|---|---|---|---|---|---|---|---|---|---|---|---|---|

```
Arg Trp Trp Tyr Glu Lys Leu Ile Asn Met Thr Tyr Cys Pro Lys Thr
            1420                1425                1430

AAG GTG TTG TGC TTG TGG CGT AGA AAT GGC TCT GAG ACC CAG CTC AAC       4672
Lys Val Leu Cys Leu Trp Arg Arg Asn Gly Ser Glu Thr Gln Leu Asn
        1435                1440                1445

AAG TTC TAT ACT AAA AAG TGT CGG GAG CTG TAC TAC TGT GTG AAG GAC       4720
Lys Phe Tyr Thr Lys Lys Cys Arg Glu Leu Tyr Tyr Cys Val Lys Asp
1450                1455                1460                1465

AGC ATG GAG CGC GCT GCC GCC CGA CAG CAA AGC ATC AAA CCC GGA CCT       4768
Ser Met Glu Arg Ala Ala Ala Arg Gln Gln Ser Ile Lys Pro Gly Pro
                1470                1475                1480

GAA TTG GGT GGC GAG TTC CCT GTG CAG GAC CTG AAG ACT GGT GAG GGT       4816
Glu Leu Gly Gly Glu Phe Pro Val Gln Asp Leu Lys Thr Gly Glu Gly
                    1485                1490                1495

GGC CTG CTG CAG GTG ACC CTG GAA GGG ATC AAC CTC AAA TTC ATG CAC       4864
Gly Leu Leu Gln Val Thr Leu Glu Gly Ile Asn Leu Lys Phe Met His
            1500                1505                1510

AAT CAG GTT TTC ATA GAG CTG AAT CAC ATT AAA AAG TGC AAT ACA GTT       4912
Asn Gln Val Phe Ile Glu Leu Asn His Ile Lys Lys Cys Asn Thr Val
        1515                1520                1525

CGA GGC GTC TTT GTC CTG GAG GAA TTT GTT CCT GAA ATT AAA GAA GTG       4960
Arg Gly Val Phe Val Leu Glu Glu Phe Val Pro Glu Ile Lys Glu Val
1530                1535                1540                1545

GTG AGC CAC AAG TAC AAG ACA CCA ATG GCC CAC GAA ATC TGC TAC TCC       5008
Val Ser His Lys Tyr Lys Thr Pro Met Ala His Glu Ile Cys Tyr Ser
                1550                1555                1560

GTA TTA TGT CTC TTC TCG TAC GTG GCT GCA GTT CAT AGC AGT GAG GAA       5056
Val Leu Cys Leu Phe Ser Tyr Val Ala Ala Val His Ser Ser Glu Glu
                    1565                1570                1575

GAT CTC AGA ACC CCG CCC CGG CCT GTC TCT AGC TGA TGGAGAGGGG            5102
Asp Leu Arg Thr Pro Pro Arg Pro Val Ser Ser  *
            1580                1585

CTACGCAGCT GCCCCAGCCC AGGGCACGCC CCTGGCCCCT TGCTGTTCCC AAGTGCACGA     5162

TGCTGCTGTG ACTGAGGAGT GGATGATGCT CGTGTGTCCT CTGCAAGCCC CCTGCTGTGG     5222

CTTGGTTGGT TACCGGTTAT GTGTCCCTCT GAGTGTGTCT TGAGCGTGTC CACCTTCTCC     5282

CTCTCCACTC CCAGAAGACC AAACTGCCTT CCCCTCAGGG CTCAAGAATG TGTACAGTCT     5342

GTGGGGCCGG TGTGAACCCA CTATTTTGTG TCCTTGAGAC ATTTGTGTTG TGGTTCCTTG     5402

TCCTTGTCCC TGGCGTTATA ACTGTCCACT GCAAGAGTCT GGCTCTCCCT TCTCTGTGAC     5462

CCGGCATGAC TGGGCGCCTG GAGCAGTTTC ACTCTGTGAG GAGTGAGGGA ACCCTGGGGC     5522

TCACCCTCTC AGAGGAAGGG CACAGAGAGG AAGGGAAGAA TTGGGGGGCA GCCGGAGTGA     5582

GTGGCAGCCT CCCTGCTTCC TTCTGCATTC CCAAGCCGGC AGCTACTGCC CAGGGCCCGC     5642

AGTGTTGGCT GCTGCCTGCC ACAGCCTCTG TGACTGCAGT GGAGCGGCGA ATTCCCTGTG     5702

GCCTGCCACG CCTTCGGCAT CAGAGGATGG AGTGGTCGAG GCTAGTGGAG TCCCAGGGAC     5762

CGCTGGCTGC TCTGCCTGAG CATCAGGGAG GGGGCAGGAA AGACCAAGCT GGGTTTGCAC     5822

ATCTGTCTGC AGGCTGTCTC TCCAGGCACG GGGTGTCAGG AGGGAGAGAC AGCCTGGGTA     5882

TGGGCAAGAA ATGACTGTAA ATATTTCAGC CCCACATTAT TTATAGAAAA TGTACAGTTG     5942

TGTGAATGTG AAATAAATGT CCTCAACTCC CAAAAAAAAA AAAAAAAAA AAAAAAAAA      6002
```

( 2 ) INFORMATION FOR SEQ ID NO:16:

( i ) SEQUENCE CHARACTERISTICS:
        ( A ) LENGTH: 1588 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

| Met | Val | Gln | Lys | Lys | Lys | Phe | Cys | Pro | Arg | Leu | Leu | Asp | Tyr | Leu | Val |
|---|---|---|---|---|---|---|---|---|---|---|---|---|---|---|---|
| 1 | | | | 5 | | | | | 10 | | | | | 15 | |

| Ile | Val | Gly | Ala | Arg | His | Pro | Ser | Ser | Asp | Ser | Val | Ala | Gln | Thr | Pro |
|---|---|---|---|---|---|---|---|---|---|---|---|---|---|---|---|
| | | | 20 | | | | 25 | | | | | 30 | | | |

| Glu | Leu | Leu | Arg | Arg | Tyr | Pro | Leu | Glu | Asp | His | Thr | Glu | Phe | Pro | Leu |
|---|---|---|---|---|---|---|---|---|---|---|---|---|---|---|---|
| | | 35 | | | | | 40 | | | | | 45 | | | |

| Pro | Pro | Asp | Val | Val | Phe | Phe | Cys | Gln | Pro | Glu | Gly | Cys | Leu | Ser | Val |
|---|---|---|---|---|---|---|---|---|---|---|---|---|---|---|---|
| | 50 | | | | | 55 | | | | | 60 | | | | |

| Arg | Gln | Arg | Arg | Met | Ser | Leu | Arg | Asp | Asp | Thr | Ser | Phe | Val | Phe | Thr |
|---|---|---|---|---|---|---|---|---|---|---|---|---|---|---|---|
| 65 | | | | | 70 | | | | | 75 | | | | | 80 |

| Leu | Thr | Asp | Lys | Asp | Thr | Gly | Val | Thr | Arg | Tyr | Gly | Ile | Cys | Val | Asn |
|---|---|---|---|---|---|---|---|---|---|---|---|---|---|---|---|
| | | | | 85 | | | | | 90 | | | | | 95 | |

| Phe | Tyr | Arg | Ser | Phe | Gln | Lys | Arg | Ile | Ser | Lys | Glu | Lys | Gly | Glu | Gly |
|---|---|---|---|---|---|---|---|---|---|---|---|---|---|---|---|
| | | | 100 | | | | 105 | | | | | 110 | | | |

| Gly | Ala | Gly | Ser | Arg | Gly | Lys | Glu | Gly | Thr | His | Ala | Thr | Cys | Ala | Ser |
|---|---|---|---|---|---|---|---|---|---|---|---|---|---|---|---|
| | | 115 | | | | | 120 | | | | | 125 | | | |

| Glu | Glu | Gly | Gly | Thr | Glu | Ser | Ser | Glu | Ser | Gly | Ser | Ser | Leu | Gln | Pro |
|---|---|---|---|---|---|---|---|---|---|---|---|---|---|---|---|
| | 130 | | | | | 135 | | | | | 140 | | | | |

| Leu | Ser | Ala | Asp | Ser | Thr | Pro | Asp | Val | Asn | Gln | Ser | Pro | Arg | Gly | Lys |
|---|---|---|---|---|---|---|---|---|---|---|---|---|---|---|---|
| 145 | | | | | 150 | | | | | 155 | | | | | 160 |

| Arg | Arg | Ala | Lys | Ala | Gly | Ser | Arg | Ser | Arg | Asn | Ser | Thr | Leu | Thr | Ser |
|---|---|---|---|---|---|---|---|---|---|---|---|---|---|---|---|
| | | | | 165 | | | | | 170 | | | | | 175 | |

| Leu | Cys | Val | Leu | Ser | His | Tyr | Pro | Phe | Phe | Ser | Thr | Phe | Arg | Glu | Cys |
|---|---|---|---|---|---|---|---|---|---|---|---|---|---|---|---|
| | | | 180 | | | | | 185 | | | | | 190 | | |

| Leu | Tyr | Thr | Leu | Lys | Arg | Leu | Val | Asp | Cys | Cys | Ser | Glu | Arg | Leu | Leu |
|---|---|---|---|---|---|---|---|---|---|---|---|---|---|---|---|
| | | 195 | | | | | 200 | | | | | 205 | | | |

| Gly | Lys | Lys | Leu | Gly | Ile | Pro | Arg | Gly | Val | Gln | Arg | Asp | Thr | Met | Trp |
|---|---|---|---|---|---|---|---|---|---|---|---|---|---|---|---|
| | 210 | | | | | 215 | | | | | 220 | | | | |

| Arg | Ile | Phe | Thr | Gly | Ser | Leu | Leu | Val | Glu | Glu | Lys | Ser | Ser | Ala | Leu |
|---|---|---|---|---|---|---|---|---|---|---|---|---|---|---|---|
| 225 | | | | | 230 | | | | | 235 | | | | | 240 |

| Leu | His | Asp | Leu | Arg | Glu | Ile | Glu | Ala | Trp | Ile | Tyr | Arg | Leu | Leu | Arg |
|---|---|---|---|---|---|---|---|---|---|---|---|---|---|---|---|
| | | | | 245 | | | | | 250 | | | | | 255 | |

| Ser | Pro | Val | Pro | Val | Ser | Gly | Gln | Lys | Arg | Val | Asp | Ile | Glu | Val | Leu |
|---|---|---|---|---|---|---|---|---|---|---|---|---|---|---|---|
| | | | 260 | | | | | 265 | | | | | 270 | | |

| Pro | Gln | Glu | Leu | Gln | Pro | Ala | Leu | Thr | Phe | Ala | Leu | Pro | Asp | Pro | Ser |
|---|---|---|---|---|---|---|---|---|---|---|---|---|---|---|---|
| | | 275 | | | | | 280 | | | | | 285 | | | |

| Arg | Phe | Thr | Leu | Val | Asp | Phe | Pro | Leu | His | Leu | Pro | Leu | Glu | Leu | Leu |
|---|---|---|---|---|---|---|---|---|---|---|---|---|---|---|---|
| | 290 | | | | | 295 | | | | | 300 | | | | |

| Gly | Val | Asp | Ala | Cys | Leu | Gln | Val | Leu | Thr | Cys | Ile | Leu | Leu | Glu | His |
|---|---|---|---|---|---|---|---|---|---|---|---|---|---|---|---|
| 305 | | | | | 310 | | | | | 315 | | | | | 320 |

| Lys | Val | Val | Leu | Gln | Ser | Arg | Asp | Tyr | Asn | Ala | Leu | Ser | Met | Ser | Val |
|---|---|---|---|---|---|---|---|---|---|---|---|---|---|---|---|
| | | | | 325 | | | | | 330 | | | | | 335 | |

| Met | Ala | Phe | Val | Ala | Met | Ile | Tyr | Pro | Leu | Glu | Tyr | Met | Phe | Pro | Val |
|---|---|---|---|---|---|---|---|---|---|---|---|---|---|---|---|
| | | | 340 | | | | | 345 | | | | | 350 | | |

| Ile | Pro | Leu | Leu | Pro | Thr | Cys | Met | Ala | Ser | Ala | Glu | Gln | Leu | Leu | Leu |
|---|---|---|---|---|---|---|---|---|---|---|---|---|---|---|---|
| | | 355 | | | | | 360 | | | | | 365 | | | |

| Ala | Pro | Thr | Pro | Tyr | Ile | Ile | Gly | Val | Pro | Ala | Ser | Phe | Phe | Leu | Tyr |
|---|---|---|---|---|---|---|---|---|---|---|---|---|---|---|---|
| | 370 | | | | | 375 | | | | | 380 | | | | |

| Lys | Leu | Asp | Phe | Lys | Met | Pro | Asp | Asp | Val | Trp | Leu | Val | Asp | Leu | Asp |
|---|---|---|---|---|---|---|---|---|---|---|---|---|---|---|---|
| 385 | | | | | 390 | | | | | 395 | | | | | 400 |

```
Ser  Asn  Arg  Val  Ile  Ala  Pro  Thr  Asn  Ala  Glu  Val  Leu  Pro  Ile  Leu
               405                 410                      415

Pro  Glu  Pro  Glu  Ser  Leu  Glu  Leu  Lys  His  Leu  Lys  Gln  Ala  Leu
          420                      425                      430

Ala  Ser  Met  Ser  Leu  Asn  Thr  Gln  Pro  Ile  Leu  Asn  Leu  Glu  Lys  Phe
          435                      440                      445

His  Glu  Gly  Gln  Glu  Ile  Pro  Leu  Leu  Leu  Gly  Arg  Pro  Ser  Asn  Asp
     450                      455                      460

Leu  Gln  Ser  Thr  Pro  Ser  Thr  Glu  Phe  Asn  Pro  Leu  Ile  Tyr  Gly  Asn
465                      470                      475                      480

Asp  Val  Asp  Ser  Val  Asp  Val  Ala  Thr  Arg  Val  Ala  Met  Val  Arg  Phe
               485                      490                      495

Phe  Asn  Ser  Ala  Asn  Val  Leu  Gln  Gly  Phe  Gln  Met  His  Thr  Arg  Thr
               500                      505                      510

Leu  Arg  Leu  Phe  Pro  Arg  Pro  Val  Val  Ala  Phe  Gln  Ala  Gly  Ser  Phe
          515                      520                      525

Leu  Ala  Ser  Arg  Pro  Arg  Gln  Thr  Pro  Phe  Ala  Glu  Lys  Leu  Ala  Arg
     530                      535                      540

Thr  Gln  Ala  Val  Glu  Tyr  Phe  Gly  Glu  Trp  Ile  Leu  Asn  Pro  Thr  Asn
545                      550                      555                      560

Tyr  Ala  Phe  Gln  Arg  Ile  His  Asn  Asn  Met  Phe  Asp  Pro  Ala  Leu  Ile
               565                      570                      575

Gly  Asp  Lys  Pro  Lys  Trp  Tyr  Ala  His  Gln  Leu  Gln  Pro  Ile  His  Tyr
          580                      585                      590

Arg  Val  Tyr  Asp  Ser  Asn  Ser  Gln  Leu  Ala  Glu  Ala  Leu  Ser  Val  Pro
          595                      600                      605

Pro  Glu  Arg  Asp  Ser  Asp  Ser  Glu  Pro  Thr  Asp  Ser  Gly  Ser  Asp
     610                      615                      620

Ser  Met  Asp  Tyr  Asp  Asp  Ser  Ser  Ser  Tyr  Ser  Ser  Leu  Gly  Asp
625                      630                      635                      640

Phe  Val  Ser  Glu  Met  Met  Lys  Cys  Asp  Ile  Asn  Gly  Asp  Thr  Pro  Asn
               645                      650                      655

Val  Asp  Pro  Leu  Thr  His  Ala  Ala  Leu  Gly  Asp  Ala  Ser  Glu  Val  Glu
               660                      665                      670

Ile  Asp  Glu  Leu  Gln  Asn  Gln  Lys  Glu  Ala  Glu  Glu  Pro  Gly  Pro  Asp
          675                      680                      685

Ser  Glu  Asn  Ser  Gln  Glu  Asn  Pro  Pro  Leu  Arg  Ser  Ser  Ser  Thr
     690                      695                      700

Thr  Ala  Ser  Ser  Ser  Pro  Ser  Thr  Val  Ile  His  Gly  Ala  Asn  Ser  Glu
705                      710                      715                      720

Pro  Ala  Asp  Ser  Thr  Glu  Met  Asp  Asp  Lys  Ala  Ala  Val  Gly  Val  Ser
               725                      730                      735

Lys  Pro  Leu  Pro  Ser  Val  Pro  Pro  Ser  Ile  Gly  Lys  Ser  Asn  Met  Asp
          740                      745                      750

Arg  Arg  Gln  Ala  Glu  Ile  Gly  Glu  Gly  Ser  Val  Arg  Arg  Ile  Tyr
     755                      760                      765

Asp  Asn  Pro  Tyr  Phe  Glu  Pro  Gln  Tyr  Gly  Phe  Pro  Glu  Glu  Asp
     770                      775                      780

Glu  Asp  Glu  Gln  Gly  Glu  Ser  Tyr  Thr  Pro  Arg  Phe  Ser  Gln  His  Val
785                      790                      795                      800

Ser  Gly  Asn  Arg  Ala  Gln  Lys  Leu  Leu  Arg  Pro  Asn  Ser  Leu  Arg  Leu
               805                      810                      815

Ala  Ser  Asp  Ser  Asp  Ala  Glu  Ser  Asp  Ser  Arg  Ala  Ser  Ser  Pro  Asn
               820                      825                      830
```

```
Ser Thr Val Ser Asn Thr Ser Thr Glu Gly Phe Gly Gly Ile Met Ser
        835                 840                 845
Phe Ala Ser Ser Leu Tyr Arg Asn His Ser Thr Ser Phe Ser Leu Ser
    850                 855                 860
Asn Leu Thr Leu Pro Thr Lys Gly Ala Arg Glu Lys Ala Thr Pro Phe
865                 870                 875                 880
Pro Ser Leu Lys Gly Asn Arg Arg Ala Leu Val Asp Gln Lys Ser Ser
                885                 890                 895
Val Ile Lys His Ser Pro Thr Val Lys Arg Glu Pro Pro Ser Pro Gln
            900                 905                 910
Gly Arg Ser Ser Asn Ser Ser Glu Asn Gln Gln Phe Leu Lys Glu Val
        915                 920                 925
Val His Ser Val Leu Asp Gly Gln Gly Val Gly Trp Leu Asn Met Lys
    930                 935                 940
Lys Val Arg Arg Leu Leu Glu Ser Glu Gln Leu Arg Val Phe Val Leu
945                 950                 955                 960
Ser Lys Leu Asn Arg Met Val Gln Ser Glu Asp Asp Ala Arg Gln Asp
                965                 970                 975
Ile Ile Pro Asp Val Glu Ile Ser Arg Lys Val Tyr Lys Gly Met Leu
            980                 985                 990
Asp Leu Leu Lys Cys Thr Val Leu Ser Leu Glu Gln Ser Tyr Ala His
        995                 1000                1005
Ala Gly Leu Gly Gly Met Ala Ser Ile Phe Gly Leu Leu Glu Ile Ala
    1010                1015                1020
Gln Thr His Tyr Tyr Ser Lys Glu Pro Asp Lys Arg Lys Arg Ser Pro
1025                1030                1035                1040
Thr Glu Ser Val Asn Thr Pro Val Gly Lys Asp Pro Gly Leu Ala Gly
                1045                1050                1055
Arg Gly Asp Pro Lys Ala Met Ala Gln Leu Arg Val Pro Gln Leu Gly
            1060                1065                1070
Pro Arg Ala Pro Ser Ala Thr Gly Lys Gly Pro Lys Glu Leu Asp Thr
        1075                1080                1085
Arg Ser Leu Lys Glu Glu Asn Phe Ile Ala Ser Ile Gly Pro Glu Val
    1090                1095                1100
Ile Lys Pro Val Phe Asp Leu Gly Glu Thr Glu Glu Lys Lys Ser Gln
1105                1110                1115                1120
Ile Ser Ala Asp Ser Gly Val Ser Leu Thr Ser Ser Ser Gln Arg Thr
                1125                1130                1135
Asp Gln Asp Ser Val Ile Gly Val Ser Pro Ala Val Met Ile Arg Ser
            1140                1145                1150
Ser Ser Gln Asp Ser Glu Val Ser Thr Val Val Ser Asn Ser Ser Gly
        1155                1160                1165
Glu Thr Leu Gly Ala Asp Ser Asp Leu Ser Ser Asn Ala Gly Asp Gly
    1170                1175                1180
Pro Gly Gly Glu Gly Ser Val His Leu Ala Ser Ser Arg Gly Thr Leu
1185                1190                1195                1200
Ser Asp Ser Glu Ile Glu Thr Asn Ser Ala Thr Ser Thr Ile Phe Gly
                1205                1210                1215
Lys Ala His Ser Leu Lys Pro Ser Ile Lys Glu Lys Leu Ala Gly Ser
            1220                1225                1230
Pro Ile Arg Thr Ser Glu Asp Val Ser Gln Arg Val Tyr Leu Tyr Glu
        1235                1240                1245
Gly Leu Leu Gly Lys Glu Arg Ser Thr Leu Trp Asp Gln Met Gln Phe
```

```
                    1250                    1255                     1260
Trp  Glu  Asp  Ala  Phe  Leu  Asp  Ala  Val  Met  Leu  Glu  Arg  Glu  Gly  Met
1265                     1270                    1275                     1280

Gly  Met  Asp  Gln  Gly  Pro  Gln  Glu  Met  Ile  Asp  Arg  Tyr  Leu  Ser  Leu
                    1285                    1290                     1295

Gly  Glu  His  Asp  Arg  Lys  Arg  Leu  Glu  Asp  Glu  Asp  Arg  Leu  Leu
                    1300                    1305                     1310

Ala  Thr  Leu  Leu  His  Asn  Leu  Ile  Ser  Tyr  Met  Leu  Leu  Met  Lys  Val
                    1315                    1320                     1325

Asn  Lys  Asn  Asp  Ile  Arg  Lys  Lys  Val  Arg  Arg  Leu  Met  Gly  Lys  Ser
                    1330                    1335                     1340

His  Ile  Gly  Leu  Val  Tyr  Ser  Gln  Gln  Ile  Asn  Glu  Val  Leu  Asp  Gln
1345                     1350                    1355                     1360

Leu  Ala  Asn  Leu  Asn  Gly  Arg  Asp  Leu  Ser  Ile  Trp  Ser  Ser  Gly  Ser
                    1365                    1370                     1375

Arg  His  Met  Lys  Lys  Gln  Thr  Phe  Val  His  Ala  Gly  Thr  Asp  Thr
                    1380                    1385                     1390

Asn  Gly  Asp  Ile  Phe  Phe  Met  Glu  Val  Cys  Asp  Asp  Cys  Val  Val  Leu
                    1395                    1400                     1405

Arg  Ser  Asn  Ile  Gly  Thr  Val  Tyr  Glu  Arg  Trp  Trp  Tyr  Glu  Lys  Leu
1410                     1415                    1420

Ile  Asn  Met  Thr  Tyr  Cys  Pro  Lys  Thr  Lys  Val  Leu  Cys  Leu  Trp  Arg
1425                     1430                    1435                     1440

Arg  Asn  Gly  Ser  Glu  Thr  Gln  Leu  Asn  Lys  Phe  Tyr  Thr  Lys  Lys  Cys
                    1445                    1450                     1455

Arg  Glu  Leu  Tyr  Tyr  Cys  Val  Lys  Asp  Ser  Met  Glu  Arg  Ala  Ala  Ala
                    1460                    1465                     1470

Arg  Gln  Gln  Ser  Ile  Lys  Pro  Gly  Pro  Glu  Leu  Gly  Gly  Glu  Phe  Pro
                    1475                    1480                     1485

Val  Gln  Asp  Leu  Lys  Thr  Gly  Glu  Gly  Gly  Leu  Leu  Gln  Val  Thr  Leu
                    1490                    1495                     1500

Glu  Gly  Ile  Asn  Leu  Lys  Phe  Met  His  Asn  Gln  Val  Phe  Ile  Glu  Leu
1505                     1510                    1515                     1520

Asn  His  Ile  Lys  Lys  Cys  Asn  Thr  Val  Arg  Gly  Val  Phe  Val  Leu  Glu
                    1525                    1530                     1535

Glu  Phe  Val  Pro  Glu  Ile  Lys  Glu  Val  Val  Ser  His  Lys  Tyr  Lys  Thr
                    1540                    1545                     1550

Pro  Met  Ala  His  Glu  Ile  Cys  Tyr  Ser  Val  Leu  Cys  Leu  Phe  Ser  Tyr
                    1555                    1560                     1565

Val  Ala  Ala  Val  His  Ser  Ser  Glu  Glu  Asp  Leu  Arg  Thr  Pro  Pro  Arg
                    1570                    1575                     1580

Pro  Val  Ser  Ser
1585
```

( 2 ) INFORMATION FOR SEQ ID NO:17:

( i ) SEQUENCE CHARACTERISTICS:
        ( A ) LENGTH: 2473 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 14..2404

( x i ) SEQUENCE DESCRIPTION: SEQ ID NO:17:

```
CCGACGAGGA GACATGGCGG CGGCGCCGGT AGCGGCTGGG TCTGGAGCCG GCCGAGGGAG        60
ACGGTCGGCA GCCACAGTGG CGGCTTGGGG CGGATGGGGC GGCCGGCCGC GGCCTGGTAA       120
CATTCTGCTG CAGCTGCGGC AGGGCCAGCT GACCGGCCGG GGCCTGGTCC GGGCGGTGCA       180
GTTCACTGAG ACTTTTTTGA CGGAGAGGGA CAAACAATCC AAGTGGAGTG GAATTCCTCA       240
GCTGCTCCTC AAGCTGCACA CCACCAGCCA CCTCCACAGT GACTTTGTTG AGTGTCAAAA       300
CATCCTCAAG GAAATTTCTC CTCTTCTCTC CATGGAGGCT ATGGCATTTG TTACTGAAGA       360
GAGGAAACTT ACCCAAGAAA CCACTTATCC AAATACTTAC ATTTTTGACT TGTTTGGAGG       420
TGTTGATCTT CTTGTAGAAA TTCTTATGAG GCCTACGATC TCTATCCGGG ACAGAAACT       480
GAAATAAGT GATGAAATGT CCAAGGACTG CTTGAGTATC CTGTATAATA CCTGTGTCTG       540
TACAGAGGGA GTTACAAAGC GTTTGGCAGA AAAGAATGAC TTTGTGATCT TCCTGTTTAC       600
ATTGATGACA AGTAAGAAGA CATTCTTACA AACAGCAACC CTCATTGAAG ATATTTTAGG       660
TGTTAAAAAG GAAATGATCC GACTAGATGA AGTCCCCAAT CTGAGTTCCT TAGTATCCAA       720
TTTCGATCAG CAGCAGCTCG CTAATTTCTG CCGGATTCTG GCTGTCACCA TTTCAGAGAT       780
GGATACAGGG AATGATGACA AGCACACGCT TCTTGCCAAA AATGCTCAAC AGAAGAAGAG       840
CTTGAGTTTG GGGCCTTCTG CAGCTGAAAT CAATCAAGCG GCCCTTCTCA GCATTCCTGG       900
CTTTGTTGAG CGGCTTTGCA AACTGGCGAC TCGAAAGGTG TCAGAGTCAA CGGGCACAGC       960
CAGCTTCCTT CAGGAGTTGG AAGAGTGGTA CACATGGCTA GACAATGCTT TGGTGCTAGA      1020
TGCCCTGATG CGAGTGGCCA ATGAGGAGTC AGAGCACAAT CAAGCCTCCA TTGTGTTCCC      1080
TCCTCCAGGG GCTTCTGAGG AGAATGGCCT GCCTCACACG TCAGCCAGAA CCCAGCTGCC      1140
CCAGTCAATG AAGATTATGC ATGAGATCAT GTACAAACTG GAAGTGCTCT ATGTCCTCTG      1200
CGTGCTGCTG ATGGGGCGTC AGCGAAACCA GGTTCACAGA ATGATTGCAG AGTTCAAGCT      1260
GATCCCTGGA CTTAATAATT TGTTTGACAA ACTGATTTGG AGGAAGCATT CAGCATCTGC      1320
CCTTGTCCTC CATGGTCACA ACCAGAACTG TGACTGTAGC CCGGACATCA CCTTGAAGAT      1380
ACAGTTTTTG AGGCTTCTTC AGAGCTTCAG TGACCACCAC GAGAACAAGT ACTTGTTACT      1440
CAACAACCAG GAGCTGAATG AACTCAGTGC CATCTCTCTC AAGGCCAACA TCCCTGAGGT      1500
GGAAGCTGTC CTCAACACCG ACAGGAGTTT GGTGTGTGAT GGGAAGAGGG CTTATTAAC      1560
TCGTCTGCTG CAGGTCATGA AGAAGGAGCC AGCAGAGTCG TCTTTCAGGT TTTGGCAAGC      1620
TCGGGCTGTG GAGAGTTTCC TCCGAGGGAC CACCTCCTAT GCAGACCAGA TGTTCCTGCT      1680
GAAGCGAGGC CTCTTGGAGC ACATCCTTTA CTGCATTGTG GACAGCGAGT GTAAGTCAAG      1740
GGATGTGCTC CAGAGTTACT TTGACCTCCT GGGGGAGCTG ATGAAGTTCA ACGTTGATGC      1800
ATTCAAGAGA TTCAATAAAA ATATCAACAC CGATGCAAAG TTCCAGGTAT TCCTGAAGCA      1860
GATCAACAGC TCCCTGGTGG ACTCCAACAT GCTGGTGCGC TGTGTCACTC TGTCCCTGGA      1920
CCGATTTGAA AACCAGGTGG ATATGAAAGT TGCCGAGGTA CTGTCTGAAT GCCGCCTGCT      1980
CGCCTACATA TCCCAGGTGC CCACGCAGAT GTCCTTCCTC TTCCGCCTCA TCAACATCAT      2040
CCACGTGCAG ACGCTGACCC AGGAGAACGT CAGCTGCCTC AACACCAGCC TGGTGATCCT      2100
GATGCTGGCC CGACGGAAAG AGCGGCTGCC CCTGTACCTG CGGCTGCTGC AGCGGATGGA      2160
GCACAGCAAG AAGTACCCCG GCTTCCTGCT CAACAACTTC CACAACCTGC TGCGCTTCTG      2220
GCAGCAGCAC TACCTGCACA AGGACAAGGA CAGCACCTGC CTAGAGAACA GCTCCTGCAT      2280
CAGCTTCTCA TACTGGAAGG AGACAGTGTC CATCCTGTTG AACCCGGACC GGCAGTCACC      2340
```

| | | | | | | | | |
|---|---|---|---|---|---|---|---|---|
| CTCTGCTCTC | GTTAGCTACA | TTGAGGAGCC | CTACATGGAC | ATAGACAGGG | ACTTCACTGA | | | 2400 |
| GGAGTGACCT | TGGGCCAGGC | CTCGGGAGGC | TGCTGGGCCA | GTGTGGGTGA | GCGTGGGTAC | | | 2460 |
| GATGCCACAC | GCC | | | | | | | 2473 |

( 2 ) INFORMATION FOR SEQ ID NO:18:

( i ) SEQUENCE CHARACTERISTICS:
        ( A ) LENGTH: 797 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:18:

```
Met Ala Ala Ala Pro Val Ala Ala Gly Ser Gly Ala Gly Arg Gly Arg
 1               5                  10                  15
Arg Ser Ala Ala Thr Val Ala Ala Trp Gly Gly Trp Gly Gly Arg Pro
            20                  25                  30
Arg Pro Gly Asn Ile Leu Leu Gln Leu Arg Gln Gly Gln Leu Thr Gly
            35                  40                  45
Arg Gly Leu Val Arg Ala Val Gln Phe Thr Glu Thr Phe Leu Thr Glu
50                  55                  60
Arg Asp Lys Gln Ser Lys Trp Ser Gly Ile Pro Gln Leu Leu Leu Lys
65                  70                  75                  80
Leu His Thr Thr Ser His Leu His Ser Asp Phe Val Glu Cys Gln Asn
                85                  90                  95
Ile Leu Lys Glu Ile Ser Pro Leu Leu Ser Met Glu Ala Met Ala Phe
            100                 105                 110
Val Thr Glu Glu Arg Lys Leu Thr Gln Glu Thr Thr Tyr Pro Asn Thr
            115                 120                 125
Tyr Ile Phe Asp Leu Phe Gly Gly Val Asp Leu Leu Val Glu Ile Leu
        130                 135                 140
Met Arg Pro Thr Ile Ser Ile Arg Gly Gln Lys Leu Lys Ile Ser Asp
145                 150                 155                 160
Glu Met Ser Lys Asp Cys Leu Ser Ile Leu Tyr Asn Thr Cys Val Cys
                165                 170                 175
Thr Glu Gly Val Thr Lys Arg Leu Ala Glu Lys Asn Asp Phe Val Ile
            180                 185                 190
Phe Leu Phe Thr Leu Met Thr Ser Lys Lys Thr Phe Leu Gln Thr Ala
        195                 200                 205
Thr Leu Ile Glu Asp Ile Leu Gly Val Lys Lys Glu Met Ile Arg Leu
    210                 215                 220
Asp Glu Val Pro Asn Leu Ser Ser Leu Val Ser Asn Phe Asp Gln Gln
225                 230                 235                 240
Gln Leu Ala Asn Phe Cys Arg Ile Leu Ala Val Thr Ile Ser Glu Met
                245                 250                 255
Asp Thr Gly Asn Asp Asp Lys His Thr Leu Leu Ala Lys Asn Ala Gln
            260                 265                 270
Gln Lys Lys Ser Leu Ser Leu Gly Pro Ser Ala Ala Glu Ile Asn Gln
        275                 280                 285
Ala Ala Leu Leu Ser Ile Pro Gly Phe Val Glu Arg Leu Cys Lys Leu
    290                 295                 300
Ala Thr Arg Lys Val Ser Glu Ser Thr Gly Thr Ala Ser Phe Leu Gln
305                 310                 315                 320
Glu Leu Glu Glu Trp Tyr Thr Trp Leu Asp Asn Ala Leu Val Leu Asp
```

-continued

```
                           325                              330                              335
Ala   Leu   Met   Arg   Val   Ala   Asn   Glu   Glu   Ser   His   Asn   Gln   Ala   Ser
                  340                     345                       350
Ile   Val   Phe   Pro   Pro   Pro   Gly   Ala   Ser   Glu   Glu   Asn   Gly   Leu   Pro   His
                  355                     360                       365
Thr   Ser   Ala   Arg   Thr   Gln   Leu   Pro   Gln   Ser   Met   Lys   Ile   Met   His   Glu
            370                     375                     380
Ile   Met   Tyr   Lys   Leu   Glu   Val   Leu   Tyr   Val   Leu   Cys   Val   Leu   Leu   Met
385                           390                     395                                 400
Gly   Arg   Gln   Arg   Asn   Gln   Val   His   Arg   Met   Ile   Ala   Glu   Phe   Lys   Leu
                        405                     410                           415
Ile   Pro   Gly   Leu   Asn   Asn   Leu   Phe   Asp   Lys   Leu   Ile   Trp   Arg   Lys   His
                  420                     425                           430
Ser   Ala   Ser   Ala   Leu   Val   Leu   His   Gly   His   Asn   Gln   Asn   Cys   Asp   Cys
                  435                     440                           445
Ser   Pro   Asp   Ile   Thr   Leu   Lys   Ile   Gln   Phe   Leu   Arg   Leu   Leu   Gln   Ser
      450                           455                     460
Phe   Ser   Asp   His   His   Glu   Asn   Lys   Tyr   Leu   Leu   Leu   Asn   Asn   Gln   Glu
465                           470                     475                                 480
Leu   Asn   Glu   Leu   Ser   Ala   Ile   Ser   Leu   Lys   Ala   Asn   Ile   Pro   Glu   Val
                        485                     490                           495
Glu   Ala   Val   Leu   Asn   Thr   Asp   Arg   Ser   Leu   Val   Cys   Asp   Gly   Lys   Arg
                  500                     505                           510
Gly   Leu   Leu   Thr   Arg   Leu   Leu   Gln   Val   Met   Lys   Lys   Glu   Pro   Ala   Glu
                  515                     520                           525
Ser   Ser   Phe   Arg   Phe   Trp   Gln   Ala   Arg   Ala   Val   Glu   Ser   Phe   Leu   Arg
      530                           535                     540
Gly   Thr   Thr   Ser   Tyr   Ala   Asp   Gln   Met   Phe   Leu   Leu   Lys   Arg   Gly   Leu
545                           550                     555                                 560
Leu   Glu   His   Ile   Leu   Tyr   Cys   Ile   Val   Asp   Ser   Glu   Cys   Lys   Ser   Arg
                        565                     570                           575
Asp   Val   Leu   Gln   Ser   Tyr   Phe   Asp   Leu   Leu   Gly   Glu   Leu   Met   Lys   Phe
                  580                     585                           590
Asn   Val   Asp   Ala   Phe   Lys   Arg   Phe   Asn   Lys   Asn   Ile   Asn   Thr   Asp   Ala
                  595                     600                           605
Lys   Phe   Gln   Val   Phe   Leu   Lys   Gln   Ile   Asn   Ser   Ser   Leu   Val   Asp   Ser
      610                           615                     620
Asn   Met   Leu   Val   Arg   Cys   Val   Thr   Leu   Ser   Leu   Asp   Arg   Phe   Glu   Asn
625                           630                     635                                 640
Gln   Val   Asp   Met   Lys   Val   Ala   Glu   Val   Leu   Ser   Glu   Cys   Arg   Leu   Leu
                  645                     650                           655
Ala   Tyr   Ile   Ser   Gln   Val   Pro   Thr   Gln   Met   Ser   Phe   Leu   Phe   Arg   Leu
                  660                     665                           670
Ile   Asn   Ile   Ile   His   Val   Gln   Thr   Leu   Thr   Gln   Glu   Asn   Val   Ser   Cys
                  675                     680                           685
Leu   Asn   Thr   Ser   Leu   Val   Ile   Leu   Met   Leu   Ala   Arg   Arg   Lys   Glu   Arg
      690                           695                     700
Leu   Pro   Leu   Tyr   Leu   Arg   Leu   Leu   Gln   Arg   Met   Glu   His   Ser   Lys   Lys
705                           710                     715                                 720
Tyr   Pro   Gly   Phe   Leu   Leu   Asn   Asn   Phe   His   Asn   Leu   Leu   Arg   Phe   Trp
                        725                     730                           735
Gln   Gln   His   Tyr   Leu   His   Lys   Asp   Lys   Asp   Ser   Thr   Cys   Leu   Glu   Asn
                  740                     745                           750
```

-continued

```
Ser  Ser  Cys  Ile  Ser  Phe  Ser  Tyr  Trp  Lys  Glu  Thr  Val  Ser  Ile  Leu
          755                      760                     765

Leu  Asn  Pro  Asp  Arg  Gln  Ser  Pro  Ser  Ala  Leu  Val  Ser  Tyr  Ile  Glu
     770                      775                     780

Glu  Pro  Tyr  Met  Asp  Ile  Asp  Arg  Asp  Phe  Thr  Glu  Glu
785                      790                     795
```

( 2 ) INFORMATION FOR SEQ ID NO:19:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

```
Asp  Tyr  Lys  Asp  Asp  Asp  Asp  Lys
1                   5
```

TNF RECEPTOR DEATH DOMAIN LIGAND PROTEINS

This application is a divisional of application Ser. No. 08/698,551, filed Aug. 15, 1996, (issued as U.S. Pat. No. 5,712,381 on Jan. 27, 1998) which was a continuation-in-part of application Ser. No. 08/602,228, filed Feb. 15, 1996, which was a continuation-in-part of application Ser. No. 08/533,901, filed Sep. 26, 1995, which was a continuation-in-part of application Ser. No. 08/494,440, filed Jun. 19, 1995, which was a continuation-in-part of application Ser. No. 08/327,514, filed Oct. 19, 1994 now abandoned.

BACKGROUND OF THE INVENTION

The present invention relates to the field of anti-inflammatory substances and other substances which act by inhibiting binding to the intracellular domain of a tumor necrosis factor receptor (hereinafter "TNF-R"), such as, for example, the P55 type (or TNF-R1) TNF receptor. More particularly, the present invention is directed to novel ligands which bind to the TNF-R intracellular domain and to inhibition or modulation of signal transduction by this receptor.

Tumor necrosis factor (herein "TNF") is a cytokine which produces a wide range of cellular activities. TNF causes an inflammatory response, which can be beneficial, such as in mounting an immune response to a pathogen, or when overexpressed can lead to other detrimental effects of inflammation.

The cellular effects of TNF are initiated by the binding of TNF to its receptors (TNF-Rs) on the surface of target cells. The isolation of polynucleotides encoding TNF-Rs and variant forms of such receptors has been described in European patent publication Nos. EP 308,378, EP 393,438, EP 433,900, EP 526,905 and EP 568,925; in PCT patent publication Nos. WO91/03553 and WO93/19777; and by Schall et al., Cell 61:361–370 (1990) (disclosing the P55 type TNF receptor). Processes for purification of TNF-Rs have also been disclosed in U.S. Pat. No. 5,296,592.

Native TNF-Rs are characterized by distinct extracellular, transmembrane and intracellular domains. The primary purpose of the extracellular domain is to present a binding site for TNF on the outside of the cell. When TNF is bound to the binding site, a "signal" is transmitted to the inside of the cell through the transmembrane and intracellular domains, indicating that binding has occurred. Transmission or "transduction" of the signal to the inside of the cell occurs by a change in conformation of the transmembrane and/or intracellular domains of the receptor. This signal is "received" by the binding of proteins and other molecules to the intracellular domain of the receptor, resulting in the effects seen upon TNF stimulation. Two distinct TNF receptors of ~55 kd ("TNF-R1") and ~75 kd ("TNF-R2") have been identified. Numerous studies with anti-TNF receptor antibodies have demonstrated that TNF-R1 is the receptor which signals the majority of the pleiotropic activities of TNF. Recently, the domain required for signaling cytotoxicity and other TNF-mediated responses has been mapped to the 80 amino acid near the C-terminus of TNF-R1. This domain is therefore termed the "death domain" (hereinafter referred to as "TNF-R death domain" and "TNF-R1-DD") (see, Tartaglia et al., Cell 74:845–853 (1993)).

While TNF binding by TNF-Rs results in beneficial cellular effects, it is often desirable to prevent or deter TNF binding from causing other detrimental cellular effects. Although substantial effort has been expended investigating inhibition of TNF binding to the extracellular domain of TNF-Rs, examination of binding of proteins and other molecules to the intracellular domain of TNF-Rs has received much less attention.

However, ligands which bind to the TNF-R intracellular domain have yet to be identified. It would be desirable to identify and isolate such ligands to examine their effects upon TNF-R signal transduction and their use as therapeutic agents for treatment of TNF-induced conditions. Furthermore, identification of such ligands would provide a means for screening for inhibitors of TNF-R/intracellular ligand binding, which will also be useful as anti-inflammatory agents.

SUMMARY OF THE INVENTION

Applicants have for the first time identified novel TNF-R1-DD ligand proteins and have isolated polynucleotides encoding such ligands. Applicants have also identified a known protein which may also bind to the death domain of TNF-R.

In one embodiment, the present invention provides a composition comprising an isolated polynucleotide encoding a protein having TNF-R1-DD ligand protein activity. In preferred embodiments, the polynucleotide is selected from the group consisting of:

(a) a polynucleotide comprising the nucleotide sequence of SEQ ID NO:1 from nucleotide 2 to nucleotide 1231;

(b) a polynucleotide comprising a fragment of the nucleotide sequence of SEQ ID NO:1;

(c) a polynucleotide encoding an TNF-R1-DD ligand protein comprising the amino acid sequence of SEQ ID NO:2;

(d) a polynucleotide encoding an TNF-R1-DD ligand protein comprising a fragment of the amino acid sequence of SEQ ID NO:2;

(e) a polynucleotide comprising the nucleotide sequence of SEQ ID NO:3 from nucleotide 2 to nucleotide 415;

(f) a polynucleotide comprising a fragment of the nucleotide sequence of SEQ ID NO:3;

(g) a polynucleotide encoding an TNF-R1-DD ligand protein comprising the amino acid sequence of SEQ ID NO:4;

(h) a polynucleotide encoding an TNF-R1-DD ligand protein comprising a fragment of the amino acid sequence of SEQ ID NO:4;

(i) a polynucleotide comprising the nucleotide sequence of SEQ ID NO:9 from nucleotide 2 to nucleotide 931;

(j) a polynucleotide comprising a fragment of the nucleotide sequence of SEQ ID NO:9;

(k) a polynucleotide encoding an TNF-R1-DD ligand protein comprising the amino acid sequence of SEQ ID NO:10;

(l) a polynucleotide encoding an TNF-R1-DD ligand protein comprising a fragment of the amino acid sequence of SEQ ID NO:10;

(m) a polynucleotide comprising the nucleotide sequence of SEQ ID NO:11 from nucleotide 2 to nucleotide 1822;

(n) a polynucleotide comprising a fragment of the nucleotide sequence of SEQ ID NO:11;

(o) a polynucleotide encoding an TNF-R1-DD ligand protein comprising the amino acid sequence of SEQ ID NO:12;

(p) a polynucleotide encoding an TNF-R1-DD ligand protein comprising a fragment of the amino acid sequence of SEQ ID NO:12;

(q) a polynucleotide comprising the nucleotide sequence of SEQ ID NO:13 from nucleotide 3 to nucleotide 2846;

(r) a polynucleotide comprising a fragment of the nucleotide sequence of SEQ ID NO:13, which encodes a protein having TNF-R1-DD ligand protein activity;

(s) a polynucleotide encoding an TNF-R1-DD ligand protein comprising the amino acid sequence of SEQ ID NO:14;

(t) a polynucleotide encoding an TNF-R1-DD ligand protein comprising a fragment of the amino acid sequence of SEQ ID NO:14 and having TNF-R1-DD ligand protein activity;

(u) a polynucleotide comprising the nucleotide sequence of SEQ ID NO:15 from nucleotide 326 to nucleotide 5092;

(v) a polynucleotide comprising a fragment of the nucleotide sequence of SEQ ID NO:15;

(w) a polynucleotide encoding an TNF-R1-DD ligand protein comprising the amino acid sequence of SEQ ID NO:16;

(x) a polynucleotide encoding an TNF-R1-DD ligand protein comprising a fragment of the amino acid sequence of SEQ ID NO:16;

(y) a polynucleotide comprising the nucleotide sequence of SEQ ID NO:17 from nucleotide 14 to nucleotide 2404;

(z) a polynucleotide comprising a fragment of the nucleotide sequence of SEQ ID NO:17;

(aa) a polynucleotide encoding an TNF-R1-DD ligand protein comprising the amino acid sequence of SEQ ID NO:18;

(bb) a polynucleotide encoding an TNF-R1-DD ligand protein comprising a fragment of the amino acid sequence of SEQ ID NO:18; and (cc) a polynucleotide capable of hybridizing under stringent conditions to any one of the polynucleotides specified in (a)–(cc).

In certain preferred embodiments, the polynucleotide is operably linked to an expression control sequence. The invention also provides a host cell, including bacterial, yeast, insect and mammalian cells, transformed with such polynucleotide compositions.

Processes are also provided for producing an TNF-R1-DD ligand protein, which comprises:

(a) growing a culture of the host cell transformed with such polynucleotide compositions in a suitable culture medium; and (b) purifying the TNF-R1-DD ligand protein from the culture.

The ligand protein produced according to such methods is also provided by the present invention.

Compositions comprising a protein having TNF-R1-DD ligand protein activity are also disclosed. In preferred embodiments the protein comprises an amino acid sequence selected from the group consisting of:

(a) the amino acid sequence of SEQ ID NO:2;

(b) fragments of the amino acid sequence of SEQ ID NO:2;

(c) the amino acid sequence of SEQ ID NO:4;

(d) fragments of the amino acid sequence of SEQ ID NO:4;

(e) the amino acid sequence of SEQ ID NO:6;

(f) fragments of the amino acid sequence of SEQ ID NO:6;

(g) the amino acid sequence of SEQ ID NO:10;

(h) fragments of the amino acid sequence of SEQ ID NO:10;

(i) the amino acid sequence of SEQ ID NO:12;

(j) fragments of the amino acid sequence of SEQ ID NO:12;

(k) the amino acid sequence of SEQ ID NO:14;

(l) fragments of the amino acid sequence of SEQ ID NO: 14;

(m) the amino acid sequence of SEQ ID NO:16;

(n) fragments of the amino acid sequence of SEQ ID NO:16;

(o) the amino acid sequence of SEQ ID NO: 18; and (p) fragments of the amino acid sequence of SEQ ID NO:18;

the protein being substantially free from other mammalian proteins. Such compositions may further comprise a pharmaceutically acceptable carrier.

Compositions comprising an antibody which specifically reacts with such TNF-R1-DD ligand protein are also provided by the present invention.

Methods are also provided for identifying an inhibitor of TNF-R death domain binding which comprise:

(a) combining an TNF-R death domain protein with an TNF-R1-DD ligand protein, said combination forming a first binding mixture;

(b) measuring the amount of binding between the TNF-R death domain protein and the TNF-R1-DD ligand protein in the first binding mixture;

(c) combining a compound with the TNF-R death domain protein and an TNF-R1-DD ligand protein to form a second binding mixture;

(d) measuring the amount of binding in the second binding mixture; and (e) comparing the amount of binding in the first binding mixture with the amount of binding in the second binding mixture;

wherein the compound is capable of inhibiting TNF-R death domain binding when a decrease in the amount of binding of the second binding mixture occurs. In certain preferred embodiments the TNF-R1-DD ligand protein used in such method comprises an amino acid sequence selected from the group consisting of:

(a) the amino acid sequence of SEQ ID NO:2;

(b) fragments of the amino acid sequence of SEQ ID NO:2;

(c) the amino acid sequence of SEQ ID NO:4;

(d) fragments of the amino acid sequence of SEQ ID NO:4;

(e) the amino acid sequence of SEQ ID NO:6;

(f) fragments of the amino acid sequence of SEQ ID NO:6;

(g) the amino acid sequence of SEQ ID NO:8;

(h) fragments of the amino acid sequence of SEQ ID NO:8

(i) the amino acid sequence of SEQ ID NO: 10;

(j) fragments of the amino acid sequence of SEQ ID NO:10;

(k) the amino acid sequence of SEQ ID NO:12;

(l) fragments of the amino acid sequence of SEQ ID NO:12;

(m) the amino acid sequence of SEQ ID NO:14;

(n) fragments of the amino acid sequence of SEQ ID NO:14;
(o) the amino acid sequence of SEQ ID NO:16;
(p) fragments of the amino acid sequence of SEQ ID NO:16;
(q) the amino acid sequence of SEQ ID NO:18;
(r) fragments of the amino acid sequence of SEQ ID NO:18.

Compositions comprising inhibitors identified according to such method are also provided. Such compositions may include pharmaceutically acceptable carriers.

Methods are also provided for preventing or ameliorating an inflammatory condition which comprises administering a therapeutically effective amount of a composition comprising a protein having TNF-R1-DD ligand protein activity and a pharmaceutically acceptable carrier.

Other embodiments provide methods of inhibiting TNF-R death domain binding comprising administering a therapeutically effective amount of a composition comprising a protein having TNF-R1-DD ligand protein activity and a pharmaceutically acceptable carrier.

Methods are also provided for preventing or ameliorating an inflammatory condition which comprises administering to a mammalian subject a therapeutically effective amount of a composition comprising a pharmaceutically acceptable carrier and a protein selected from the group consisting of insulin-like growth factor binding protein-5 ("IGFBP-5"), and fragments thereof having TNF-R1-DD ligand protein activity. Such proteins may also be administered for inhibiting TNF-R death domain binding.

Methods of preventing or ameliorating an inflammatory condition or of inhibiting TNF-R death domain binding are provided, which comprise administering to a mammalian subject a therapeutically effective amount of inhibitors of TNF-R death domain binding, are also provided.

Methods of identifying an inhibitor of TNF-R death domain binding are also provided by the present invention which comprise:

(a) transforming a cell with a first polynucleotide encoding an TNF-R death domain protein, a second polynucleotide encoding an TNF-R1-DD ligand protein, and at least one reporter gene, wherein the expression of the reporter gene is regulated by the binding of the TNF-R1-DD ligand protein encoded by the second polynucleotide to the TNF-R death domain protein encoded by the first polynucleotide;

(b) growing the cell in the presence of and in the absence of a compound; and (c) comparing the degree of expression of the reporter gene in the presence of and in the absence of the compound;

wherein the compound is capable of inhibiting TNF-R death domain binding when a decrease in the degree of expression of the reporter gene occurs. In preferred embodiments, the cell is a yeast cell and the second polynucleotide is selected from the group consisting of:

(a) a polynucleotide comprising the nucleotide sequence of SEQ ID NO:1 from nucleotide 2 to nucleotide 1231;
(b) a polynucleotide comprising a fragment of the nucleotide sequence of SEQ ID NO:1, which encodes a protein having TNF-R1-DD ligand protein activity;
(c) a polynucleotide encoding an TNF-R1-DD ligand protein comprising the amino acid sequence of SEQ ID NO:2;
(d) a polynucleotide encoding an TNF-R1-DD ligand protein comprising a fragment of the amino acid sequence of SEQ ID NO:2 and having TNF-R1-DD ligand protein activity;
(e) a polynucleotide comprising the nucleotide sequence of SEQ ID NO:3 from nucleotide 2 to nucleotide 415;
(f) a polynucleotide comprising a fragment of the nucleotide sequence of SEQ ID NO:3, which encodes a protein having TNF-R1-DD ligand protein activity;
(g) a polynucleotide encoding an TNF-R1-DD ligand protein comprising the amino acid sequence of SEQ ID NO:4;
(h) a polynucleotide encoding an TNF-R1-DD ligand protein comprising a fragment of the amino acid sequence of SEQ ID NO:4 and having TNF-R1-DD ligand protein activity;
(i) a polynucleotide comprising the nucleotide sequence of SEQ ID NO:5 from nucleotide 2 to nucleotide 559;
(j) a polynucleotide comprising a fragment of the nucleotide sequence of SEQ ID NO:5, which encodes a protein having TNF-R1-DD ligand protein activity;
(k) a polynucleotide encoding an TNF-R1-DD ligand protein comprising the amino acid sequence of SEQ ID NO:6;
(l) a polynucleotide encoding an TNF-R1-DD ligand protein comprising a fragment of the amino acid sequence of SEQ ID NO:6 and having TNF-R1-DD ligand protein activity;
(m) a polynucleotide comprising the nucleotide sequence of SEQ ID NO:7 from nucleotide 57 to nucleotide 875;
(n) a polynucleotide comprising a fragment of the nucleotide sequence of SEQ ID NO:7, which encodes a protein having TNF-R1-DD ligand protein activity;
(o) a polynucleotide encoding an TNF-R1-DD ligand protein comprising the amino acid sequence of SEQ ID NO:8;
(p) a polynucleotide encoding an TNF-R1-DD ligand protein comprising a fragment of the amino acid sequence of SEQ ID NO:8 and having TNF-R1-DD ligand protein activity;
(q) a polynucleotide comprising the nucleotide sequence of SEQ ID NO:9 from nucleotide 2 to nucleotide 931;
(r) a polynucleotide comprising a fragment of the nucleotide sequence of SEQ ID NO:9;
(s) a polynucleotide encoding an TNF-R1-DD ligand protein comprising the amino acid sequence of SEQ ID NO:10;
(t) a polynucleotide encoding an TNF-R1-DD ligand protein comprising a fragment of the amino acid sequence of SEQ ID NO:10;
(u) a polynucleotide comprising the nucleotide sequence of SEQ ID NO:11 from nucleotide 2 to nucleotide 1822;
(v) a polynucleotide comprising a fragment of the nucleotide sequence of SEQ ID NO:11;
(w) a polynucleotide encoding an TNF-R1-DD ligand protein comprising the amino acid sequence of SEQ ID NO:12;
(x) a polynucleotide encoding an TNF-R1-DD ligand protein comprising a fragment of the amino acid sequence of SEQ ID NO:12;
(y) a polynucleotide comprising the nucleotide sequence of SEQ ID NO:13 from nucleotide 3 to nucleotide 2846;
(z) a polynucleotide comprising a fragment of the nucleotide sequence of SEQ ID NO:13, which encodes a protein having TNF-R1-DD ligand protein activity;

(aa) a polynucleotide encoding an TNF-R1-DD ligand protein comprising the amino acid sequence of SEQ ID NO:14;

(bb) a polynucleotide encoding an TNF-R1-DD ligand protein comprising a fragment of the amino acid sequence of SEQ ID NO:14 and having TNF-R1-DD ligand protein activity;

(cc) a polynucleotide comprising the nucleotide sequence of SEQ ID NO:15 from nucleotide 326 to nucleotide 5092;

(dd) a polynucleotide comprising a fragment of the nucleotide sequence of SEQ ID NO:15, which encodes a protein having TNF-R1-DD ligand protein activity;

(ee) a polynucleotide encoding an TNF-R1-DD ligand protein comprising the amino acid sequence of SEQ ID NO:16;

(ff) a polynucleotide encoding an TNF-R1-DD ligand protein comprising a fragment of the amino acid sequence of SEQ ID) NO:16 and having TNF-R1-DD ligand protein activity;

(gg) a polynucleotide comprising the nucleotide sequence of SEQ ID NO:17 from nucleotide 14 to nucleotide 2404;

(hh) a polynucleotide comprising a fragment of the nucleotide sequence of SEQ ID NO:17, which encodes a protein having TNF-R1-DD ligand protein activity;

(ii) a polynucleotide encoding an TNF-R1-DD ligand protein comprising the amino acid sequence of SEQ ID NO:18;

(jj) a polynucleotide encoding an TNF-R1-DD ligand protein comprising a fragment of the amino acid sequence of SEQ ID NO:18 and having TNF-R1-DD ligand protein activity; and (kk) a polynucleotide capable of hybridizing under stringent conditions to any one of the polynucleotides specified in (a)–(jj), which encodes a protein having TNF-R1-DD ligand protein activity.

BRIEF DESCRIPTION OF THE FIGURES

FIGS. 1 and 2 depict autoradiographs demonstrating the expression of TNF-R1-DD ligand proteins of the present invention.

FIG. 4 demonstrates the binding of 1TU and 27TU to TNF-R1-DD. MBP, MBP-1TU or MBP-27TU (3 µg) was incubated with glutathione beads containing 3 µg of either GST or GST-TNF-R1-DD in 100 µl of binding buffer (0.2% Triton, 20 mM Tris pH 7.5, 140 mM NaCl, 0.1 mM EDTA, 10 mM DTT and 5% glycerol). The reaction ws performed at 4° C. for 2 hours and centrifuged to remove unbound fraction (Unbound). The beads were then washed with 500 µl binding buffer four times and resuspended into SDS-sample buffer (Bound). These samples were analyzed by Western blot using anti-MBP antibody (New England Biolab).

DETAILED DESCRIPTION OF THE INVENTION

Figure 1:
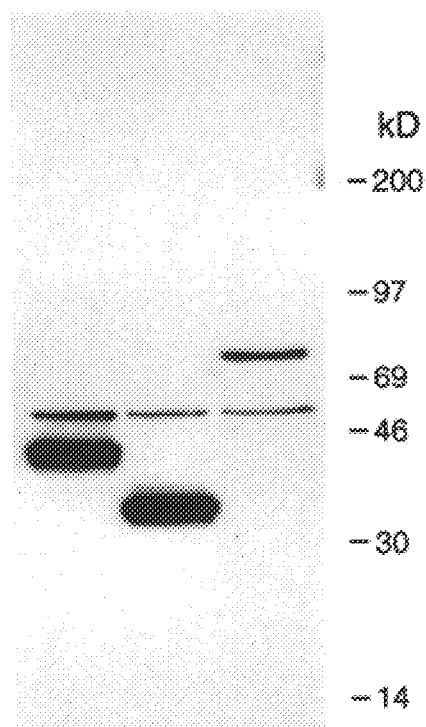

The present inventors have for the first time identified and isolated novel polynucleotides which encode proteins which bind to the TNF-R death domain. As used herein "TNF-R" includes all receptors for tumor necrosis factor. The P55 type TNF-R is the preferred receptor for practicing the present invention.

The sequence of a polynucleotide encoding one such protein is set forth in SEQ ID NO:1 from nucleotides 2 to 1231. This polynucleotide has been identified as "clone 2DD" The amino acid sequence of the TNF-R1-DD ligand protein encoded by clone 2DD is set forth in SEQ ID NO:2. It is believed that clone 2DD is a partial cDNA clone of a longer full length coding sequence. However, as demonstrated herein the protein encoded by clone 2DD does bind the death domain of TNF-R (i.e., has "TNF-R1-DD ligand protein activity" as defined herein). Clone 2DD was deposited with the American Type Culture Collection on Oct. 13, 1994 and given the accession number ATCC 69706.

The protein encoded by clone 2DD is 410 amino acids in length. No identical or closely related sequences were found using BLASTN/BLASTX or FASTA searches. Therefore, clone 2DD encodes a novel protein.

The sequence of a polynucleotide encoding one such protein is set forth in SEQ ID NO:3 from nucleotides 2 to 415. This polynucleotide has been identified as "clone 3DD". The amino acid sequence of the TNF-R1-DD ligand protein encoded by clone 3DD is set forth in SEQ ID NO:4. It is believed that clone 3DD is a partial cDNA clone of a longer full length coding sequence. However, as demonstrated herein the protein encoded by clone 3DD does bind the death domain of TNF-R (i.e., has "TNF-R1-DD ligand protein activity" as defined herein). Clone 3DD was deposited with the American Type Culture Collection on Oct. 13, 1994 and given the accession number ATCC 69705.

The protein encoded by clone 3DD is 138 amino acids. No identical or closely related sequences were found using BLASTN/BLASTX or FASTA searches. Therefore, clone 3DD encodes a novel protein.

A full-length clone corresponding to clone 3DD was also isolated and identified as "clone 3TW". The nucleotide sequence of clone 3TW is reported as SEQ ID NO:13. Nucleotides 3 to 2846 of SEQ ID NO:13 encode a TNF-R1-DD ligand protein, the amino acid sequence of which is reported as SEQ ID NO:14. Amino acids 811 to 948 of SEQ ID NO:14 correspond to amino acids 1 to 138 of SEQ ID NO:4 (clone 3DD). Clone 3TW was deposited with the American Type Culture Collection on Sep. 26, 1995 and given the accession number ATCC 69904.

The sequence of a polynucleotide encoding another such protein is set forth in SEQ ID NO:5 from nucleotides 2 to 559. This polynucleotide has been identified as "clone 20DD." The amino acid sequence of the TNF-R1-DD ligand protein encoded by clone 20DD is set forth in SEQ ID NO:6. It is believed that clone 20DD is a partial cDNA clone of a longer full length coding sequence. However, as demonstrated herein the protein encoded by clone 20DD does bind the death domain of TNF-R (i.e., has "TNF-R1-DD ligand protein activity" as defined herein). Clone 20DD was deposited with the American Type Culture Collection on Oct. 13, 1994 and given the accession number ATCC 69704.

The protein encoded by clone 20DD is identical to amino acids 87 to 272 of insulin-like growth factor binding protein-5 ("IGFBP-5"), a sequence for which was disclosed in J. Biol. Chem. 266:10646–10653 (1991) by Shimasaki et al., which is incorporated herein by reference. The polynucleotide and amino acid sequences of IGFBP-5 are set forth in SEQ ID NO:7 and SEQ ID NO:8, respectively. Based upon the sequence identity between clone 20DD and IGFBP-5, IGFBP-5 and certain fragments thereof will exhibit TNF-R1-DD ligand binding activity (as defined herein).

The sequence of a polynucleotide encoding another such protein is set forth in SEQ ID NO:9 from nucleotides 2 to 931. This polynucleotide has been identified as "clone 1TU" The amino acid sequence of the TNF-R1-DD ligand protein encoded by clone 1TU is set forth in SEQ ID NO:10. It is believed that clone 1TU is a partial cDNA clone of a longer full length coding sequence. However, as demonstrated herein the protein encoded by clone 1TU does bind the death domain of TNF-R (i.e., has "TNF-R1-DD ligand protein activity" as defined herein). Clone 1TU was deposited with the American Type Culture Collection on Jun. 7, 1995 and given the accession number ATCC 69848.

The protein encoded by clone 1TU is 310 amino acids in length. No identical or closely related sequences were found using BLASTN/BLASTX or FASTA searches. Therefore, clone 1TU encodes a novel protein.

The sequence of a polynucleotide encoding another such protein is set forth in SEQ ID NO:11 from nucleotides 2 to 1822. This polynucleotide has been identified as "clone 27TU" The amino acid sequence of the TNF-R1-DD ligand protein encoded by clone 27TU is set forth in SEQ ID NO:12. It is believed that clone 27TU is a partial cDNA clone of a longer full length coding sequence. However, as demonstrated herein the protein encoded by clone 27TU does bind the death domain of TNF-R (i.e., has "TNF-R1-DD ligand protein activity" as defined herein). Clone 27TU was deposited with the American Type Culture Collection on Jun. 7, 1995 and given the accession number ATCC 69846.

The protein encoded by clone 27TU is 607 amino acids in length. No identical or closely related sequences were found using BLASTN/BLASTX or FASTA searches. Therefore, clone 27TU encodes a novel protein. 27TU may be a longer version of clone 2DD. 2DD encodes the same amino acid sequence (SEQ ID NO:2) as amino acids 198–607 encoded by 27TU (SEQ ID NO:12). The nucleotide sequences of 2DD and 27TU are also identical within this region of identity.

An additional "clone 15TU" was isolated which encoded a portion of the 27TU sequence (approximately amino acids 289–607 of SEQ ID NO: 12). Clone 15TU was deposited with the American Type Culture Collection on Jun. 7, 1995 and given the accession number ATCC 69847. 15TU comprises the same nucleotide sequence as 27TU over this region of amino acids.

A full-length clone corresponding to clone 27TU was also isolated and identified as "clone 57TU4A". The nucleotide sequence of clone 57TU4A is reported as SEQ ID NO:15. Nucleotides 336 to 5092 of SEQ ID NO:15 encode a TNF-R1 -DD ligand protein, the amino acid sequence of which is reported as SEQ ID NO:146 Amino acids 982 to 1588 of SEQ ID NO:16 correspond to amino acids 1 to 607 of SEQ ID NO:12 (clone 27TU). Clone 57TU4A was deposited with the American Type Culture Collection on Feb. 13, 1996 and given the accession number ATCC 69988.

A full-length clone corresponding to clone 1TU was also isolated and identified as "clone 33-1B". The nucleotide sequence of clone 33-1B is reported as SEQ ID NO:17. Nucleotides 14 to 2404 of SEQ ID NO:17 encode a TNF-R1-DD ligand protein, the amino acid sequence of which is reported as SEQ ID NO:18. Amino acids 488 to 797 of SEQ ID NO:18 correspond to amino acids 1 to 310 of SEQ ID NO:10 (clone 1TU). Clone 33-1B was deposited with the American Type Culture Collection on Aug. 13, 1996 and given the accession number ATCC 98137.

Polynucleotides hybridizing to the polynucleotides of the present invention under stringent conditions and highly stringent conditions are also part of the present invention. As used herein, "highly stringent conditions" include, for example, 0.2×SSC at 65° C.; and "stringent conditions" include, for example, 4×SSC at 65° C. or 50% formamide and 4×SSC at 42° C.

For the purposes of the present application, "TNF-R1-DD ligand protein" includes proteins which exhibit TNF-R1-DD ligand protein activity. For the purposes of the present application, a protein is defined as having "TNF-R1-DD ligand protein activity" when it binds to a protein derived from the TNF-R death domain. Activity can be measured by using any assay which will detect binding to an TNF-R death domain protein. Examples of such assays include without limitation the interaction trap assays and assays in which TNF-R death domain protein which is affixed to a surface in a manner conducive to observing binding, including without limitation those described in Examples 1 and 3. As used herein an "TNF-R death domain protein" includes the entire death domain or fragments thereof.

Fragments of the TNF-R1-DD ligand protein which are capable of interacting with the TNF-R death domain or which are capable of inhibiting TNF-R death domain binding (i.e., exhibit TNF-R1-DD ligand protein activity) are also encompassed by the present invention. Fragments of the TNF-R1-DD ligand protein may be in linear form or they may be cyclized using known methods, for example, as described in H. U. Saragovi, et al., Bio/Technology 10, 773–778 (1992) and in R. S. McDowell, et al., J. Amer. Chem. Soc. 114, 9245–9253 (1992), both of which are incorporated herein by reference. Such fragments may be fused to carrier molecules such as immunoglobulins for many purposes, including increasing the valency of TNF-R1-DD ligand protein binding sites. For example, fragments of the TNF-R1-DD ligand protein may be fused through "linker" sequences to the Fc portion of an immunoglobulin. For a bivalent form of the TNF-R1-DD ligand protein, such a fusion could be to the Fc portion of an IgG molecule. Other immunoglobulin isotypes may also be used to generate such fusions. For example, an TNF-R1-DD ligand protein—IgM fusion would generate a decavalent form of the TNF-R1-DD ligand protein of the invention.

The isolated polynucleotide of the invention may be operably linked to an expression control sequence such as the pMT2 or pED expression vectors disclosed in Kaufman et al., Nucleic Acids Res. 19, 4485–4490 (1991), in order to produce the TNF-R1-DD ligand protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and the expression control sequence are situated within a vector or cell in such a way that the TNF-R1-DD ligand protein is expressed by a host cell which has been transformed (transfected) with the ligated polynucleotide/expression control sequence.

A number of types of cells may act as suitable host cells for expression of the TNF-R1-DD ligand protein. Host cells include, for example, monkey COS cells, Chinese Hamster Ovary (CHO) cells, human kidney 293 cells, human epidermal A43 1 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

The TNF-R1-DD ligand protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No.* 1555 (1987), incorporated herein by reference.

Alternatively, it may be possible to produce the TNF-R1-DD ligand protein in lower eukaryotes such as yeast or in prokaryotes such as bacteria. Potentially suitable yeast strains include *Saccharomyces cerevisiae, Schizosaccharomyces pombe,* Kluyveromyces strains, Candida, or any yeast strain capable of expressing heterologous proteins. Potentially suitable bacterial strains include *Escherichia coli, Bacillus subtilis, Salmonella typhimurium,* or any bacterial strain capable of expressing heterologous proteins. If the TNF-R1-DD ligand protein is made in yeast or bacteria, it may be necessary to modify the protein produced therein, for example by phosphorylation or glycosylation of the appropriate sites, in order to obtain the functional TNF-R1-DD ligand protein. Such covalent attachments may be accomplished using known chemical or enzymatic methods.

The TNF-R1-DD ligand protein of the invention may also be expressed as a product of transgenic animals, e.g., as a component of the milk of transgenic cows, goats, pigs, or sheep which are characterized by somatic or germ cells containing a nucleotide sequence encoding the TNF-R1-DD ligand protein.

The TNF-R1-DD ligand protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the TNF-R1-DD ligand protein may also include an affinity column containing the TNF-R death domain or other TNF-R death domain protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, the TNF-R1-DD ligand protein of the invention may also be expressed in a form which will facilitate purification. For example, it may be expressed as a fusion protein, such as those of maltose binding protein (MBP) or glutathione-S-transferase (GST). Kits for expression and purification of such fusion proteins are commercially available from New England BioLab (Beverly, Mass.) and Pharmacia (Piscataway, N.J.), respectively. The TNF-R ligand protein can also be tagged with an epitope and subsequently purified by using a specific antibody directed to such epitope. One such epitope ("Flag") is commercially available from Kodak (New Haven, CT).

Finally, one or more reverse-phase high performance liquid chromatography (RP-HPLC) steps employing hydrophobic RP-HPLC media, e.g., silica gel having pendant methyl or other aliphatic groups, can be employed to further purify the TNF-R1-DD ligand protein. Some or all of the foregoing purification steps, in various combinations, can also be employed to provide a substantially homogeneous isolated recombinant protein. The TNF-R1-DD ligand protein thus purified is substantially free of other mammalian proteins and is defined in accordance with the present invention as an "isolated TNF-R1-DD ligand protein."

TNF-R1-DD ligand proteins may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with TNF-R1-DD ligand proteins may possess biological properties in common therewith, including TNF-R1-DD ligand protein activity. Thus, they may be employed as biologically active or immunological substitutes for natural, purified TNF-R1-DD ligand proteins in screening of therapeutic compounds and in immunological processes for the development of antibodies.

The TNF-R1-DD ligand proteins provided herein also include proteins characterized by amino acid sequences similar to those of purified TNF-R1-DD ligand proteins but into which modification are naturally provided or deliberately engineered. For example, modifications in the peptide or DNA sequences can be made by those skilled in the art using known techniques. Modifications of interest in the TNF-R1-DD ligand protein sequences may include the replacement, insertion or deletion of a selected amino acid residue in the coding sequence. For example, one or more of the cysteine residues may be deleted or replaced with another amino acid to alter the conformation of the molecule. Mutagenic techniques for such replacement, insertion or deletion are well known to those skilled in the art (see, e.g., U.S. Pat. No. 4,518,584).

Other fragments and derivatives of the sequences of TNF-R1-DD ligand proteins which would be expected to retain TNF-R1-DD ligand protein activity in whole or in part and may thus be useful for screening or other immunological methodologies may also be easily made by those skilled in the art given the disclosures herein. Such modifications are believed to be encompassed by the present invention.

TNF-R1-DD ligand protein of the invention may also be used to screen for agents which are capable of inhibiting or blocking binding of an TNF-R1-DD ligand protein to the death domain of TNF-R, and thus may act as inhibitors of TNF-R death domain binding and/or TNF activity. Binding assays using a desired binding protein, immobilized or not, are well known in the art and may be used for this purpose using the TNF-R1-DD ligand protein of the invention. Examples 1 and 3 describe examples of such assays. Appropriate screening assays may be cell-based or cell-free. Alternatively, purified protein based screening assays may be used to identify such agents. For example, TNF-R1-DD ligand protein may be immobilized in purified form on a carrier and binding to purified TNF-R death domain may be measured in the presence and in the absence of potential inhibiting agents. A suitable binding assay may alternatively employ purified TNF-R death domain immobilized on a carrier, with a soluble form of a TNF-R1-DD ligand protein of the invention. Any TNF-R1-DD ligand protein may be used in the screening assays described above.

In such a screening assay, a first binding mixture is formed by combining TNF-R death domain protein and TNF-R1-DD ligand protein, and the amount of binding in the first binding mixture ($B_o$) is measured. A second binding mixture is also formed by combining TNF-R death domain protein, TNF-R1-DD ligand protein, and the compound or agent to be screened, and the amount of binding in the second binding mixture (B) is measured. The amounts of binding in the first and second binding mixtures are compared, for example, by performing a $B/B_o$ calculation. A compound or agent is considered to be capable of inhibiting TNF-R death domain binding if a decrease in binding in the second binding mixture as compared to the first binding mixture is observed. The formulation and optimization of binding mixtures is within the level of skill in the art. Such binding mixtures may also contain buffers and salts necessary to enhance or to optimize binding, and additional control assays may be included in the screening assay of the invention.

Alternatively, appropriate screening assays may be cell based. For example, the binding or interaction between an TNF-R ligand protein and the TNF-R death domain can be measured in yeast as described below in Examples 1 and 3.

Compounds found to reduce, preferably by at least about 10%, more preferably greater than about 50% or more, the binding activity of TNF-R1-DD ligand protein to TNF-R death domain may thus be identified and then secondarily screened in other binding assays, including in vivo assays. By these means compounds having inhibitory activity for TNF-R death domain binding which may be suitable as anti-inflammatory agents may be identified.

Isolated TNF-R1-DD ligand protein may be useful in treating, preventing or ameliorating inflammatory conditions and other conditions, such as cachexia, autoimmune disease, graft versus host reaction, osteoporosis, colitis, myelogenous leukemia, diabetes, wasting, and atherosclerosis. Isolated TNF-R1-DD ligand protein may be used itself as an inhibitor of TNF-R death domain binding or to design inhibitors of TNF-R death domain binding. Inhibitors of binding of TNF-R1-DD ligand protein to the TNF-R death domain ("TNF-R intracellular binding inhibitors") are also useful for treating such conditions.

The present invention encompasses both pharmaceutical compositions and therapeutic methods of treatment or use which employ isolated TNF-R1-DD ligand protein and/or binding inhibitors of TNF-R intracellular binding.

Isolated TNF-R1-DD ligand protein or binding inhibitors (from whatever source derived, including without limitation from recombinant and non-recombinant cell lines) may be used in a pharmaceutical composition when combined with a pharmaceutically acceptable carrier. Such a composition may also contain (in addition to TNF-R1-DD ligand protein or binding inhibitor and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-2, IL-3, IL-4, IL-5, IL-6, IL-7, L-8, IL-9, G-CSF, Meg-CSF, stem cell factor, and erythropoietin. The pharmaceutical composition may further contain other anti-inflammatory agents. Such additional factors and/or agents may be included in the pharmaceutical composition to produce a synergistic effect with isolated TNF-R1-DD ligand protein or binding inhibitor, or to minimize side effects caused by the isolated TNF-R1-DD ligand protein or binding inhibitor. Conversely, isolated TNF-R1-DD ligand protein or binding inhibitor may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

The pharmaceutical composition of the invention may be in the form of a liposome in which isolated TNF-R1-DD ligand protein or binding inhibitor is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing, prevention or amelioration of an inflammatory response or condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of isolated TNF-R1-DD ligand protein or binding inhibitor is administered to a mammal having a condition to be treated. Isolated TNF-R1-DD ligand protein or binding inhibitor may be administered in accordance with the method of the invention either alone or in combination with other therapies such as treatments employing cytokines, lymphokines or other hematopoietic factors. When co-administered with one or more cytokines, lymphokines or other hematopoietic factors, isolated TNF-R1-DD ligand protein or binding inhibitor may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering isolated TNF-R1-DD ligand protein or binding inhibitor in combination with cytokine(s), lymphokine(s), other hematopoietic factor(s), thrombolytic or anti-thrombotic factors.

Administration of isolated TNF-R1-DD ligand protein or binding inhibitor used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of isolated TNF-R1-DD ligand protein or binding inhibitor is administered orally, isolated TNF-R1-DD ligand protein or binding inhibitor will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% isolated TNF-R1-DD ligand protein or binding inhibitor, and preferably from about 25 to 90% isolated TNF-R1-DD ligand protein or binding inhibitor. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of isolated TNF-R1-DD ligand protein or binding inhibitor, and preferably from about 1 to 50% isolated TNF-R1-DD ligand protein or binding inhibitor.

When a therapeutically effective amount of isolated TNF-R1-DD ligand protein or binding inhibitor is administered by intravenous, cutaneous or subcutaneous injection, isolated TNF-R1-DD ligand protein or binding inhibitor will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to isolated TNF-R1-DD ligand protein or binding inhibitor, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of isolated TNF-R1-DD ligand protein or binding inhibitor in the pharmaceutical composition of the present invention will depend upon the nature and severity of the condition being treated, and on the nature of prior treatments which the patient has undergone. Ultimately, the attending physician will decide the amount of isolated TNF-R1-DD ligand protein or binding inhibitor with which to treat each individual patient. Initially, the attending physician will administer low doses of isolated TNF-R1-DD ligand protein or binding inhibitor and observe the patient's response. Larger doses of isolated TNF-R1-DD ligand protein or binding inhibitor may be administered until the optimal therapeutic effect is obtained for the patient, and at that point the dosage is not increased further. It is contemplated that the various pharmaceutical compositions used to practice the method of the present invention should contain about 0.1 μg to about 100 mg of isolated TNF-R1-DD ligand protein or binding inhibitor per kg body weight.

The duration of intravenous therapy using the pharmaceutical composition of the present invention will vary, depending on the severity of the disease being treated and the condition and potential idiosyncratic response of each individual patient. It is contemplated that the duration of each application of the isolated TNF-R1-DD ligand protein or binding inhibitor will be in the range of 12 to 24 hours of continuous intravenous administration. Ultimately the attending physician will decide on the appropriate duration of intravenous therapy using the pharmaceutical composition of the present invention.

Isolated TNF-R1-DD ligand protein of the invention may also be used to immunize animals to obtain polyclonal and monoclonal antibodies which specifically react with the TNF-R1-DD ligand protein and which may inhibit TNF-R death domain binding. Such antibodies may be obtained using either the entire TNF-R1-DD ligand protein or fragments of TNF-R1-DD ligand protein as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer.Chem.Soc. 85, 2149–2154 (1963); J. L. Krstenansky, et al., FEBS Lett. 211, 10 (1987).

Monoclonal antibodies binding to TNF-R1-DD ligand protein or to complex carbohydrate moieties characteristic of the TNF-R1-DD ligand glycoprotein may be useful diagnostic agents for the immunodetection of TNF-R ligand protein.

Neutralizing monoclonal antibodies binding to TNF-R1-DD ligand protein or to complex carbohydrates characteristic of TNF-R1-DD ligand glycoprotein may also be useful therapeutics for both inflammatory conditions and also in the treatment of some forms of cancer where abnormal expression of TNF-R1-DD ligand protein is involved. These neutralizing monoclonal antibodies are capable of blocking the signaling function of the TNF-R1-DD ligand protein. By blocking the binding of TNF-R1-DD ligand protein, certain biological responses to TNF are either abolished or markedly reduced. In the case of cancerous cells or leukemic cells, neutralizing monoclonal antibodies against TNF-R1-DD ligand protein may be useful in detecting and preventing the metastatic spread of the cancerous cells, which may be mediated by the TNF-R1-DD ligand protein.

Due to the similarity of their sequences to the insulin growth factor binding protein ("IGFBP-5") and fragments thereof which bind to the TNF-R death domain are proteins having TNF-R1-DD ligand protein activity as defined herein. As a result, they are also useful in pharmaceutical compositions, for treating inflammatory conditions and for inhibiting TNF-R death domain binding as described above for TNF-R1-DD ligand proteins generally.

EXAMPLE 1

CLONING OF TNF-R DEATH DOMAIN LIGAND PROTEIN ENCODING POLYNUCLEOTIDE

A yeast genetic selection method, the "interaction trap" [Gyuris et al, Cell 75:791–803, 1993, which is incorporated herein by reference], was used to screen W138 cell cDNA libraries (preparation, see below) for proteins that interact with the death domain of the P55 type 1 TNF receptor (TNF-R1-DD). A polynucleotide encoding amino acids 326 to 413 of the P55 type TNF receptor, TNF-R1-DD, was obtained via the polymerase chain reaction (PCR) using a grafting method. This TNF-R1-DD DNA was then cloned into pEG202 by BamHI and SalI sites, generating the bait plasmid, pEG202-TNF-R1-DD. This plasmid contains the HIS3 selectable marker, and expression of the bait, the LexA-TNF-R1-DD fusion protein, is from the strong constitutive ADH1 promoter. To create the reporter strain carrying the bait protein, yeast strain EGY48, containing the reporter sequence LexAop-Leu2 in place of the chromosomal LEU2, was transformed with pEG202-TNF-R1-DD and pSH18–b 34 (Ura+), which carries another reporter sequence, LexAop-lacZ. For screening cDNAs encoding proteins that interact with TNF-R1-DD, the expression vector pJG4–5 (TRP1), containing the WI38 cell cDNA library (see below for the cDNA library construction), was transformed into the above strain (EGY48/pEG202-TNF-R1-DD/pSH 18–34) according to the method described by Gietz et al., Nucleic Acids Res., 20:1425 (1992).

cDNA Library Construction:

WI38 cell cDNA library: Double stranded cDNA was prepared from 3 ug of WI38 mRNA using reagents provided by the Superscript Choice System (Gibco/BRL, Gaithersberg, Md.) with the following substitutions: the first strand synthesis was primed using an oligo dT/XhoI primer/linker, and the dNTP mix was substituted with a mix containing methyl dCTP (Stratagene, Lajolla, Calif.). The cDNA was modified at both ends by addition of an EcoRI/NotI/SalI adapter linker and subsequently digested with XhoI. This produced cDNA molecules possessing an EcoRI/NotI/SalI overhang at the 5' end of the gene and an XhoI overhang at the 3' end. These fragments were then ligated into the yeast expression/fusion vector pJG4–5 (Gyuris et al., Cell, 75, 791–803, 1993), which contains at its amino terminus, the influenza virus HA1 epitope tag, the B42 acidic transcription activation domain, and the SV40 nuclear localization signal, all under the control of the galactose-dependent GAL1 promoter. The resulting plasmids were then electroporated into DH10B cells (Gibco/BRL). A total of $7.1 \times 10^6$ colonies were plated on LB plates containing 100 ug/ml of ampicillin. These E.coli were scraped, pooled, and a large scale plasmid prep was performed using the Wizard Maxi Prep kit (Promega, Madison, Wis.), yielding 3.2 mg of supercoiled plasmid DNA.

WI38 Cell cDNA Screening Results:

$1 \times 10^6$ transformants were obtained on glucose Ura His Trp plates. These transformants were pooled and resuspended in a solution of 65% glycerol, 10 mM Tris-HCl (pH 7.5), 10 mM $MgCl_2$ and stored at $-80°$ C. in 1 mL aliquots. For screening purposes, aliquots of these were diluted 10-fold into Ura$^-$His$^-$Trp$^-$ CM dropout gal/raff medium (containing 2% galactose, 1% raffinose), which induces the expresssion of the library encoded proteins, and incubated at 30° C. for 4 hours. $12 \times 10^6$ colony forming units (CFUs) were then plated on standard 10 cm galactose X-Gal Ura$^-$His$^-$Trp$^-$Leu$^-$ plates at a density of $2 \times 10^5$ CFU/plate. After three days at 30° C., about 1,000 colonies were formed (Leu$^+$) and of those, sixty-four colonies were LacZ$^+$. In order to test if the Leu$^+$/LacZ$^+$ phenotype was due to the library-encoded protein, the galactose dependency of the phenotype was tested. Expression of the library-encoded proteins was turned off by growth on glucose Ura$^-$His Trp master plates and then retested for galactose-dependency on glucose Ura$^-$His$^-$Trp$^-$Leu$^-$, galactose Ura$^-$His$^-$Trp$^-$Leu$^-$, glucose X-Gal Ura$^-$His$^-$Trp$^-$, and galactose X-Gal Ura$^-$His$^-$Trp$^-$ plates. Of these, 32 colonies showed galactose-dependent growth on Leu$^-$ plates and galactose-dependent blue color on X-Gal-containing medium (LacZ$^+$phenotype). Total yeast DNA was prepared from these colonies according to the method described previously (Hoffman and Winston, 1987). In order to analyze the cDNA sequences, PCR reactions were performed using the above yeast DNA as a template and oligo primers specific for the vector pJG4–5, flanking the cDNA insertion point. PCR products were purified (Qiagen PCR purification kit), subjected to restriction digest with the enzyme HaeIII, run on 1.8% agarose gels, and the restriction patterns compared. Similar and identical restriction patterns were grouped and representatives of each group were sequenced and compared to Genbank and other databases to identify any sequence homologies.

One clone of unique sequence ("2DD") and three clones with identical sequence ("3DD") were isolated and showed no signficant sequence homologies compared to Genbank and other databases. Additionally, four other clones ("20DD") with identical sequence to a portion of human insulin-like growth factor binding protein-5 (Shunichi Shimasaki et al., J. Biol. Chem. 266:10646–10653 (1991)) were isolated. The clones "2DD", "3DD" and "20DD" were chosen for further analysis. Library vector pJG4–5 containing these clones sequences were rescued from yeast by transforming the total yeast DNAs into the E. coli strain KC8 and selecting for growth on Trp-ampicillin plates. These putative TNFR1 interacting proteins were then tested further for specificity of interaction with the TNF-R1-DD by the reintroduction of JG4–5 clone into EGY48 derivatives containing a panel of different baits, including bicoid, the cytoplasmic domain of the IL-1 receptor, and TNF-R1-DD. The above clones were found to interact only with the TNF-R1-DD. The interaction between these clones and TNF-R1-DD was thus judged to be specific.

U937 cDNA Screening Results:

A U937 cDNA library was also constructed and screened as described above. 1,020 Leu+ colonies were found and of those, 326 colonies were also LacZ+. 62 colonies of these Leu+/LacZ+ colonies showed a galactose-dependent phenotype. One of these clones, 1TU, encodes a novel sequence. Interestingly, two clones, 15TU and 27TU, encode related or identical sequences, except that 27TU contains about 864 additional nucleotides (or about 288 amino acids) at the 5' end. 15/27TU also encode a novel sequence.

EXAMPLE 2

EXPRESSION OF THE TNF-R1-DD ligand PROTEIN cDNAs encoding TNF-R intracellular ligand proteins were released from the pJG4–5 vector with the appropriate restriction enzymes. For example, EcoRI and XhoI or NotI and XhoI were used to release cDNA from clone 2DD and clone 20DD. Where the restriction sites were also present in the internal sequence of the cDNA, PCR was performed to obtain the cDNA. For example, the cDNA fragment encoding "clone 3DD" was obtained through PCR due to the presence of an internal XhoI site. These cDNAs were then cloned into various expression vectors. These included pGEX (Pharmacia) or pMAL (New England Biolabs) for expression as a GST (Glutathione-S-transferase) or MBP (maltose binding protein) fusion protein in E. coli, a pED-based vector for mammalian expression, and pVL or pBlueBacHis (Invitrogen) for baculovirus/insect expression. For the immunodetection of TNF-R intracellular ligand expression in mammalian cells, an epitope sequence, "Flag," was inserted into the translational start site of the pED vector, generating the pED-Flag vector. cDNAs were then inserted into the pED-Flag vector. Thus, the expression of cDNA from pED-Flag yields a protein with an amino terminal Met, followed by the "Flag" sequence, Asp-Tyr-Lys-Asp-Asp-Asp-Asp-Lys. (SEQ ID NO:10) Standard DEAE-Dextran or lipofectamine methods were used to transfect COS or CHO dukx cells. Immunodetection of Flag-tagged proteins was achieved using the M2 antibody (Kodak). Moreover, an immunoaffinity column using the M2 antibody, followed by elution with the "Flag" peptide, can be used for the rapid purification of the flag-tagged protein. Similarly, affinity purification of GST-, MBP- or His-tagged fusion proteins can be performed using glutathione, amylose, or nickel columns. Detailed purification protocols are provided by the manufacturers. For many fusion proteins, the TNF-R intracellular ligand can be released by the action of thrombin, factor Xa, or enterokinase cleavage. In the case where highly purified material is required, standard purification procedures, such as ion-exchange, hydrophobic, and gel filtration chromatography will be applied in addition to the affinity purification step.

FIGS. 1 and 2 depict autoradiographs demonstrating the expression of TNF-R1-DD ligand proteins in yeast and mammalian cells. FIG. 1 shows the results of expression of isloated clones of the present invention in yeast. EGY48 was transformed with pJG4–5 containing clone 2DD, 3DD or 20DD. Cells were then grown overnight in the galactose/ raffinose medium. Cell lysates were prepared and subject to 4–20% SDS gel electrophoresis, followed by Western blot analysis using anti-HA antibody (12CA5, Boehringer Mannheim, Indianapolis, Ind.). FIG. 2 shows the results of expression of Flag-2DD and Flag-20DD in COS cells. COS cells were transfected with either pED-Flag (Vector control), Flag-2DD or Flag-20DD plasmid by the lipofectamine method. Thirty μg of each cell lysate were prepared and subjected to 4–20% SDS gel electrophoresis, followed by Western blot analysis using M2 antibody (Kodak). The bands in the Flag-2DD and Flag-20DD lanes indicate significant expression of the respective TNF-R1-DD ligand proteins.

EXAMPLE 3

ASSAYS OF TNF-R DEATH DOMAIN BINDING

Two different methods were used to assay for TNF-R1-DD ligand protein activity. The first assay measures binding in the yeast strain in "interaction trap," the system used here to screen for TNF-R1-DD interacting proteins. In this system, the expression of reporter genes from both LexAop-Leu2 and LexAop-LacZ relies on the interaction between the bait protein, in this case TNF-R1DD, and the prey, the TNF-R intracellular ligand. Thus, one can measure the strength of the interaction by the level of Leu2 or LacZ expression. The most simple method is to measure the activity of the LacZ encoded protein, β-galactosidase. This activity can be judged by the degree of blueness on the X-Gal containing medium or filter. For the quantitative measurement of β-galactosidase activity, standard assays can be found in "Methods in Yeast Genetics" Cold Spring Harbor, N.Y., 1990 (by Rose, M. D., Winston, F., and Hieter, P.).

The second assay for measuring binding is a cell-free system. An example of a typical assay is described below. Purified GST-TNF-R1-DD fusion protein (2 ug) was mixed with amylose resins bound with a GST-TNF-R1-DD intracellular ligand for 2 hour at 4° C. The mixture was then centrifuged to separate bound (remained with the beads) and unbound (remained in the supernatant) GST-TNF-R1-DD. After extensive washing, the bound GST-TNF-R1-DD was eluted with maltose and detected by Western blot analysis using a GST antibody. The TNF-R1-DD or the intracellular ligand can also be immobilized on other solid supports, such as on plates or fluorobeads. The binding can then be measured using ELISA or SPA (scintillation proximity assay).

EXAMPLE 4

CHARACTERIZATION OF TNF-R DEATH DOMAIN LIGAND PROTEIN

Mapping the Interaction Site in TNF-R1

Many of the key amino acids for TNF-R signaling have been determined by site-directed mutagenesis (Tataglia et al., Cell 74:845–853 (1993). These amino acids are conserved between TNF-R and the Fas antigen, which is required for mediating cytotoxicity and other cellular responses. In order to test if the TNF-R intracellular proteins interact with these residues, the following mutations were constructed: F345A (substitution of phe at amino acid 345 to Ala), R347A, L351A, F345A/R347A/L351A, E369A, W378A and I408A. The ability of the mutant protein to interact with the intracellular ligand in the "interaction trap" system was tested.

Effect on the TNF-mediated Response

The effect of the TNF-R intracellular ligands on the TNF-mediated response can be evaluated in cells overexpressing the ligands. A number of TNF-mediated responses, including transient or prolonged responses, can be measured. For example, TNF-induced kinase activity toward either MBP (myelin basic protein) or the N-terminus (amino acids 1–79) of c-jun can be measured in COS cells or CHO cells either transiently or stably overexpressing clone 2DD, 3DD or clone 20DD. The significance of these ligand proteins in TNF-mediated cytotoxicity and other cellular responses can be measured in L929 or U937 overexpressing cells. Alternatively, other functional assays, such as the induction of gene expression or $PGE_2$ production after prolonged incubation with TNF, can also be used to measure the TNF mediated response. Conversely, the significance of the TNF-R1-DD ligand proteins in TNF signaling can be established by lowering or eliminating the expression of the ligands. These experiments can be performed using antisense expression or transgenic mice.

Enzymatic or Functional Assays

The signal transduction events initiated by TNF binding to its receptor are still largely unknown. However, one major result of TNF binding is the stimulation of cellular serine/ threonine kinase activity. In addition, TNF has been shown to stimulate the activity of PC-PLC, $PLA_2$, and sphingomyelinase. Therefore, some of the TNF-R1-DD ligand proteins may possess intrinsic enzymatic activity that is responsible for these activities. Therefore, enzymatic assays can be performed to test this possibility, particularly with those clones that encode proteins with sequence homology to known enzymes. In addition to enzymatic activity, based on the sequence homology to proteins with known function, other functional assays can also be measured.

EXAMPLE 5

ISOLATION OF FULL LENGTH CLONES

In many cases, cDNAs obtained from the interaction trap method each encode only a portion of the full length protein. For example, based on identity and sequence and the lack of the initiating methionine codon, clones 2DD, 3DD and 20DD apparently do not encode full length proteins. Therefore, it is desirable to isolate full length clones. The cDNAs obtained from the screening, such as clone 2DD, are used as probes, and the cDNA libraries described herein, or alternatively phage cDNA libraries, are screened to obtain full length clones in accordance with known methods (see for example, "Molecular Cloning, A Laboratory Manual", by Sambrook et al., 1989 Cold Spring Harbor).

EXAMPLE 6

ANTIBODIES SPECIFIC FOR TNF-R INTRACELLULAR LIGAND PROTEIN

Antibodies specific for TNF-R intracellular ligand proteins can be produced using purified recombinant protein, as described in Example 2, as antigen. Both polyclonal and monoclonal antibodies will be produced using standard techniques, such as those described in "Antibodies, a Laboratory Manual" by Ed Harlow and David Lane (1988), Cold Spring Harbor Laboratory.

EXAMPLE 7

CHARACTERIZATION OF CLONES 1TU AND 15/27TU

Specificity of Interaction

The specificity of clones 1TU, 15TU and 27TU was tested using a panel of baits. The ability of these clones to bind the TNF-R death domain was compared to their binding to the intracellular domain of the second TNF-R (TNF-R $p75_{IC}$), the entire intracellular domain of TNF-R (TNF-R $p55_{IC}$), the death domain of the fas antigen (which shares 28% identity with TNF-R-DD) ($Fas_{DD}$), the Drosophila transcription factor bicoid, and a region of the IL-1 receptor known to be critical for signalling ($IL-1R_{477-527}$). As shown in Table 1, none of these clones interacted with TNF-R $p75_{IC}$ or $Fas_{DD}$, and only 1TU interacted with bicoid. In contrast, both 1TU and 15TU bound the cytoplasmic domain of the p55 TNF-R, as well as residues 477–527 of the IL-1R. 27TU interacted relatively weakly with these sequences.

TABLE 1

| clone | $TNF-R_{DD}$ | TNF-R $p75_{IC}$ | TNF-R $p55_{IC}$ | $Fas_{DD}$ | bicoid | IL-1R (477–527) |
|---|---|---|---|---|---|---|
| 1TU  | +++ | −  | +++ | − | ++ | +++ |
| 15TU | +++ | ±  | +++ | − | −  | ++  |
| 27TU | +++ | −  | +   | − | −  | +   |

Interaction with Amino Acids Critical for Signalling

The ability of each clone to interact with four single-site mutations in the TNF-R death domain (each known to abolish signalling) was measured. As shown in Table 2, each of the clones interacted less strongly with the death domain mutants than with the wild type death domain, suggesting that these clones may bind critical residues in vivo.

TABLE 2

| clone | $TNF-R_{DD}$ | F345A | L351A | W378A | I408A |
|---|---|---|---|---|---|
| 1TU  | +++ | + | ++ | ++ | +  |
| 15TU | +++ | + | +  | ++ | ++ |
| 27TU | +++ | + | +  | ±  | ++ |

Expression of 1TU, 15TU and 27TU

Figure 3A:
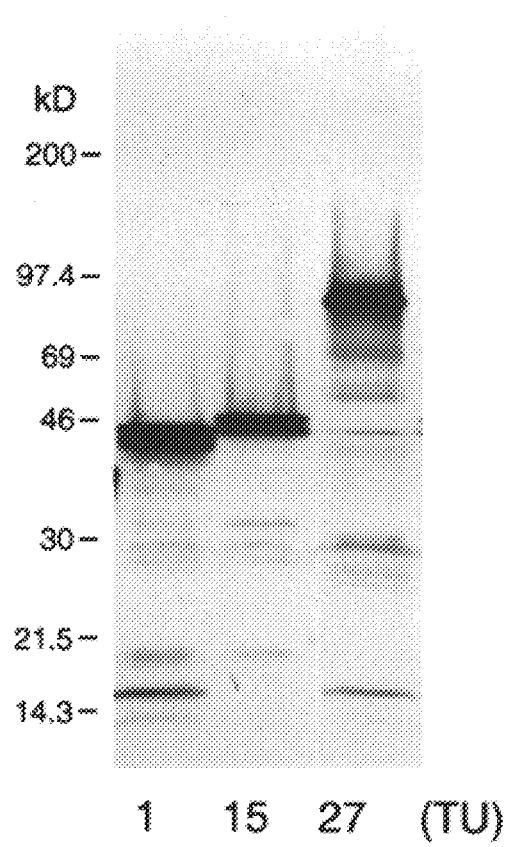
FIGS. 3A and 3B depict an autoradiograph demonstrating the expression of clones 1TU, 15TU and 27TU.
Figure 3B:
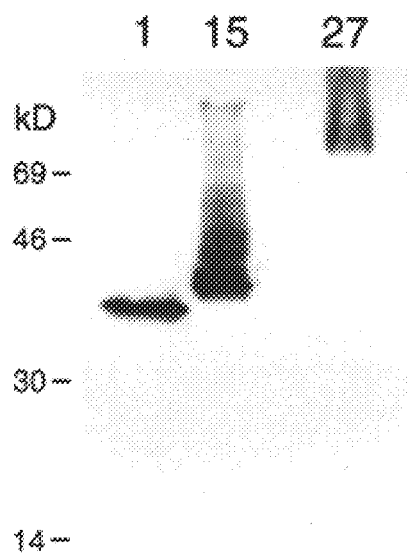

FIGS. 3A and 3B depict an autoradiograph demonstrating the expression of clones 1TU, 15TU and 27TU in yeast (A) and COS cells (B).

In (A): EGY48 was transformed with pJG4–5 containing clones 1TU, 15TU or 27TU. Cells were then grown overnight in galactose/raffinose medium. Cell lysates were prepared and subjected to 4–20% SDS gel electrophoresis, followed by Western blot analysis using anti-HA antibody (12CA5, Boehringer Mannheim).

In (B): COS cells were transfected with pED-Flag containing clones 1TU, 15TU and 27TU. Cell lysates were prepared and analyzed by Western blot using anti-Flag antibody (M2, Kodak).

Specific Binding of 1TU and 27TU to TNF-R1-DD

The interaction of 1TU and 27TU with TNF-R1-DD was tested using purified bacterially expressed fusion proteins. As shown in FIG. 4, MBP fusion proteins containing 1TU or 27TU bound only to TNF-R1-DD expressed as a GST fusion protein, but not to GST protein alone. In the control experiment, MBP protein did not bind either GST or GST/TNF-R1-DD. These results indicate that 1TU and 27TU bound specifically to the TNF-R1 death domain in vitro, confirming the data obtained in the interaction trap.

15TU and 27TU Activation of JNK Activity

Figure 5:
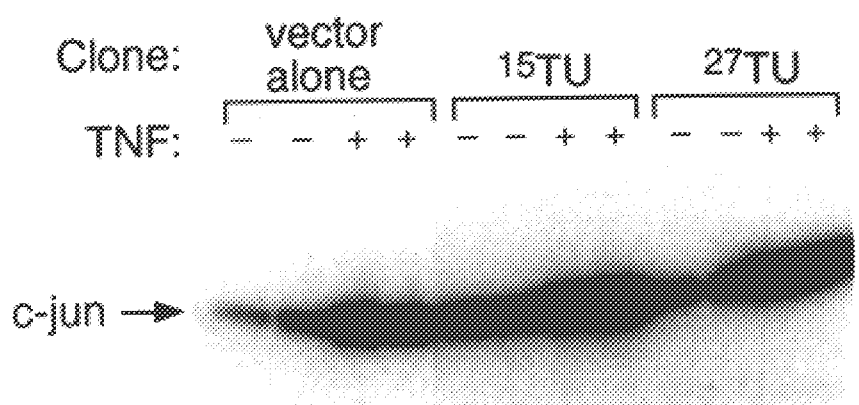
FIG. 5 demonstrates the ability of 15TU and 27TU to activate the JNK pathway. COS cells were contransfected with HA-tagged JNK1 and clones 15tu or 27TU. Cells were left untreated or treated for 15 min with 50 ng/ml TNF, and HA-JNK1 was immunoprecipitated with anti-HA antibody. JNK activity was measured in an in vitro kinase assay using GST-c-jun (amino acids 1–79) as substrate, and reactions were electrophoresed on SDS-PAGE.

The jun N-terminal kinase (JNK) is normally activated within 15 min of TNF treatment in COS cells. 15TU and 27TU were cotransfected with an epitope tagged version of JNK, HA-JNK, in duplicate. After TNF treatment, JNK was immunoprecipitated with anti-HA antibody and JNK activity was measured in immunoprecipitation kinase assays, using GST-c-jun (amino acids 1–79) as substrate). Reactions were electrophoresed on SDS-PAGE. As shown in FIG. 5, transfection of 15TU and 27TU, but not vector alone, into COS cells activated JNK even in the absence of TNF, suggesting that these clones are involved in signal transduction of TNF and the pathway leading to JNK activation in vivo.

EXAMPLE 8

ISOLATION, EXPRESSION AND ASSAY OF CLONE 3TW

Figure 6:
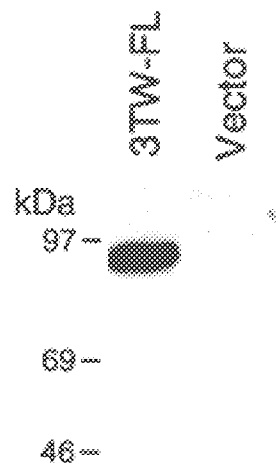
FIG. 6 is an autoradiograph of an SDS-PAGE gel of conditioned media from COS cells transfected with clone 3TW.

Clone 3TW was isolated from the WI38 cDNA library using clone 3DD as a porbe. Clone 3TW was expressed. FIG. 6 is an autoradiograph which demonstrates expression of 3TW (indicated by arrow).

Figure 7:
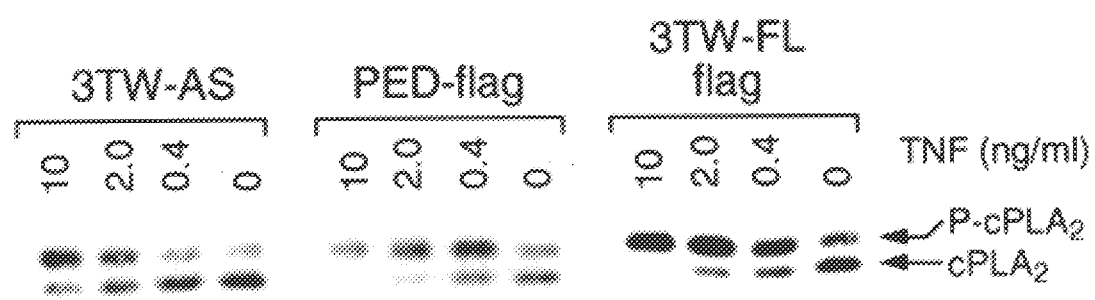
FIG. 7 is an autoradiograph which demonstrates that an antisense oligonucleotide derived from the sequence of clone 3TW inhibits TNF-induced cPLA$_2$ phosphorylation.

An antisense oligonucleotide was derived from the sequence of clone 3TW. The antisense oligonucleotide was assayed to determine its ability to inhibit TNF-induced $cPLA_2$ phosphorylation. FIG. 7 depicts the results of that experiment. Activity of the anitsense oligonucleotide (3TWAS) was compared with the full-length clone (3TWFL), Flag-3TW full length (3TWFLflag) and pED-flag vector (pEDflag). The antisense oligonucleotide inhibited phosphorylation.

---

What is claimed is:

1. TNF-R1-DD ligand protein produced according to a method which comprises:
   (a) growing a culture of a host cell in a suitable culture medium, wherein the host cell is transformed with a composition comprising an isolated polynucleotide operably linked to an expression control sequence, wherein the polynucleotide is selected from the group consisting of:
      (aa) a polynucleotide comprising the nucleotide sequence of SEQ ID NO:9 from nucleotide 2 to nucleotide 931;
      (ab) a polynucleotide comprising a fragment of the nucleotide sequence of SEQ ID NO:9, the fragment encoding a protein having TNF-R1-DD ligand protein activity;
      (ac) a polynucleotide encoding an TNF-R1-DD ligand protein comprising the amino acid sequence of SEQ ID NO:10; and
      (ad) a polynucleotide encoding an TNF-R1-DD ligand protein comprising a fragment of the amino acid sequence of SEQ ID NO:10, the fragment having TNF-R1-DD ligand protein activity; and
   (b) purifying the TNF-R1-DD ligand protein from the culture.

2. A composition comprising an isolated polynucleotide, wherein said polynucleotide is selected from the group consisting of:
   (a) a polynucleotide comprising the nucleotide sequence of SEQ ID NO:9 from nucleotide 2 to nucleotide 931;
   (b) a polynucleotide comprising a fragment of the nucleotide sequence of SEQ ID NO:9 the fragment encoding a protein having TNF-R1-DD ligand protein activity;
   (c) a polynucleotide encoding an TNF-R1-DD ligand protein comprising the amino acid sequence of SEQ ID NO:10;
   (d) a polynucleotide encoding an TNF-R1-DD ligand protein comprising a fragment of the amino acid sequence of SEQ ID NO:10, the fragment having TNF-R1-DD ligand protein activity; and
   (e) a polynucleotide capable of hybridizing under stringent conditions to any one of the polynucleotides specified in (a)–(d).

3. The composition of claim 2 wherein said polynucleotide is selected from the group consisting of (a), (b) (c) and (d) and wherein said polynucleotide is operably linked to an expression control sequence.

4. A host cell transformed with a composition of claim 3.

5. The host cell of claim 4, wherein said cell is a mammalian cell.

6. A process for producing an TNF-R1-DD ligand protein, which comprises:
   (a) growing a culture of the host cell of claim 4 in a suitable culture medium; and
   (b) purifying the TNF-R1-DD ligand protein from the culture.

7. A composition comprising a protein having TNF-R1-DD ligand protein activity, wherein said protein comprises an amino acid sequence selected from the group consisting of:
   (a) the amino acid sequence of SEQ ID NO:10; and
   (b) fragments of the amino acid sequence of SEQ ID NO:10 having TNF-R1-DD ligand protein activity;
said protein being substantially free from other mammalian proteins.

8. The composition of claim 7 wherein said protein comprises the amino acid sequence of SEQ ID NO:10.

9. A composition comprising an isolated polynucleotide, wherein said polynucleotide is selected from the group consisting of:
   (a) a polynucleotide comprising the nucleotide sequence of SEQ ID NO:17 from nucleotide 14 to nucleotide 2404;
   (b) a polynucleotide comprising a fragment of the nucleotide sequence of SEQ ID NO:17, the fragment encoding a protein having TNF-R1-DD ligand protein activity;
   (c) a polynucleotide encoding an TNF-R1-DD ligand protein comprising the amino acid sequence of SEQ ID NO:18;
   (d) a polynucleotide encoding an TNF-R1-DD ligand protein comprising a fragment of the amino acid sequence of SEQ ID NO:18, the fragment having TNF-R1-DD ligand protein activity;
   (e) a polynucleotide encoding an TNF-R1-DD ligand protein comprising a fragment of the amino acid sequence of SEQ ID NO:18, the fragment comprising the amino acid sequence of SEQ ID NO:18 from amino acid 488 to amino acid 797; and (f) a polynucleotide capable of hybridizing under stringent conditions to any one of the polynucleotides specified in (a)–(e).

10. The composition of claim 9 wherein said polynucleotide is operably linked to an expression control sequence.

11. A host cell transformed with a composition of claim 10.

12. The host cell of claim 11, wherein said cell is a mammalian cell.

13. A process for producing an TNF-R1-DD ligand protein, which comprises:

(a) growing a culture of the host cell of claim 11 in a suitable culture medium; and (b) purifying the TNF-R1-DD ligand protein from the culture.

14. A composition comprising a protein having TNF-R1-DD ligand protein activity, wherein said protein comprises an amino acid sequence selected from the group consisting of:

(a) the amino acid sequence of SEQ ID NO:18;

(b) fragments of the amino acid sequence of SEQ ID NO:18 having TNF-R1-DD ligand protein activity; and (c) fragments of the amino acid sequence of SEQ ID NO:18 comprising the amino acid sequence of SEQ ID NO:18 from amino acid 488 to amino acid 797;

said protein being substantially free from other mammalian proteins.

15. The composition of claim 14 wherein said protein comprises the amino acid sequence of SEQ ID NO:18.

16. The composition of claim 14, wherein the protein comprises an amino acid sequence comprising a fragment of the amino acid sequence of SEQ ID NO:18, the fragment comprising the amino acid sequence of SEQ ID NO:18 from amino acid 488 to amino acid 797.

17. A composition comprising an isolated polynucleotide encoding a protein having TNF-R1-DD ligand protein activity, wherein the polynucleotide is selected from the group consisting of:

(a) a polynucleotide comprising the nucleotide sequence of SEQ ID NO:9 from nucleotide 2 to nucleotide 931; and (b) a polynucleotide encoding an TNF-R1-DD ligand protein comprising the amino acid sequence of SEQ ID NO:10.

18. The composition of claim 17, wherein the polynucleotide comprises the nucleotide sequence of SEQ ID NO:9 from nucleotide 2 to nucleotide 931.

19. The composition of claim 17, wherein the polynucleotide encodes an TNF-R1-DD ligand protein comprising the amino acid sequence of SEQ ID NO:10.

20. TNF-R1-DD ligand protein produced according to a method which comprises:

(a) growing a culture of a host cell in a suitable culture medium, wherein the host cell is transformed with a composition comprising an isolated polynucleotide operably linked to an expression control sequence, wherein the polynucleotide is selected from the group consisting of:

(aa) a polynucleotide comprising the nucleotide sequence of SEQ ID NO:17 from nucleotide 14 to nucleotide 2404;

(ab) a polynucleotide comprising a fragment of the nucleotide sequence of SEQ ID NO:17, the fragment encoding a protein having TNF-R1-DD ligand protein activity;

(ac) a polynucleotide encoding an TNF-R1-DD ligand protein comprising the amino acid sequence of SEQ ID NO:18;

(ad) a polynucleotide encoding an TNF-R1-DD ligand protein comprising a fragment of the amino acid sequence of SEQ ID NO:18, the fragment having TNF-R1-DD ligand protein activity; and (ae) a polynucleotide encoding an TNF-R1-DD ligand protein comprising a fragment of the amino acid sequence of SEQ ID NO:18, the fragment comprising the amino acid sequence of SEQ ID NO:18 from amino acid 488 to amino acid 797; and (b) purifying the TNF-R1-DD ligand protein from the culture.

21. A composition comprising an isolated polynucleotide encoding a protein having TNF-R1-DD ligand protein activity, wherein the polynucleotide is selected from the group consisting of:

(a) a polynucleotide comprising the nucleotide sequence of SEQ ID NO:17 from nucleotide 14 to nucleotide 2404; and (b) a polynucleotide encoding an TNF-R1-DD ligand protein comprising the amino acid sequence of SEQ ID NO:18.

22. The composition of claim 21, wherein the polynucleotide comprises the nucleotide sequence of SEQ ID NO:17 from nucleotide 14 to nucleotide 2404.

23. The composition of claim 21, wherein the polynucleotide encodes an TNF-R1-DD ligand protein comprising the amino acid sequence of SEQ ID NO:18.

* * * * *